US012410165B2

(12) United States Patent
Nam et al.

(10) Patent No.: US 12,410,165 B2
(45) Date of Patent: Sep. 9, 2025

(54) DIFFERENT FORMS OF 6-CHLORO-2-ETHYL-N- (4-(4-(4-(TRIFLUOROMETHOXY) PHENYL)PIPERIDINE-1-YL)BENZYL)IMIDAZO[1,2-A]PYRIDINE-3-CARBOXAMIDE

(71) Applicant: QURIENT CO., LTD., Gyeonggi-do (KR)

(72) Inventors: Kiyean Nam, Gyeonggi-do (KR); Jaeseung Kim, Seoul (KR); Chunwon Jung, Gyeonggi-do (KR); Saeyeon Lee, Gyeonggi-do (KR)

(73) Assignee: Qurient Co., Ltd., Gyeonggi-Do (KR)

( * ) Notice: Subject to any disclaimer, the term of this patent is extended or adjusted under 35 U.S.C. 154(b) by 714 days.

(21) Appl. No.: 17/627,928

(22) PCT Filed: Jul. 30, 2019

(86) PCT No.: PCT/EP2019/070524

§ 371 (c)(1),
(2) Date: Jan. 18, 2022

(87) PCT Pub. No.: WO2021/018387

PCT Pub. Date: Feb. 4, 2021

(65) Prior Publication Data

US 2023/0141783 A1 May 11, 2023

(51) Int. Cl.
*C07D 471/04* (2006.01)
*A61K 45/06* (2006.01)

(52) U.S. Cl.
CPC ............ *C07D 471/04* (2013.01); *A61K 45/06* (2013.01); *C07B 2200/13* (2013.01)

(58) Field of Classification Search
CPC .... C07D 471/04; A61K 45/06; C07B 2200/13
See application file for complete search history.

(56) References Cited

U.S. PATENT DOCUMENTS

2013/0065884 A1 3/2013 Korea et al.

FOREIGN PATENT DOCUMENTS

WO 2011113606 A1 9/2011
WO 2019068910 A1 4/2019

OTHER PUBLICATIONS

Shishu, et al. Ditosylate Salt of Itraconazole and Dissolution Enhancement Using Cyclodextrins. AAPS PharmSciTech 13, 863-874 (2012). (Year: 2012).*
Pethe, K., et al. "Discovery of Q203, a potent clinical candidate for the treatment of tuberculosis." Nature medicine 19.9 (2013): pp. 1157-1162.
The English translation of the Chinese Office Action, mailed on Mar. 21, 2024, in the related Chinese Appl. No. 201980099049.8.
The English translation of the Japanese Office Action, mailed on Jan. 31, 2024, in the related Japanese Appl. No. 2022-505572.
The English translation of the Japanese Office Action, mailed on Jun. 16, 2023, in the related Japanese Appl. No. 2022-505572.
The extended European search report, mailed on Dec. 9, 2024, in the related European Appl. No. 24176134.5.
The Israel Office Action, mailed on Dec. 19, 2024, in the related Israel Appl. No. 290047.
The Examination Report No. 1, mailed on Feb. 28, 2025, in the related Australian Appl. No. 2019459233.
The Philippine Office Action, mailed on Jun. 4, 2025, in the related Philippine Appl. No. 1-2022-550186.

* cited by examiner

*Primary Examiner* — Kortney L. Klinkel
*Assistant Examiner* — Donna M Nestor

(57) ABSTRACT

The present invention relates to different forms of the compound 6-chloro-2-ethyl-N-(4-(4-(4-(trifluoromethoxy) phenyl)piperidine-1-yl)benzyl)imidazo[1,2-a]pyridine-3-carboxamide and to methods of making such forms/compounds. The present invention furthermore relates to mono-acid addition salts thereof, to methods of making such mono-acid addition salts and to pharmaceutical compositions comprising any of the aforementioned compounds. Furthermore, the present invention relates to uses of any of these compounds.

16 Claims, 78 Drawing Sheets

Water content as function of RH

Water content as function of RH

DIFFERENT FORMS OF 6-CHLORO-2-ETHYL-N-(4-(4-(4-(TRIFLUOROMETHOXY)PHENYL)PIPERIDINE-1-YL)BENZYL)IMIDAZO[1,2-A]PYRIDINE-3-CARBOXAMIDE

CROSS REFERENCE TO RELATED APPLICATIONS

This application is a National Stage Application of International Application Number PCT/EP2019/070524, filed Jul. 30, 2019.

FIELD OF THE INVENTION

The present invention relates to different forms of the compound 6-chloro-2-ethyl-N-(4-(4-(4-(trifluoromethoxy)phenyl)piperidine-1-yl)benzyl)imidazo[1,2-a]pyridine-3-carboxamide and to methods of making such forms/compounds. The present invention furthermore relates to mono-acid addition salts thereof, to methods of making such mono-acid addition salts and to pharmaceutical compositions comprising any of the aforementioned compounds. Furthermore, the present invention relates to uses of any of these compounds.

BACKGROUND OF THE INVENTION

Tuberculosis as a disease continues to result in millions of deaths each year. Inadequate use of chemotherapy has led to an increasing number of drug resistant cases. This situation is likely to worsen with the emergence of extremely resistant strains to all currently known drugs. Current chemotherapy consists of compounds that directly target *Mycobacterium tuberculosis*, either by neutralizing general information pathways and critical processes such as RNA polymerization and protein synthesis inhibition or by interfering with mycobacterial specific cell envelop synthesis. The most widely used dedicated anti-tubercular drugs isoniazid, ethionamide, and pyriazin amide are pro-drugs that first require activation. They are administered to a patient for a course of several months. Patients infected with multi-drug resistant strains of *M. tuberculosis* may have to undergo combination therapies for extended periods of time.

WO 2011/113606 describes various anti-tubercular compounds and their use in the treatment of bacterial infections, including compound "Q203" which chemically is 6-chloro-2-ethyl-N-(4-(4-(4-(trifluoromethoxy)phenyl)piperidine-1-yl)benzyl)imidazo[1,2-a]pyridine-3-carboxamide. In a publication by Pethe et al. (Nature Medicine, 19, 1157-1160 (2013), this compound is reported to be active against tuberculosis by interfering with the bacterial energy metabolism, inhibiting cytochrome bcl activity which is an essential component of the electron transport chain required for synthesis of ATP.

Whilst the compound shows promise for future therapy of tuberculosis and related infections, there continues to be a need for forms thereof that are particularly suitable for pharmaceutical administration. In particular there is a need to provide forms that are showing an improved solubility in comparison to the free base of this compound. Furthermore, there is a need in the art to provide for forms that show an improved stability.

BRIEF SUMMARY

In a first aspect the present invention relates to a compound 6-chloro-2-ethyl-N-(4-(4-(4-(trifluoromethoxy)phenyl)piperidine-1-yl)benzyl)imidazo[1,2-a]pyridine-3-carboxamide ditosylate having the structure

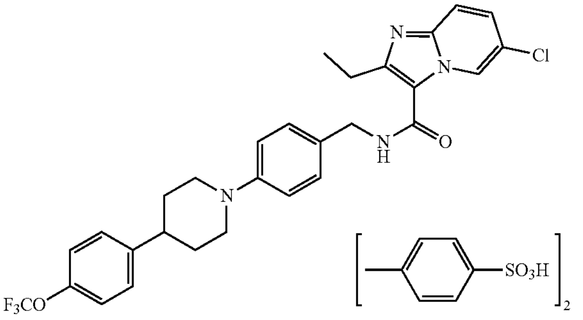

and furthermore having at least one or several of the following peaks in an X-ray Powder Diffraction (XRPD) spectrum obtained by irradiation with Cu-$K_\alpha$-radiation (Cu-$K_\alpha$):

3.9° 2θ, 5.6° 2θ, 8.0° 2θ, 16.1° 2θ, 19.1° 2θ, and 22.4° 2θ, ±0.2° 2θ.

In one embodiment, the compound has an XRPD spectrum as shown in FIG. 1.

In one embodiment, the compound has a differential scanning calorimetry (DSC) thermogram showing a single endotherm peak with an onset of 235° C.-237° C.

In one embodiment, the compound is produced by a method comprising the steps:

Providing, in any order, 6-chloro-2-ethyl-N-(4-(4-(4-(trifluoromethoxy)phenyl)piperidine-1-yl)benzyl)imidazo[1,2-a]pyridine-3-carboxamide free base and para-toluenesulphonic acid in a stoichiometric ratio of 1:2;

Mixing and dissolving them in a suitable solvent or solvent mixture, such as isopropylalcohol (IPA), tetrahydrofuran (THF), acetone or a mixture of THF and acetone;

Evaporating the solvent or solvent mixture.

In a further aspect, the present invention relates to a method for making the compound as defined above, said method comprising the steps:

Providing, in any order, 6-chloro-2-ethyl-N-(4-(4-(4-(trifluoromethoxy)phenyl)piperidine-1-yl)benzyl)imidazo[1,2-a]pyridine-3-carboxamide free base and para-toluenesulphonic acid in a stoichiometric ratio of 1:2;

Mixing and dissolving them in a suitable solvent or solvent mixture, such as isopropylalcohol (IPA), tetrahydrofuran (THF), acetone or a mixture of THF and acetone;

Evaporating the solvent or solvent mixture.

In a further aspect, the present invention relates to a mono-acid addition salt of 6-chloro-2-ethyl-N-(4-(4-(4-(trifluoromethoxy)phenyl)piperidine-1-yl)benzyl)imidazo[1,2-a]pyridine-3-carboxamide which is 6-chloro-2-ethyl-N-(4-(4-(4-(trifluoromethoxy)phenyl)piperidine-1-yl)benzyl)imidazo[1,2-a]pyridine-3-carboxamide mono-hydrochloride, 6-chloro-2-ethyl-N-(4-(4-(4-(trifluoromethoxy)phenyl)piperidine-1-yl)benzyl)imidazo[1,2-a]pyridine-3-carboxamide mono-phosphate, or 6-chloro-2-ethyl-N-(4-(4-(4-(trifluoromethoxy)phenyl)piperidine-1-yl)benzyl)imidazo[1,2-a]pyridine-3-carboxamide mono-tosylate.

In one embodiment, the mono-acid addition salt is 6-chloro-2-ethyl-N-(4-(4-(4-(trifluoromethoxy)phenyl)piperidine-1-yl)benzyl)imidazo[1,2-a]pyridine-3-carboxamide mono-hydrochloride having at least one or several of the following peaks in an X-ray Powder Diffraction (XRPD) spectrum obtained by irradiation with Cu-$K_\alpha$-radiation (Cu-$K_\alpha$):

6.4° 2θ, 8.1° 2θ, 16.2° 2θ, 17.2° 2θ, 24.3° 2θ and 25.0° 2θ, ±0.2° 2θ.

In one embodiment, the mono-acid addition salt is 6-chloro-2-ethyl-N-(4-(4-(4-(trifluoromethoxy)phenyl)piperidine-1-yl)benzyl)imidazo[1,2-a]pyridine-3-carboxamide mono-phosphate having at least one or several of the following peaks in an X-ray Powder Diffraction (XRPD) spectrum obtained by irradiation with Cu-$K_\alpha$-radiation (Cu-$K_\alpha$):

9.0° 2θ, 10.7±0.2° 2θ, 11.7° 2θ, 14.8° 2θ, 18.4° 2θ, 19.3° 2θ, and 21.8° 2θ, 22.8° 2θ, ±0.2° 2θ.

In one embodiment, the mono-acid addition salt is 6-chloro-2-ethyl-N-(4-(4-(4-(trifluoromethoxy)phenyl)piperidine-1-yl)benzyl)imidazo[1,2-a]pyridine-3-carboxamide mono-tosylate having at least one or several of the following peaks in an X-ray Powder Diffraction (XRPD) spectrum obtained by irradiation with Cu-$K_\alpha$-radiation (Cu-$K_\alpha$):

4.0° 2θ, 11.4° 2θ, 12.2° 2θ, 14.4° 2θ, 17.7° 2θ, 18.9° 2θ, 19.7° 2θ, 20.3° 2θ, 23.2° 2θ, and 26.7° 2θ, +0.2° 2θ.

In one embodiment, the mono-acid addition salt is the mono-hydrochloride salt and has an XRPD spectrum as shown in FIG. 2A.

In one embodiment, the mono-acid addition salt is the mono-phosphate salt and has an XRPD spectrum as shown in FIG. 2B.

In one embodiment, the mono-acid addition salt is the mono-tosylate salt and has an XRPD spectrum as shown in FIG. 3.

In a further aspect, the present invention relates to a method for preparing the mono-acid addition salt, as defined above, said method comprising the steps:

Providing, in any order, 6-chloro-2-ethyl-N-(4-(4-(4-(trifluoromethoxy)phenyl)piperidine-1-yl)benzyl)imidazo[1,2-a]pyridine-3-carboxamide free base and an acid selected from hydrochloric acid, phosphoric acid and para-toluenesulphonic acid in a stoichiometric ratio of 1:1;

Mixing and dissolving them in a suitable solvent or solvent mixture, such as isopropylalcohol (IPA), methyl tert-butyl ether (MTBE), tetrahydrofuran (THF), acetone or a mixture of THF and acetone;

Evaporating the solvent or solvent mixture.

In a further aspect, the present invention relates to a pharmaceutical composition comprising at least one compound according to the present invention or a mono-acid addition salt according to the present invention, together with at least one pharmaceutically acceptable carrier, excipient and/or diluent.

In one embodiment, the pharmaceutical composition further comprises at least one other pharmaceutically active agent.

In a further aspect, the present invention relates to the compound or the mono-acid addition salt according to the present invention as defined above, for use in the treatment of a bacterial infection.

In one embodiment, said bacterial infection is tuberculosis or Buruli ulcer.

In a further aspect, the present invention relates to a method treatment of a bacterial infection, in particular tuberculosis or Buruli ulcer, comprising the application of a suitable amount of a compound or of a mono-acid addition salt according to the present invention or of a pharmaceutical composition according to the present invention, to a patient in need thereof.

The inventors have found that a particular form of the compound's ditosylate salt, a crystal polymorph form, sometimes herein also designated as "pattern A" or "form A" was particularly stable, and other forms converted into such stable polymorph form. In an X-ray Powder Diffraction (XRPD) spectrum obtained by irradiation with Cu-$K_\alpha$-radiation, such form has at least one or several of the following peaks:

3.9° 2θ, 5.6° 2θ, 8.0° 2θ, 16.1° 2θ, 19.1° 2θ, and 22.4° 2θ, 0.2° 2θ.

The 2θ-values have a standard deviation of ±0.2° 2θ. In one embodiment, the compound has an XRPD-spectrum as shown in FIG. 1.

In comparison to other forms, this form appears to be the most stable form which makes it therefore particularly suitable for pharmaceutical formulations. In one embodiment, the compound according to the present invention has a differential scanning calorimetry (DSC) thermogram showing a single endotherm peak with an onset of approximately 235° C.-237° C.

In one embodiment, the compound according to the present invention has a differential scanning calorimetry (DSC) thermogram showing a single endotherm peak with an onset of 235° C.-237° C.

In one embodiment, the compound according to the present invention is produced by a method comprising the steps:

Providing, in any order, 6-chloro-2-ethyl-N-(4-(4-(4-(trifluoromethoxy)phenyl)piperidine-1-yl)benzyl)imidazo[1,2-a]pyridine-3-carboxamide free base and para-toluenesulphonic acid in a stoichiometric ratio of 1:2;

Mixing and dissolving them in a suitable solvent or solvent mixture, such as isopropylalcohol (IPA), tetrahydrofuran (THF), acetone or a mixture of THF and acetone;

Evaporating the solvent or solvent mixture.

The present invention also relates to a method for making the compound as defined above, said method comprising the steps:

Providing, in any order, 6-chloro-2-ethyl-N-(4-(4-(4-(trifluoromethoxy)phenyl)piperidine-1-yl)benzyl)imidazo[1,2-a]pyridine-3-carboxamide free base and para-toluenesulphonic acid in a stoichiometric ratio of 1:2;

Mixing and dissolving them in a suitable solvent or solvent mixture, such as isopropylalcohol (IPA), tetrahydrofuran (THF), acetone or a mixture of THF and acetone;

Evaporating the solvent or solvent mixture.

Furthermore, the inventors have also found that the compound according to the present invention, i. e. 6-chloro-2-ethyl-N-(4-(4-(4-(trifluoromethoxy)phenyl)piperidine-1-yl)benzyl)imidazo[1,2-a]pyridine-3-carboxamide ditosylate is stable under long-term storage conditions of 25° C. and 60% relative humidity for up to 60 months and under accelerated conditions of 40° C. and 75% relative humidity up to at least six months.

In a further aspect, the present invention also relates to a mono-acid addition salt of 6-chloro-2-ethyl-N-(4-(4-(4-(trifluoromethoxy)phenyl)piperidine-1-yl)benzyl)imidazo[1,2-a]pyridine-3-carboxamide, which is either mono-hydrochloride, mono-phosphate or mono-tosylate.

When the mono-acid addition salt is mono-hydrochloride, then the compound, in one embodiment has at least one or several of the following peaks in an X-ray Powder Diffraction (XRPD) spectrum obtained by irradiation with Cu-$K_\alpha$-radiation (Cu-$K_\alpha$):

6.4° 2θ, 8.1° 2θ, 16.2° 2θ, 17.2° 2θ, 24.3° 2θ and 25.0° 2θ, with all the 2θ values having a standard deviation±0.2° 2θ.

When the mono-acid addition salt is mono-phosphate, then the compound, in one embodiment has at least one or several of the following peaks in an X-ray Powder Diffraction (XRPD) spectrum obtained by irradiation with Cu-$K_\alpha$-radiation (Cu-$K_\alpha$):

9.0° 2θ, 10.7±0.2° 2θ, 11.7° 2θ, 14.8° 2θ, 18.4° 2θ, 19.3° 2θ, and 21.8° 2θ, 22.8° 2θ, ±0.2° 2θ.

When the mono-acid addition salt is the mono-tosylate, in one embodiment, it has at least one or several of the following peaks in an X-ray Powder Diffraction (XRPD) spectrum obtained by irradiation with Cu-$K_\alpha$-radiation (Cu-$K_\alpha$):

4.0° 2θ, 11.4° 2θ, 12.2° 2θ, 14.4° 2θ, 17.7° 2θ, 18.9° 2θ, 19.7° 2θ, 20.3° 2θ, 23.2° 2θ, and 26.7° 2θ, with all the 2θ values having a standard deviation of 0.2° 2θ.

In one embodiment of the aforementioned mono-acid addition salts, the respective compound has all of the aforementioned respective peaks in a X-ray Powder Diffraction (XRPD) spectrum obtained by irradiation with Cu-$K_\alpha$-radiation (Cu-$K_\alpha$).

In one embodiment, the mono-acid addition salt is the mono-hydrochloride and has an XRPD spectrum as shown in FIG. 2A.

In one embodiment, the mono-acid addition salt is the mono-phosphate and has an XRPD spectrum as shown in FIG. 2B.

In another embodiment it is the mono-tosylate and has a XRPD-spectrum as shown in FIG. 3.

In a further aspect, the present invention also relates to a method for preparing the mono-acid addition salt, as defined before, the method comprising the steps:

Providing, in any order, 6-chloro-2-ethyl-N-(4-(4-(4-(trifluoromethoxy)phenyl)piperidine-1-yl)benzyl)imidazo[1,2-a]pyridine-3-carboxamide free base and an acid selected from hydrochloric acid, phosphoric acid and para-toluenesulphonic acid in a stoichiometric ratio of 1:1;

Mixing and dissolving them in a suitable solvent or solvent mixture, such as isopropylalcohol (IPA), methyl tert-butyl ether (MTBE), tetrahydrofuran (THF), acetone or a mixture of THF and acetone;

Evaporating the solvent or solvent mixture.

The inventors have surprisingly found that the aforementioned three mono-acid addition salts have a greater solubility at low pH-values, in particular around pH1. This is important insofar, as this drug is supposed to be orally taken and therefore has to pass the gastrointestinal tract. An increased solubility, in comparison to the free base implies a greater bioavailability.

When reference is made herein to a scenario where a compound is described as having "an XRPD spectrum, as shown hereafter", this is meant to refer to a situation, where a compound has peaks and signals in an XRPD spectrum at positions as shown in the respective XRPD spectrum referred to. The intensity shown of individual peaks does not need to necessarily be identical, as long as there is a peak or signal at the indicated position, within the typical range(s) of tolerance for such XRPD spectra.

Furthermore, at low pH, especially around pH1, the mono-hydrochloride and the mono-phosphate salt have a better solubility in comparison to the di-tosylate salt.

Furthermore, the present invention also relates to a pharmaceutical composition comprising a compound 6-chloro-2-ethyl-N-(4-(4-(4-(trifluoromethoxy)phenyl)piperidine-1-yl)benzyl)imidazo[1,2-a]pyridine-3-carboxamide ditosylate as defined above, or a mono-acid addition salt of 6-chloro-2-ethyl-N-(4-(4-(4-(trifluoromethoxy)phenyl)piperidine-1-yl)benzyl)imidazo[1,2-a]pyridine-3-carboxamide, as defined above, together with at least one pharmaceutically acceptable carrier, excipient and/or diluent.

In one embodiment, such pharmaceutically composition further comprises at least one other pharmaceutically active agent.

In a further aspect, the present invention relates to the ditosylate compound, as defined above, or the mono-acid addition salt, as defined above, for use in the treatment of a bacterial infection.

In one embodiment, the bacterial infection is tuberculosis or Buruli ulcer.

In a further aspect, the present invention also relates to a method of treatment of a bacterial infection, in particular tuberculosis or Buruli ulcer, comprising the application of suitable amount of compound as defined above or of a mono-acid addition salt as defined above, or of a pharmaceutical composition, as defined above, to a patient in need thereof.

In yet a further aspect, the present invention also relates to the use of a ditosylate compound, as defined above, or of a mono-acid addition salt, as defined above, or of a pharmaceutical composition, as defined above, for the manufacture of a medicament for the treatment of a bacterial infection, wherein preferably, the bacterial infection is tuberculosis or Buruli ulcer.

It should be noted that, as used herein, the compound 6-chloro-2-ethyl-N-(4-(4-(4-(trifluoromethoxy)phenyl)piperidine-1-yl)benzyl)imidazo[1,2-a]pyridine-3-carboxamide is also sometimes herein referred to as "Q203".

BRIEF DESCRIPTION OF THE FIGURES

The invention is now further described by the following figures wherein.

Furthermore, reference is made to the following examples which are given to illustrate, not to limit the present invention.

DETAILED DISCLOSURE

Examples

Example 1

Summary

A polymorph screening study of Q203 using different crystallization techniques including slurry and salt formation experiments was performed. Due to the very low solubility of the solid in various solvents, cooling, evaporative and anti-solvents experiments were not performed. Eight XRPD patterns namely A, B, C, D, E, F, G and H were identified. Patterns A and C proved to be the true crystalline forms of the di-tosylate salt. The polymorph screening re-slurry experiments were carried out starting from Form A. Form A is a neat form; it maintains its crystalline form when exposed to 100% RH at RT for 6 days. Form C is also a neat form; it can be obtained by re-slurrying Form A in methanol; it maintains its crystalline form when exposed to 100% RH at RT for 6 days. Pattern G is obtained from water and its 1H-NMR shows that the ratio of base:acid is 1:1.3. Pattern H is also maintained its crystalline XRPD pattern when exposed to 100% RH at RT for 3 days. Pattern H is obtained from Toluene and its NMR shows that the ratio of base:acid is 3:3.46. Therefore, Patterns G and H are not considered to be the true polymorphs of the di-tosylate salt. Forms A and C were stirred in six pure solvents at RT and 50° C. for 4 days. According to the XRPD scans, the residual solid from stability experiments from the majority of solvents (THF, EtOH, and IPA) was Form A, but methanol as the re-slurry medium generated Form C. According to the data, Form A is considered to be more stable than Form C.

XRPD

Details of XRPD method used in the tests are mentioned below:

Rigaku D/MAX 2200 X-ray powder diffract meter

X-ray Generator: Cu, kα, (λ=1.54056 Å)

Tube Voltage: 40 kV, Tube Current: 40 mA

DivSlit: 1 deg

DivH.L.Slit: 10 mm

SctSlit: 1 deg

RecSlit: 0.15 mm

Monochromator: Fixed Monochromator

Scanning Scope: 3-36 deg (2-theta)

Scanning Step: 5 deg/min

DSC

Details of DSC method used in the tests are mentioned below:

Mettler Toledo Q2000 MDSC

Heat from 40° C. to 300° C. at 10° C./min

Experiments

Analysis of the Starting Material

Figure 1:
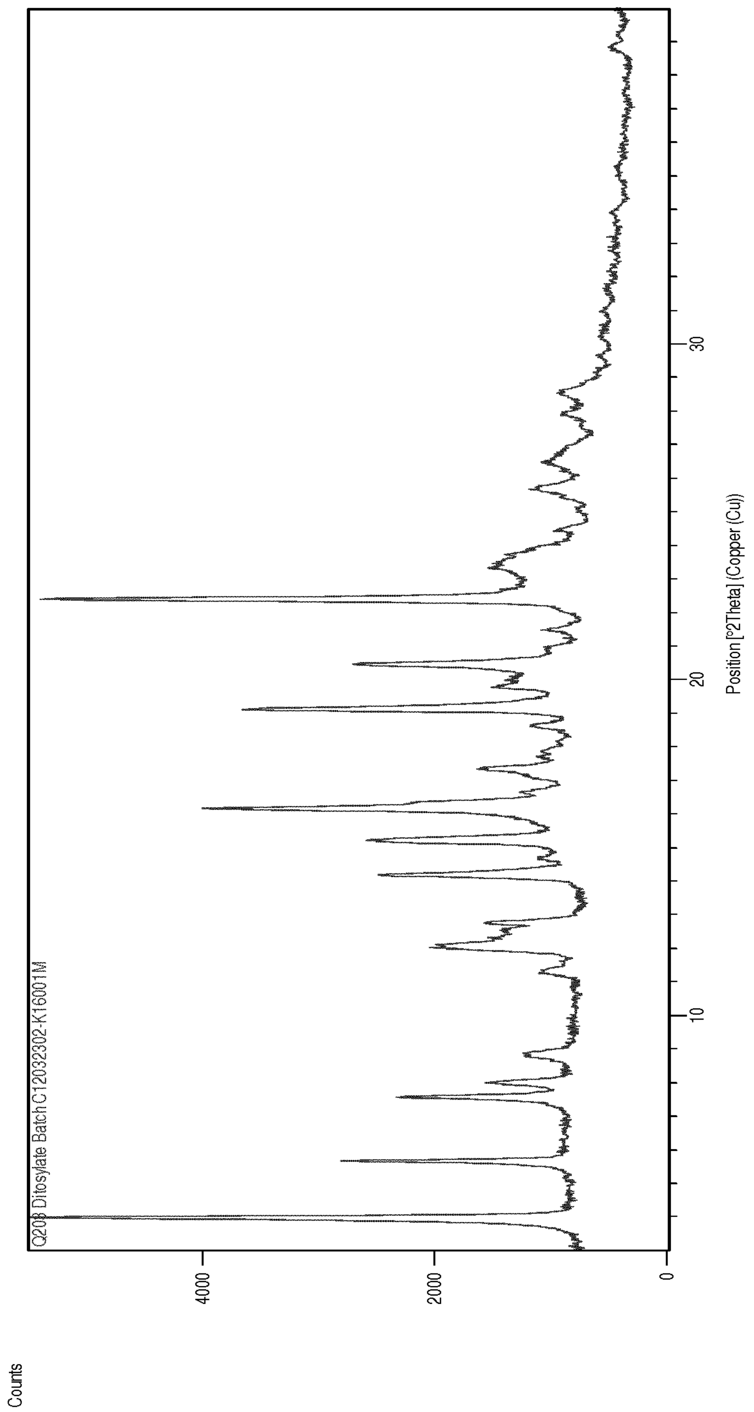
FIG. 1 shows an XRPD spectrum of Form A (or "pattern A") of Q203 ditosylate.
Figure 4:
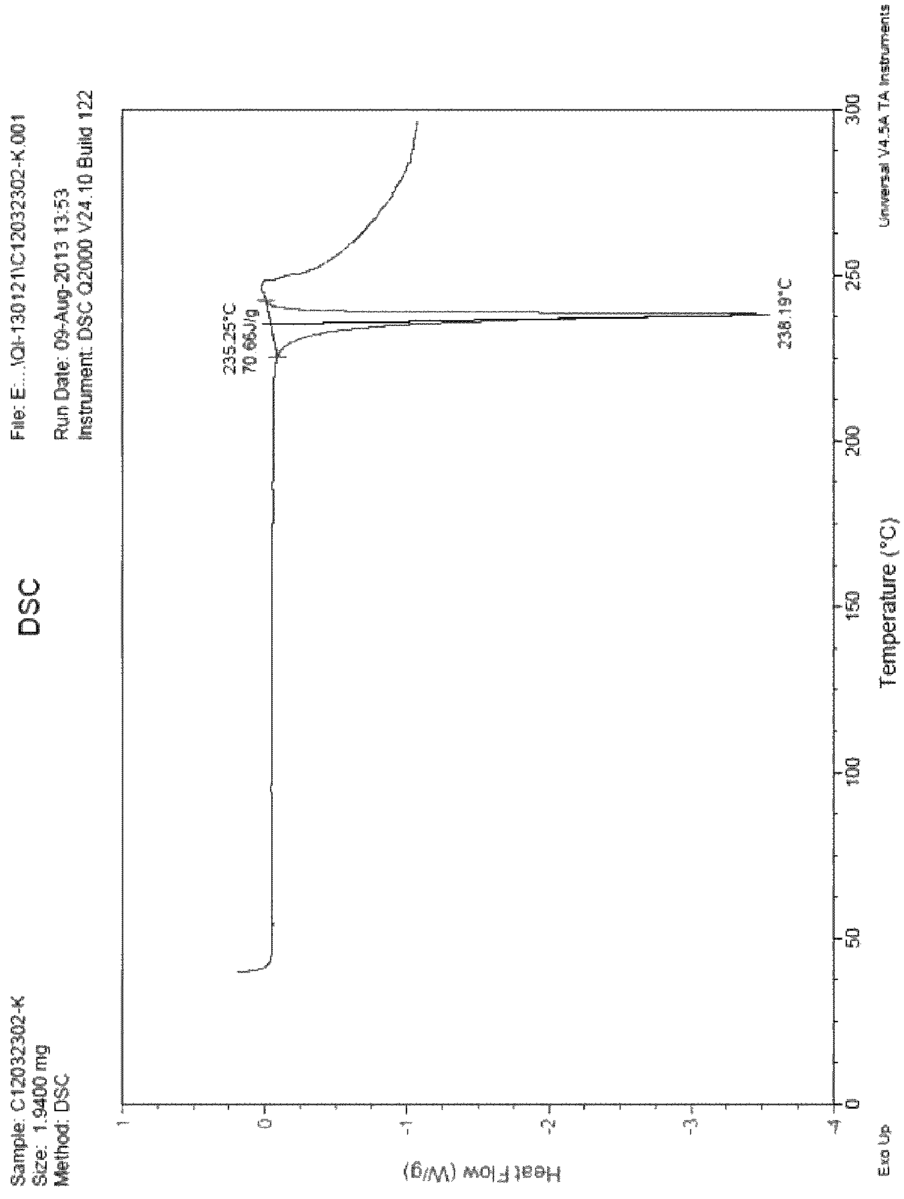
FIG. 4 shows a DSC scan of form A of Q203 ditosylate.
Figure 5:
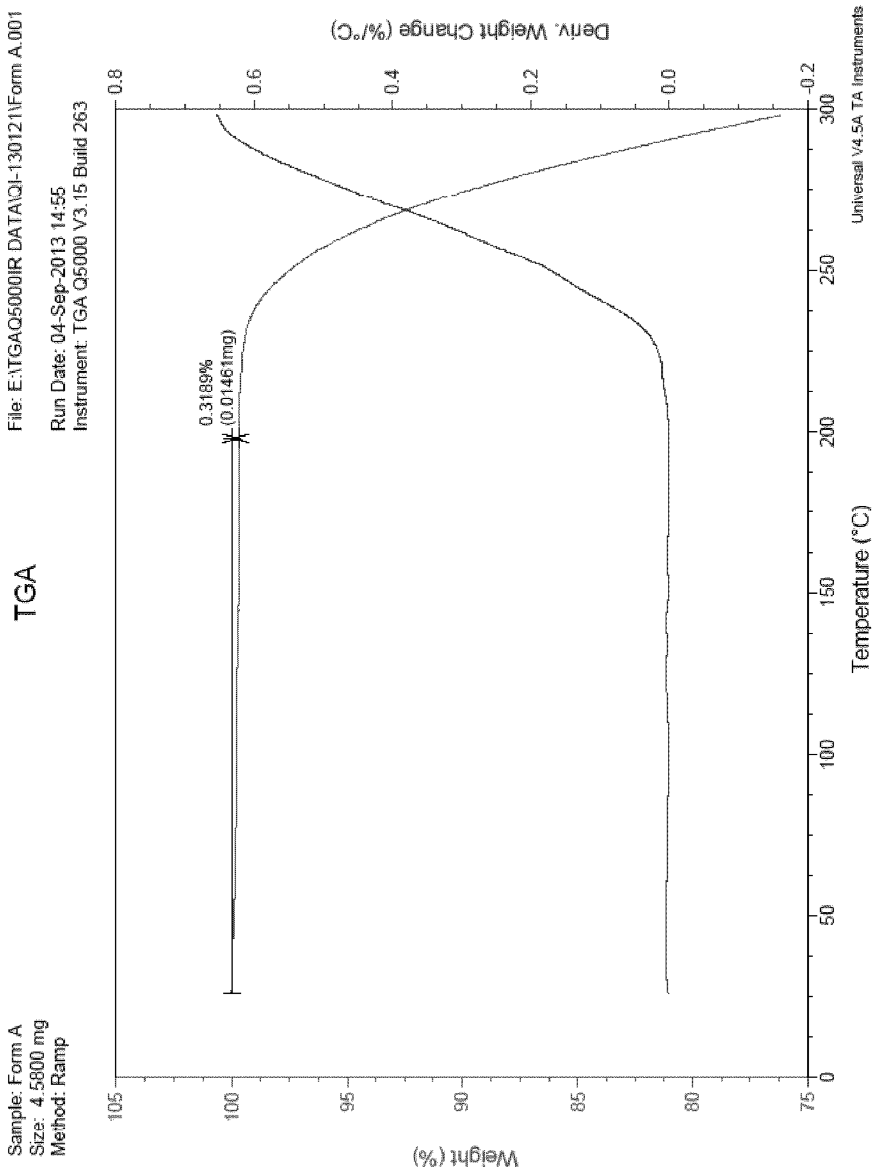
FIG. 5 shows a TGA scan of form A of Q203 ditosylate.

XRPD, DSC and TGA scan of the starting di-tosylate salt from A are shown in FIGS. 1, 4 and 5. According to XRPD, the solid (named as Form A) is crystalline; the DSC scan of the solid shows a melting onset temperature of around 235° C.; TGA data indicates a weight loss of 0.3% from 30° C.-200° C. The purity of the starting material is 99.46%.

Solubility Experiments

Exp 1: Solubility of the Free Base

The objective of measuring solubility of free base was to identify potential solvents for salt formation process development. Approximate solubility of the free base was measured by gravimetry method. Excess solids were added to various solvents including some Class III solvents (ICH guideline) at RT and 50° C. Since the solubility in these solvents is generally low, it was decided to mix water with these solvents. The suspensions were slurried for one day; the clear liquors from the top portion of the suspension were used for solubility determination by gravimetry method. The solubility data are given in Table 2-1. At 50° C., the solubility in IPA or its mixture with water is generally low (11-22 mg/ml), in acetone and its mixture with water is within 41-74 mg/ml range, in EA and its mixture with water is 55-98 mg/ml range, and in methyl acetate is 94-105 mg/ml range. The solubility in THF was 279 mg/ml at 50° C.

TABLE 2-1

Approximate solubility* data of the free base in pure solvents at RT and 50° C.

| | Solubility (mg/ml) | |
|---|---|---|
| Solvents | RT | 50° C. |
| Ethyl Acetate (EA) | 13 | 99 |
| EA + 4% water | 16 | 55 |
| Acetone | N/A | 48 |
| Acetone + 5% water | 22 | 74 |
| Acetone + 10% water | N/A | 42 |
| Isopropyl Alcohol (IPA) | N/A | 20 |
| IPA + 5% water | N/A | 22 |
| IPA + 15% water | N/A | 11 |
| Isopropyl Acetate (IPAC) | 26 | 51 |
| IPAC + 4% water | N/A | 35 |
| Tetrahydrofuran (THF) | 133 | 279 |
| Methyl Amine (MA) | 38 | 94 |
| MA + 4% water | 18 | 105 |

*The solubility numbers are approximate and are intended for process development only

Exp 2: Solubility of the Starting Material (Di-Tosylate Salt Form A)

Approximate solubility of the starting di-tosylate salt (Form A) was measured by gravimetry method. 100 mg of the solid was suspended in 10 vol of various solvents and stirred at RT and 50° C. for 3 days. The mother liquid was then used to measure the solubility. The results are shown in Table 2-2. According to the solubility data, the solid has a low solubility in most of the solvents except in MeOH. The solubility in MeOH is 126 mg/ml and 275 mg/ml at RT and 50° C., respectively.

TABLE 2-2

Approximate solubility* of the starting material in different pure solvents at RT and 50° C.

| Solvents | Solubility (mg/ml) | |
|---|---|---|
| | RT | 50° C. |
| Water | nil | 3 |
| Methanol (MeOH) | 126 | 275 |
| Ethanol (EtOH) | 1 | 7 |
| IPA | nil | 3 |
| EA | nil | nil |
| MA | nil | nil |
| IPAC | nil | nil |
| Methyl Ethyl Ketone (MEK) | nil | nil |
| Methul Isobutyl Ketone (MIBK) | nil | 2 |
| Acetone | nil | nil |
| Acetonitrile | nil | nil |
| THF | nil | nil |
| Toluene | 1 | 3 |
| Dichloromethane (DCM) | nil | nil |
| Methyl tert-Butyl Ether (TBME) | nil | nil |

*The solubility numbers are approximate and are intended for process development only

Polymorph Screening Experiments

Polymorph screening experiments were performed using two methods: slurry and salt formation experiment (reactive crystallization). Samples in some experiments were analyzed both before and after drying (wet and dry).

Re-Slurry Experiments

Exp 1: Re-Slurry in Different Pure Solvents for 7 Days at RT and 50° C.

Samples from residual solid from solubility experiments were used for XRPD analysis. Samples were analyzed both wet and dry to ensure potential solvates/hydrates are captured. Table 3-1 shows the analytical results. As it is observed, residual solid from re-slurry in water indicate pattern B. Re-slurry in methanol generated Form C. Ethanol, acetone (some experiments) and acetonitrile produced solid with pattern D. Some experiments using MEK and THF showed solid with pattern E or its mixture with A. All other samples generated solid with no change in their original XRPD pattern (Form A).

TABLE 3-1

Results of form screening by re-slurry in different pure solvents at RT and 50° C. for 7 days

| Solvents | RT | | | 50° C. | | |
|---|---|---|---|---|---|---|
| | 3 days (wet) | 3 days (dry) | 7 days (dry) | 3 days (wet) | 3 days (dry) | 7 days (dry) |
| Water | N/A | B | B | B | B | B |
| MeOH | C | C | C | N/A | N/A | N/A |
| EtOH | D | D | A | A | A | A |
| IPA | A | N/A | A | N/A | A | A |
| EA | A | A | A | A | A | A |
| MA | A | A | A | A | A | A |
| IPAc | A | A | A | A | A | A |
| MEK | A+E | E | A | A+E | E | A |
| MIBK | A | A | A | A | A | A |
| Acetone | D | D | A | A | A | A |
| Acetonitrile | D | D | D | D | D | D |
| THF | A+E | A | A | A+E | A | A |
| Toluene | A | A | A | A | A | A |
| DCM | A | A | A | A | A | A |
| TBME | A | A | A | A | A | A |

Exp 2: Re-Slurry in Binary Solvents for 5 Days at RT

In order to extend the slurry experiments, the mixture of solvents were used as the slurry medium. The residual solids were then analyzed by XRPD and DSC machines.

The procedures of the experiment are described below.

30 mg of Form B was added in a 1.5 ml vial

Binary solvents with the ratio 1:1 were papered according to the Table 4-1.

Suspensions were slurried at RT for 5 days

Samples were filtered and dried in oven at 50° C. by vacuum for 15 minutes

XRPD and DSC scans were taken

The results are shown in Table 4-1. It is noticed that methanol: water and IPA: water (0.5 ml: 0.5 ml) generated solids with pattern B. It is suspected that pattern B is associated with water, meaning that this pattern is generated when water is present. On the other hand, the majority of solvents in mixture with methanol produced pattern C. Starting from pattern A, methanol seems to be needed as at least part of the solvent to generate pattern C. In pure solvents, it was shown that in methanol, pattern A converts to pattern C. In further experiments it would be seen that reactive crystallization using solvents other than methanol could initially produce pattern C, but with extending time, pattern C transforms to pattern A. In two cases, a new XRPD pattern (F) was observed. Except for the above, it is noticed that pattern A remained unchanged in all other experiments.

TABLE 4-1

| Results of starting material re-slurry in binary solvents (50:50, vol:vol) at RT for 5 days | | | | | | | | | | | | | | |
|---|---|---|---|---|---|---|---|---|---|---|---|---|---|---|
| | Water | MeOH | EtOH | MA | EA | acetone | MeCN | THF | IPA | IPAC | TBME | MEK | DCM | Toluene |
| Water | | | | | | | | | | | | | | |
| MeOH | B | | | | | | | | | | | | | |
| EtOH | F | A | | | | | | | | | | | | |
| MA | | C | A | | | | | | | | | | | |
| EA | | C | D | A | | | | | | | | | | |
| Acetone | F | C | A | A | A | | | | | | | | | |
| MeCN | N/A | C | F | F | F | F | | | | | | | | |
| THF | A | A | A | A | A | A | A | | | | | | | |
| IPA | B | C | A | N/A | F | A | A | A | | | | | | |
| IPAC | | F | A | A | A | A | A | A | A | | | | | |
| MTBE | | A | A | A | A | A | A | A | A | A | | | | |
| MEK | | A | A | A | A | A | F | A | A | A | A | | | |
| DCM | | A | A | A | A | A | A | A | A | A | A | A | | |
| Toluene | | A | A | A | A | A | A | A | A | A | A | A | A | |
| MIBK | | C | A | A | A | A | A | A | A | A | A | A | A | A |

Salt Formation Experiments

In order to screen conditions other than slurry experiments, salt formation (reactive crystallization) experiments in 12 solvents were carried out. The procedure of the experiments was shown below.

150 mg free base was added in a 4 ml vial with magnetic stirrer 10 vol (1.5 ml) solvents (the list of the solvents are shown in Table 4 were added The solutions were stirred at 50° C. for 2 hours 2.2 eq mol (113 mg) of the P-toluenesulfonic acid were added into the solutions at 50° C.

As soon as suspension with sufficient amount of solid (for XRPD/DSC test) were formed, samples were filter/dried and were subjected to XRPD/DSC analysis Solids with new XRPD patterns were analyzed by NMR for acid/base ratio Table 5-1 shows observations during salt formation experiments. It is noticed that the free base dissolved in the target solvents at 50° C. before counter ion addition. In all cases, the solids (potential salts) are formed almost immediately after counter ion addition. The solids at this point (immediately after salt formation) were analyzed before and after drying. Wet and dry XRPD analyses help to identify potential solvates/hydrates of the salt. In some wet solids, some deviation from pattern C was observed, however the dry solids in all solvents except in toluene generated pattern C. The major observation from the experiment is the unanimous exhibition of appearance of pattern C immediately after salt formation. It is known that pattern C eventually converts to pattern A in solvents (except in methanol).

TABLE 5-1

| observations during salt formation experiments | | | | | | | | | | | | | |
|---|---|---|---|---|---|---|---|---|---|---|---|---|---|
| | | Solvents | | | | | | | | | | | |
| Process | | THF | EtOH | MeOH | MA | IPAC | EA | MEK | Toluene | IPA | IPA (5% $H_2O$) | Acetone | Acetone (5% $H_2O$) |
| Free Base 50° C. 2 hours | | Clear | Cloudy | Cloudy | Clear | Cloudy | Clear | Clear | Cloudy | Cloudy | Cloudy | Clear | Clear |
| Add Acid | Phenomenon | Solid come out quickly | Clear soon then solid come out quickly | Clear no solid | Solid come out quickly | Clear soon then solid come out quickly | Solid come out quickly | Solid come out quickly | Clear soon then solid come out quickly | Clear soon then solid come out quickly | Clear soon then solid come out quickly | Solid come out quickly | Solid come out quickly |
| | XRD wet | N/A | C | | C + Unknown | C + Unknown | C + Unknown | C | H | C | C | C | C |
| | dry | N/A | C | | C | C | C | C | H | C | C | C | C |
| Cool to RT | 1 hour | N/A | N/A | C | N/A | N/A | N/A | N/A | N/A | N/A | N/A | N/A | N/A |
| acid-base radio (theoretical value is 6:3) | | 5.55:3 | N/A | N/A | N/A | N/A | N/A | 6:3 | 3:3 | N/A | 6:3 | N/A | N/A |

Attempt to Produce Solids with Different XRPD Patterns

Various slurry and reactive crystallization experiments generated different crystalline patterns including A, B, C, D, E, F, G and H. Previous analysis (NMR) indicated that pattern H is not a true crystalline form of the di-tosylate salt, and therefore should be dropped from the list. In order to evaluate and further analysis other solids with other XRPD patterns (A-G), attempts were made to reproduce the solids (the previous experiments showing these solids had been carried out at small scales, and the majority of the solids had been consumed for XRPD/DSC analysis). Table 6-1 shows the experiment with the objective of producing solids with XRPD patterns B, C, D, E, and F. Solids with pattern A was the starting material, therefore it was already available.

TABLE 6-1

Results of preparation of Form B, C, D, E and F

| Target Form | Solvent | Condition | Time 1 day | 3 days | 5 days |
|---|---|---|---|---|---|
| B | >10 vol water | RT | | G | |
| | | 50° C. | | | |
| | | RT − seed | | | |
| | | 50° C. + seed | | G | N/A |
| | <10 vol water | RT | B | N/A | |
| | | 50° C. | G | | |
| C | MeOH | RT | N/A | C | |
| D | acetone | RT | | A | |
| | IPA | | | | |
| | EtOH | | | | |
| | MeCN | RT | | | |
| | | 50° C. | | | |
| E | MEK | RT | | | |
| | | 50° C. | A | E | A |
| F | EtOH + MeCN | RT | | A | |
| | Water + EtOH | | G | | F |
| | MA + MeCN | | F | | N/A |
| | EA + MeCN | | | A | |

Analysis Various Forms

Figure 6:
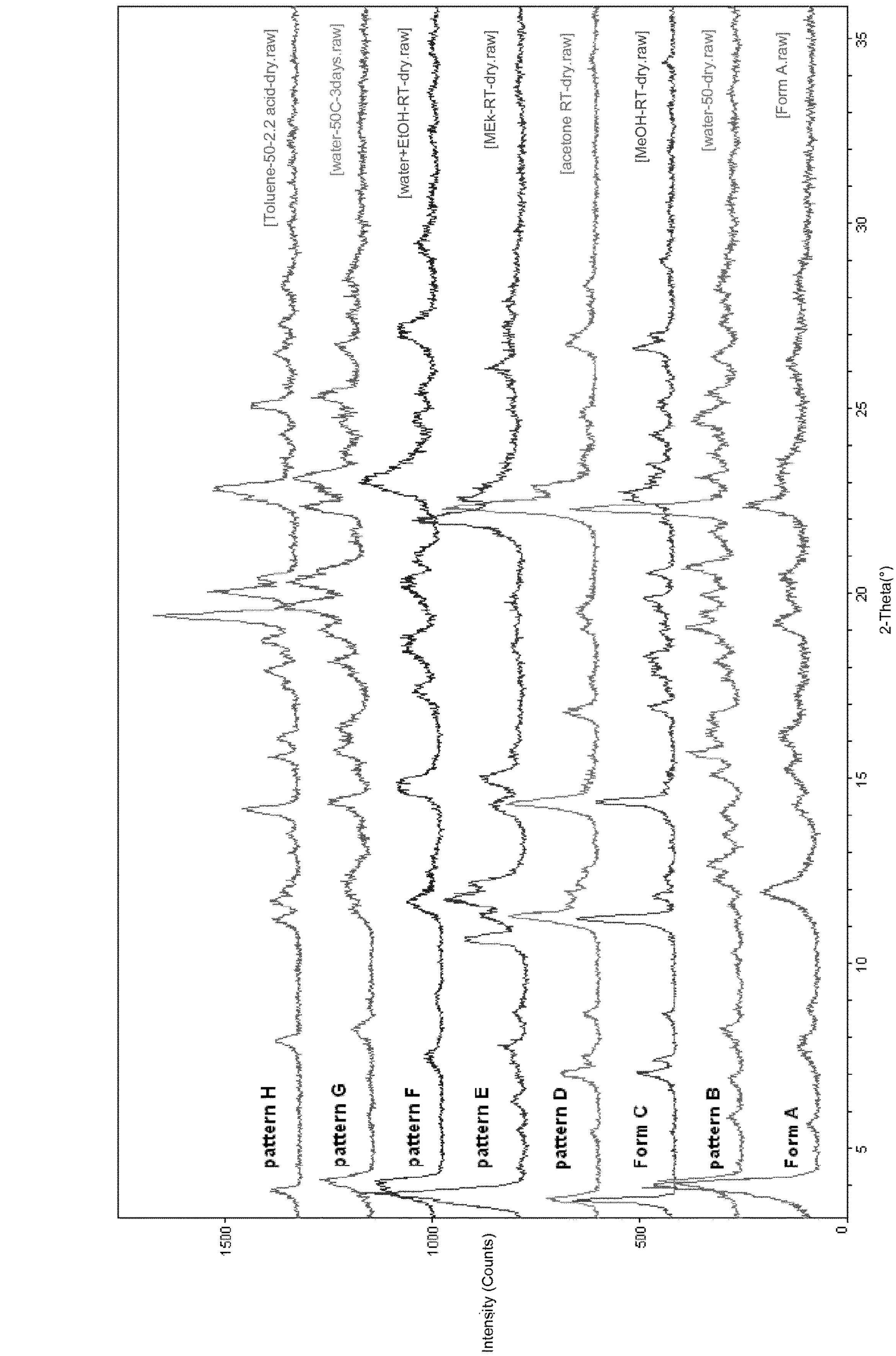
FIG. 6 shows XRPD scans of the different obtained forms described further below.

FIG. 6 shows the overlay of scans of various XRPD patterns observed in this study. Patterns A and C are true crystalline polymorphs of di-tosylate salt. Therefore the present inventors refer to this solids as Forms A and Form C. However, as other XRPD patterns have not been shown to be the true polymorph of the di-tosylate salt, the present inventors refer to them as just "pattern". It is mentioned that patterns C and D are very similar, and one may refer to them as the same crystalline form.

Figure 7:
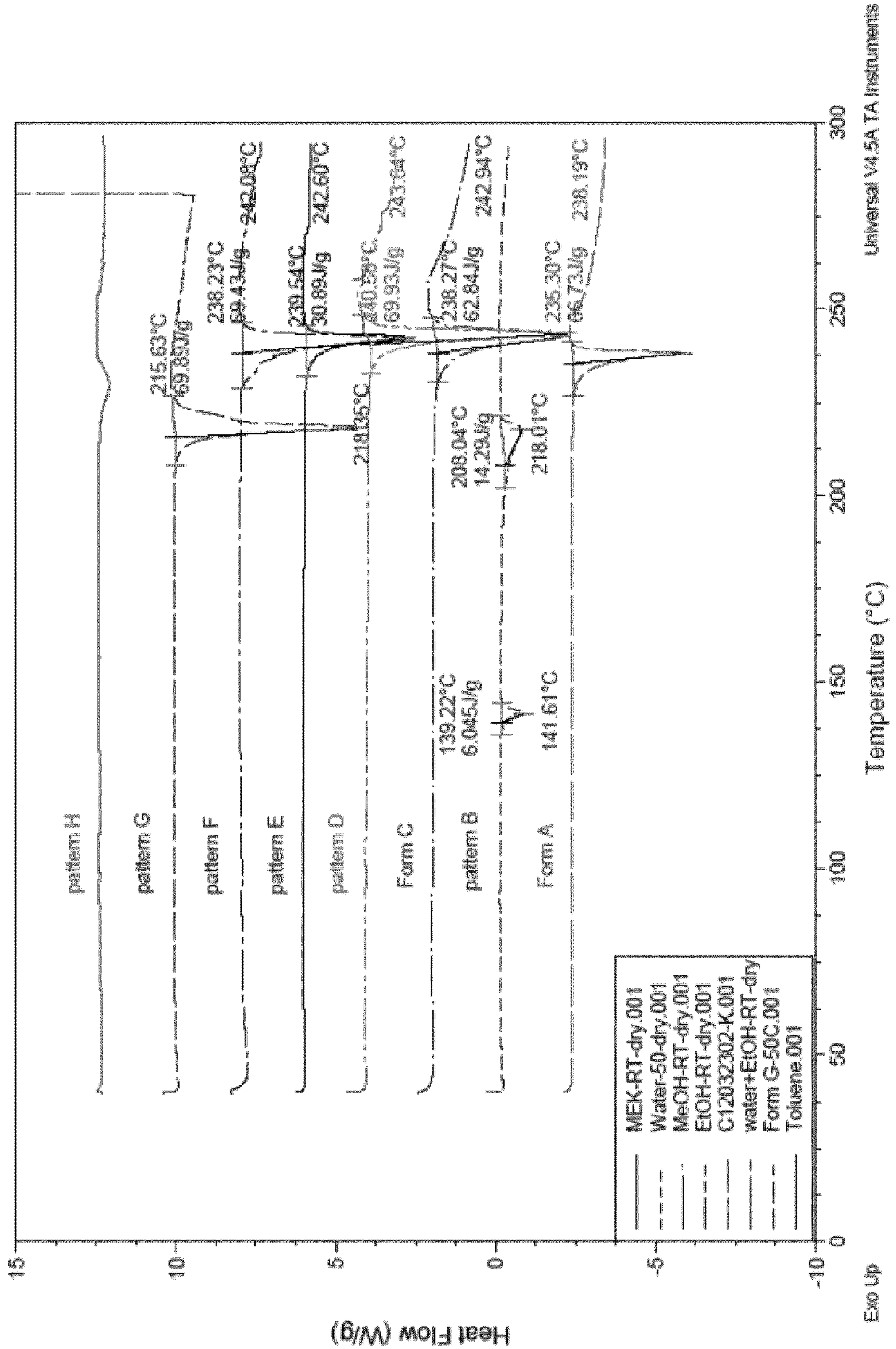
FIG. 7 shows DSC scans of the different obtained forms described further below.

FIG. 7 sketches the DSC overlay associated with various XRPD patterns of the solid. The onset temperature for Form A, C (and D), and pattern E are the same and varies between 235° C. to 240° C. Pattern B shows double endothermic peaks, one with an onset temperature around 139° C. and the other one around 208° C.

Analysis of Form A

Figure 8:
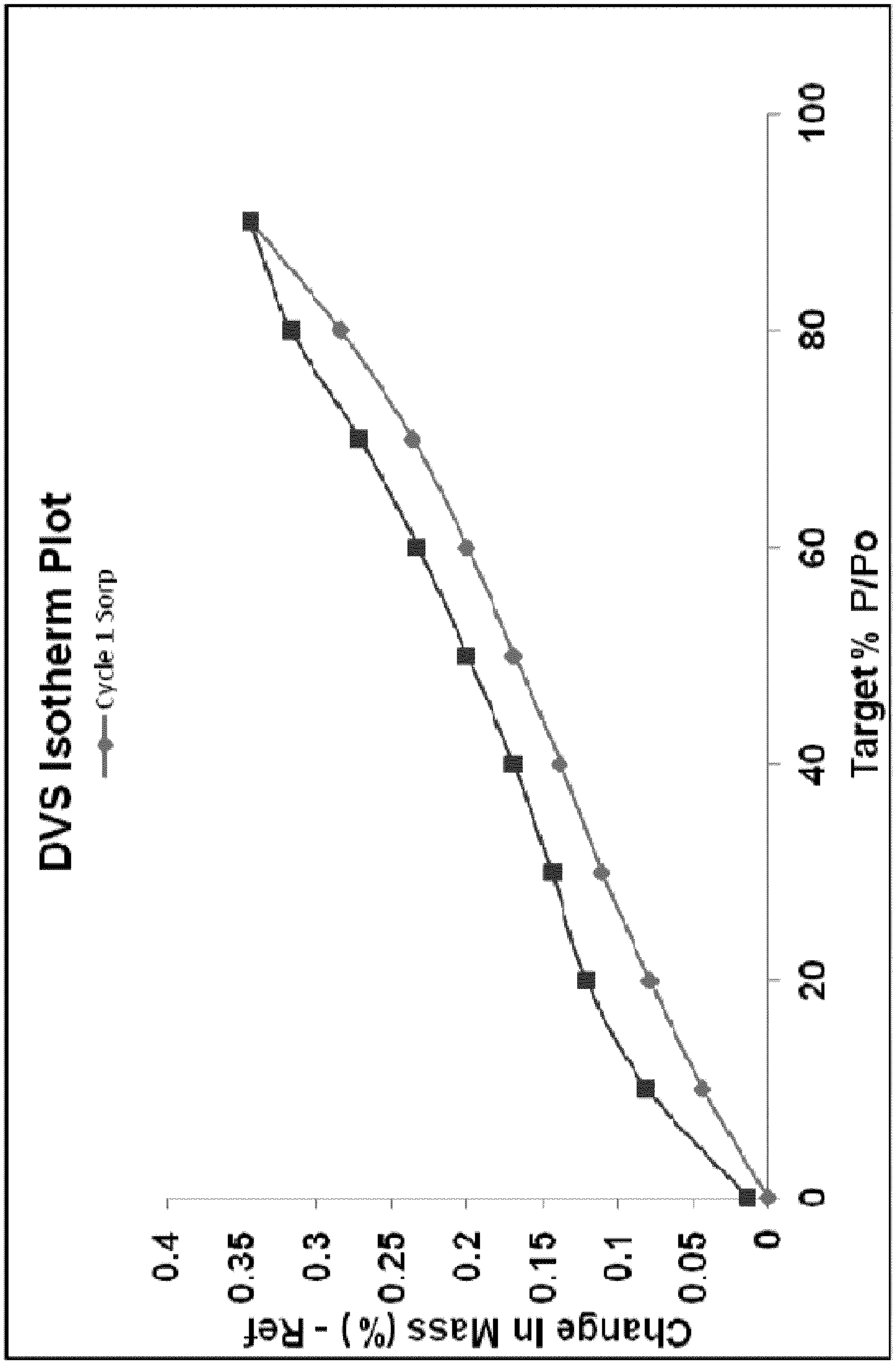
FIG. 8 shows a DVS scan of Form A.

Form A is a true polymorph of the di-tosylate salt; NMR shows the acid: base ratio is 6:3. The crystalline is generally low, the DSC scan shows a melting onset around 235° C.; the TGA scan shows 0.3% weight loss from 30° C. to 200° C. (FIGS. 4-5). It is the predominant form obtained in slurry experiments. Conversion from Form A to other XRPD patterns was mainly obtained from methanol (to Form C) or water (to pattern B) in the slurry medium. However, as it will be shown in further sections, Form C is converted to Form A upon re-slurry in the majority of other solvents (than methanol). Conversion of Form A to pattern B solids do not imply that solid with pattern B is a more stable form than Form A, since it is highly possible that pattern B is a partial (or full) hydrolyzed species of the salt. FIG. 8 shows the DVS of Form A, the water absorption is around 0.35% at 90% RH at RT.

Analysis of Form C

Figure 9:
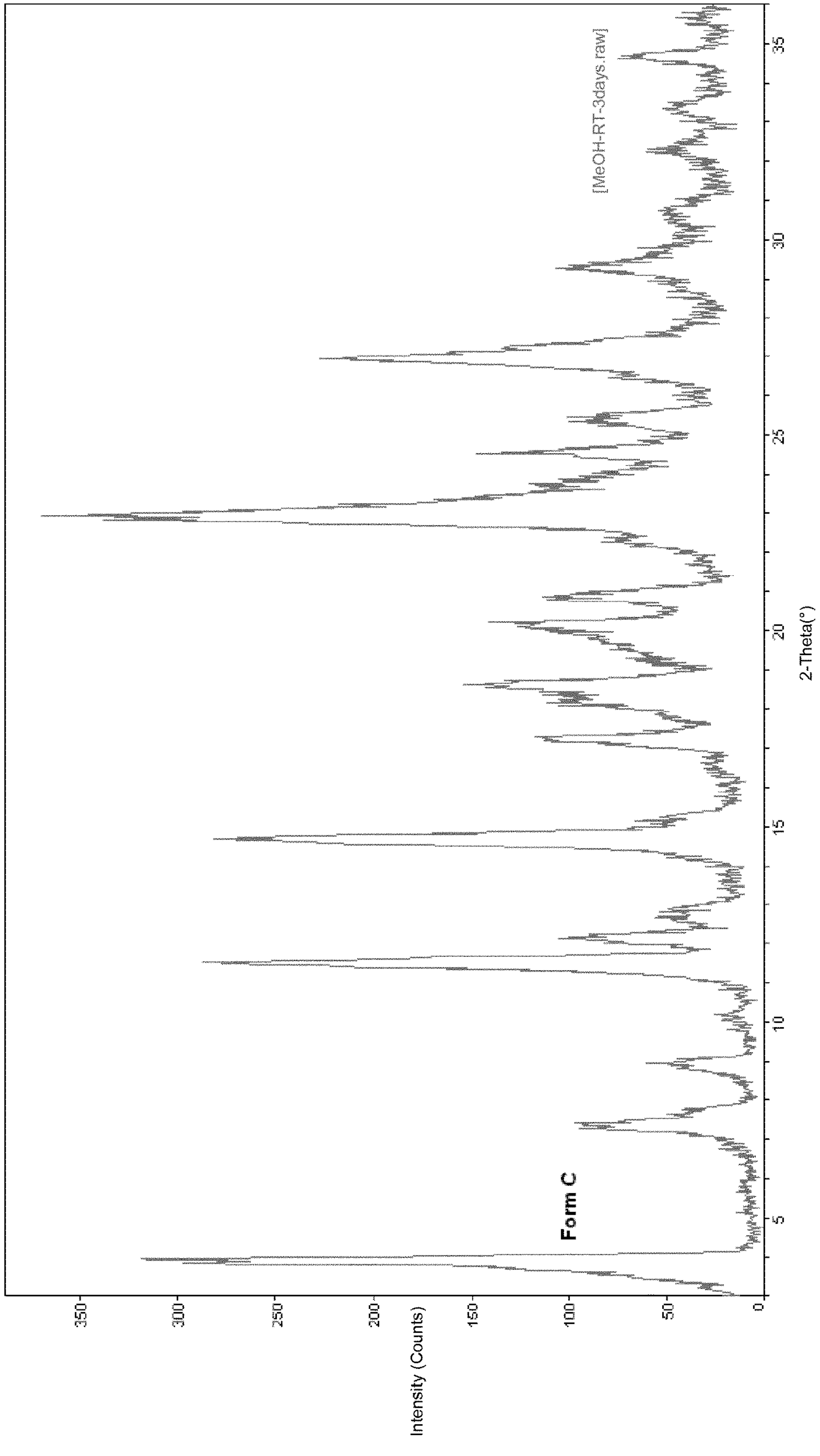
FIG. 9 shows an XRPD scan of Form C.
Figure 10:
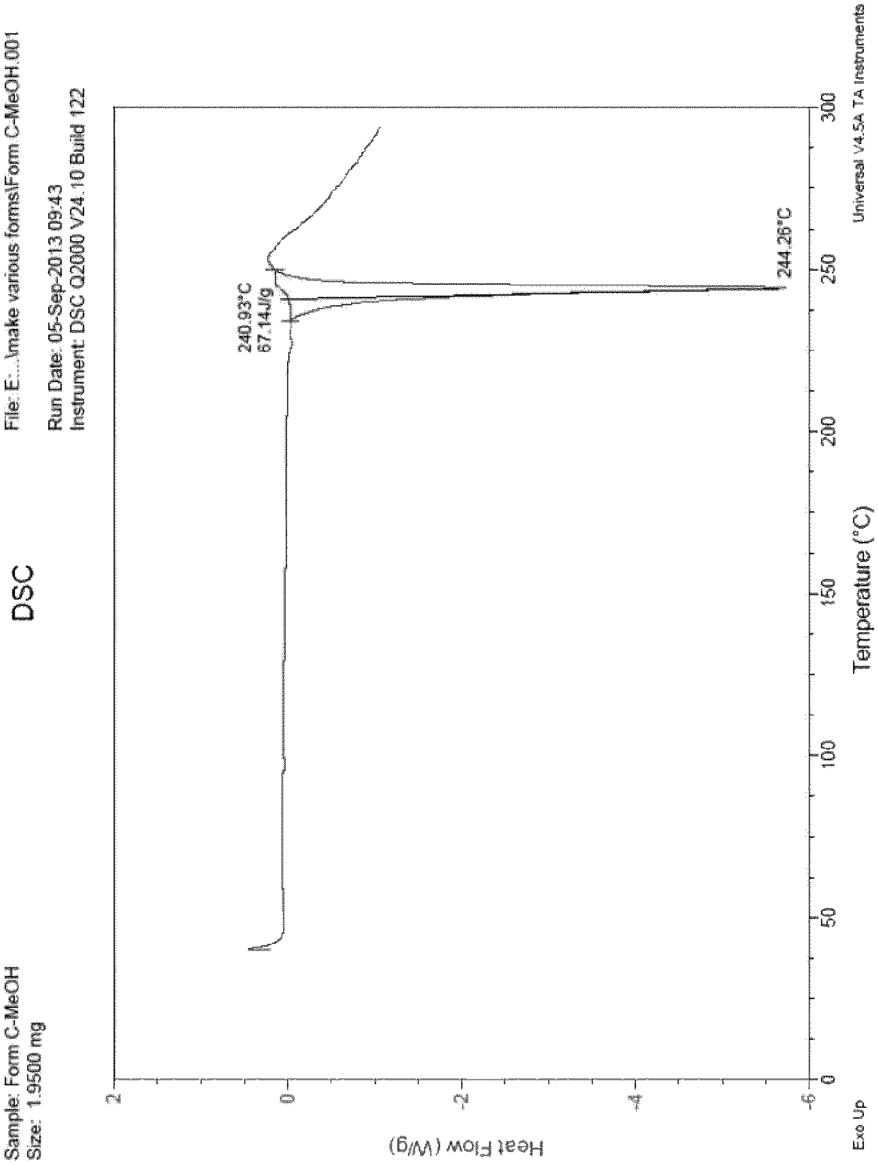
FIG. 10 shows a DSC scan of Form C.
Figure 11:
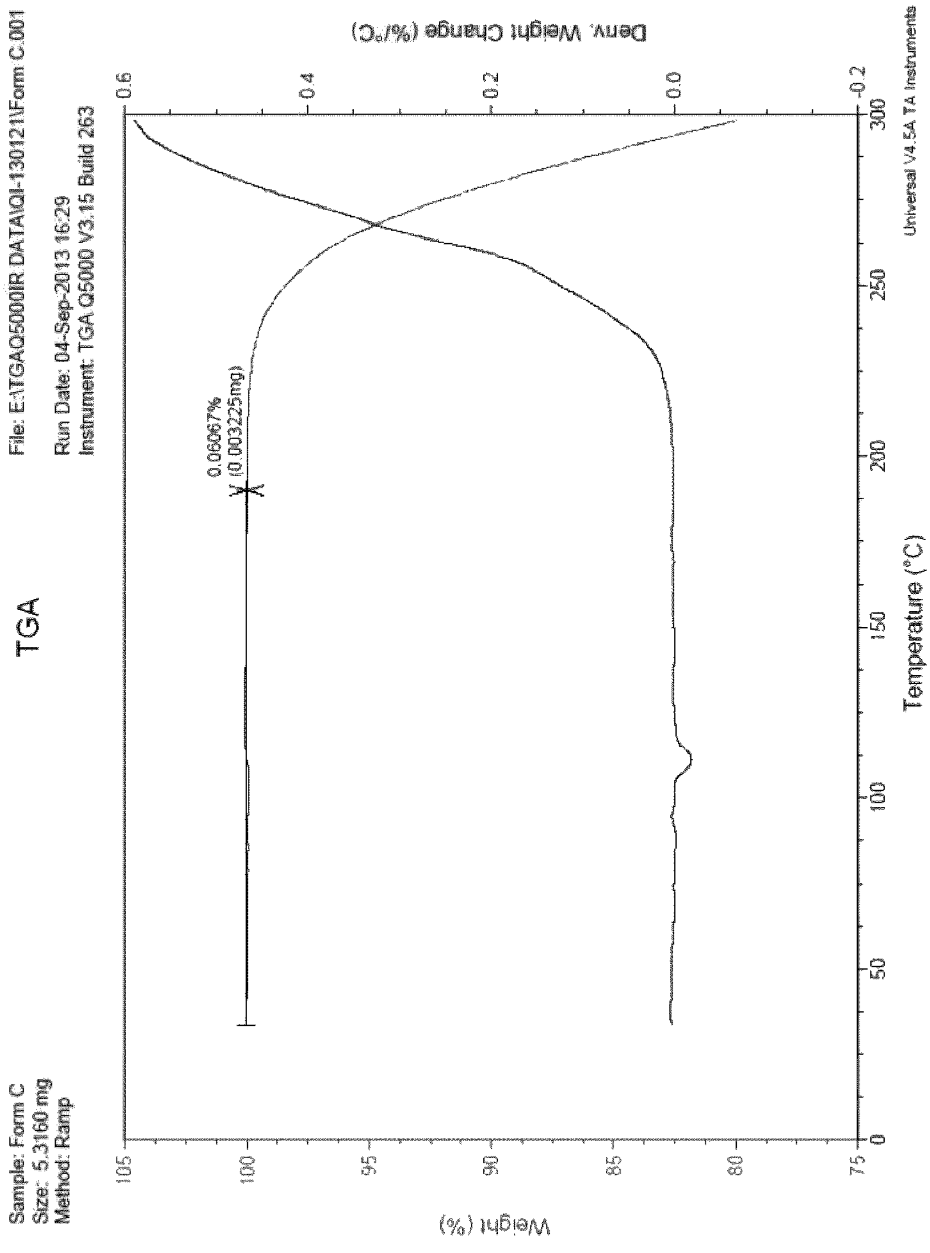
FIG. 11 shows a TGA scan of Form C.
Figure 12:
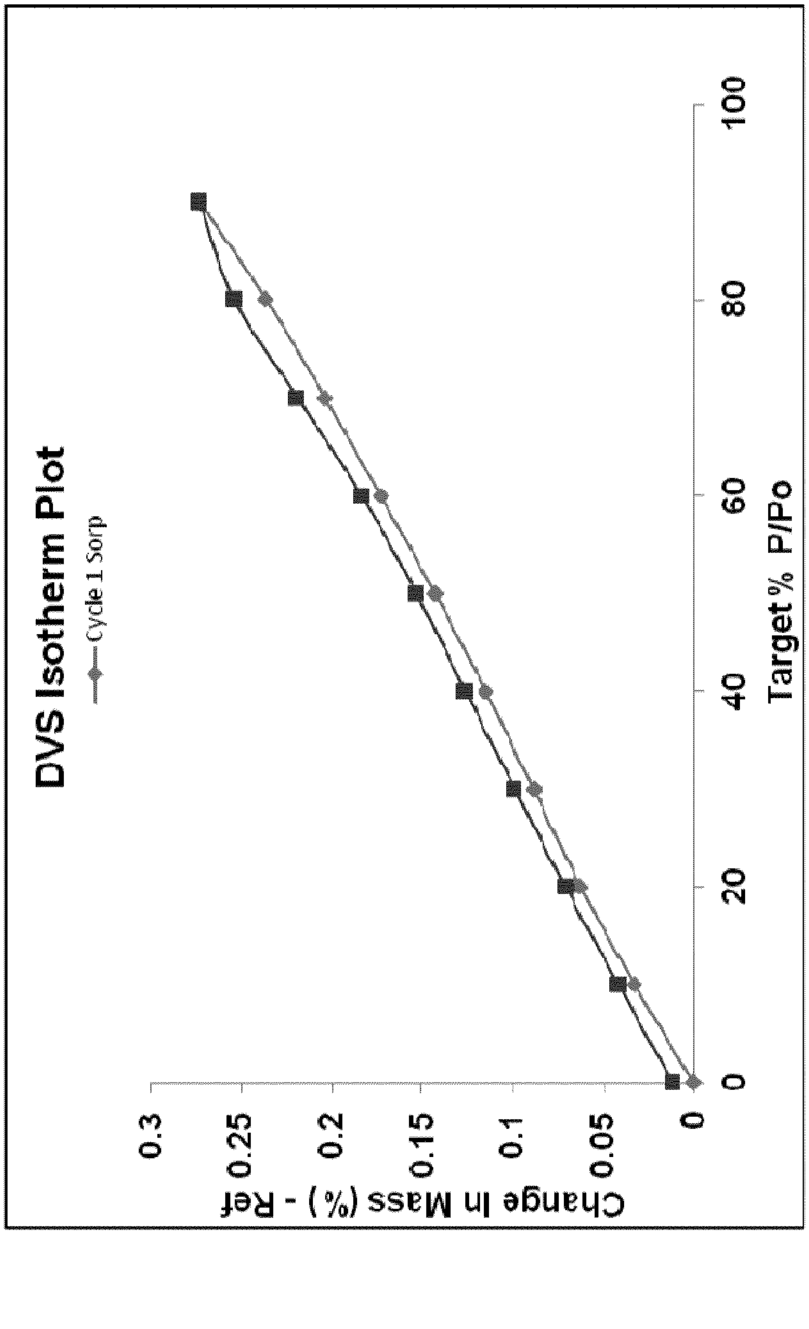
FIG. 12 shows a DVS of Form C.

FIG. 9 to 11 show XRPD, DSC, and TGA of a solid with Form C. Form C is a true polymorph of the di-tosylate salt as NMR showed the acid: base ratio is 2:1. The XRPD peaks of pattern C are sharper than those of Form A. Form C is the predominant form when methanol is used as the slurry medium. However, Form "C" is not a methanol solvate form of the di-tosylate salt. Many reactive crystallization experiments using different solvents generated Form C immediately after salt formation. Later experiments showed that overnight slurry of the same suspensions (reactive crystallization) transform Form C to A. FIG. 12 shows the DVS scan of Form C. The DVS scan shows that the solid only takes less than 0.3% water at 90% RH at RT.

Analysis of Form G

Figure 13:
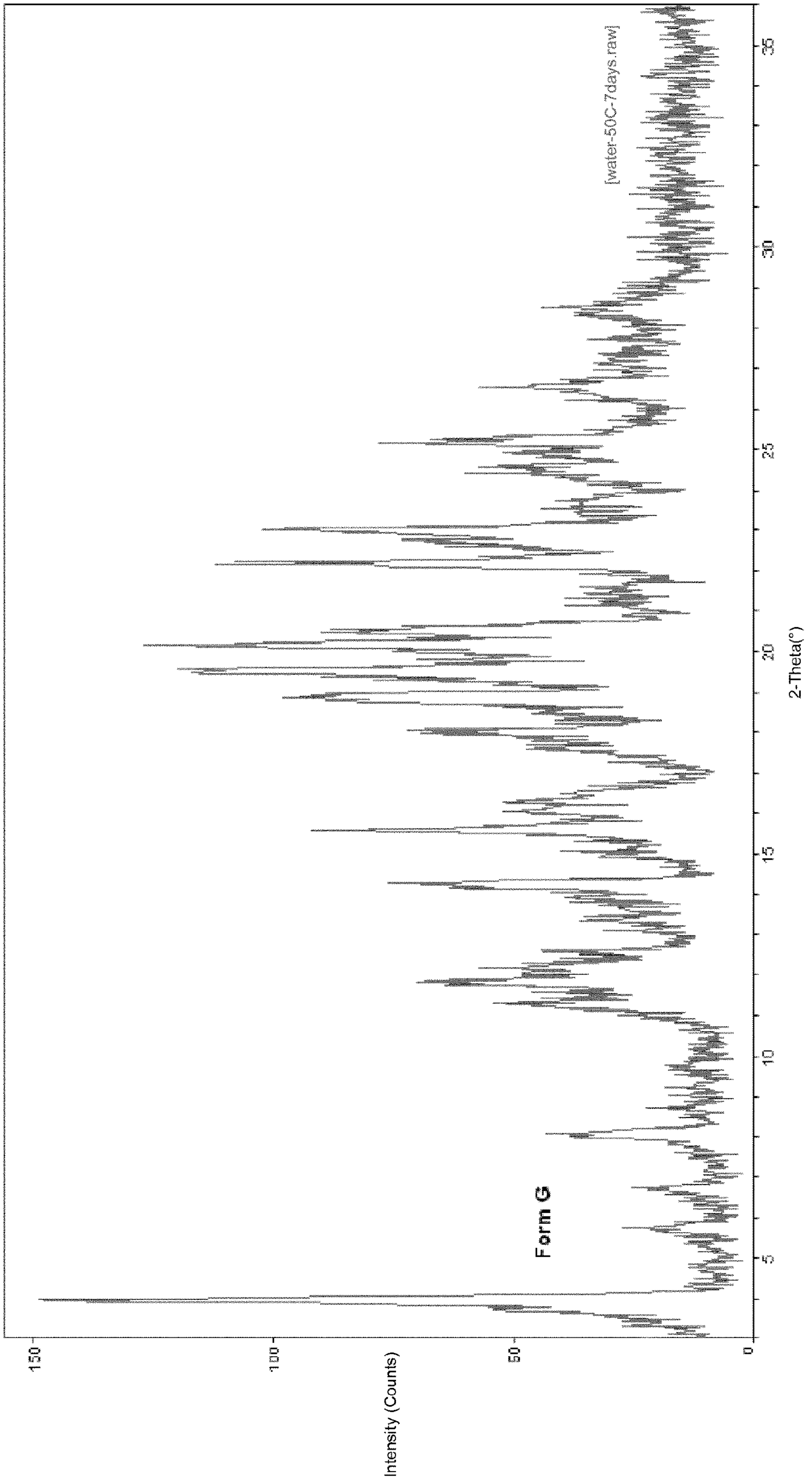
FIG. 13 shows an XRPD scan of Form G solids from slurry experiments.
Figure 14:
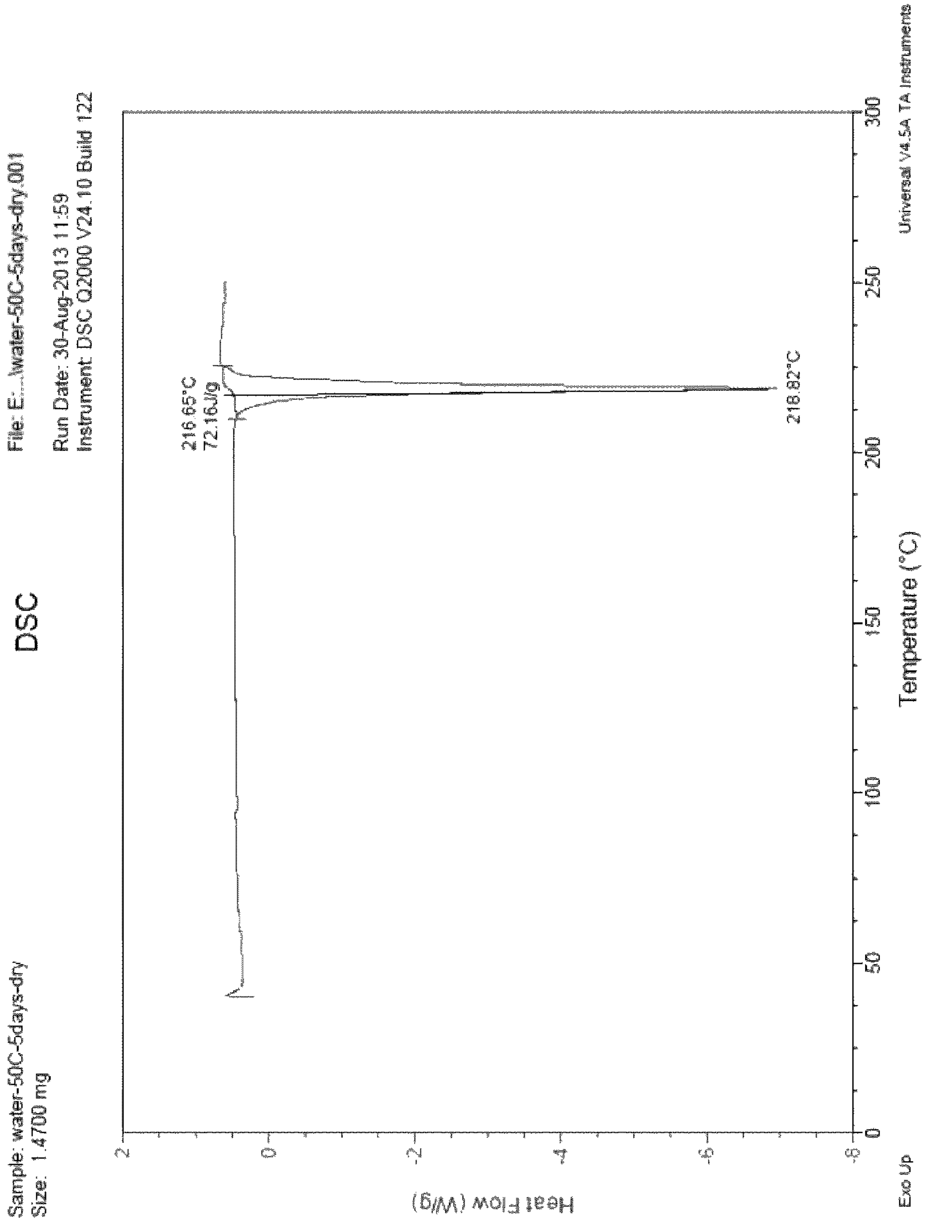
FIG. 14 shows a DSC scan of pattern G solids from slurry experiments.
Figure 15:
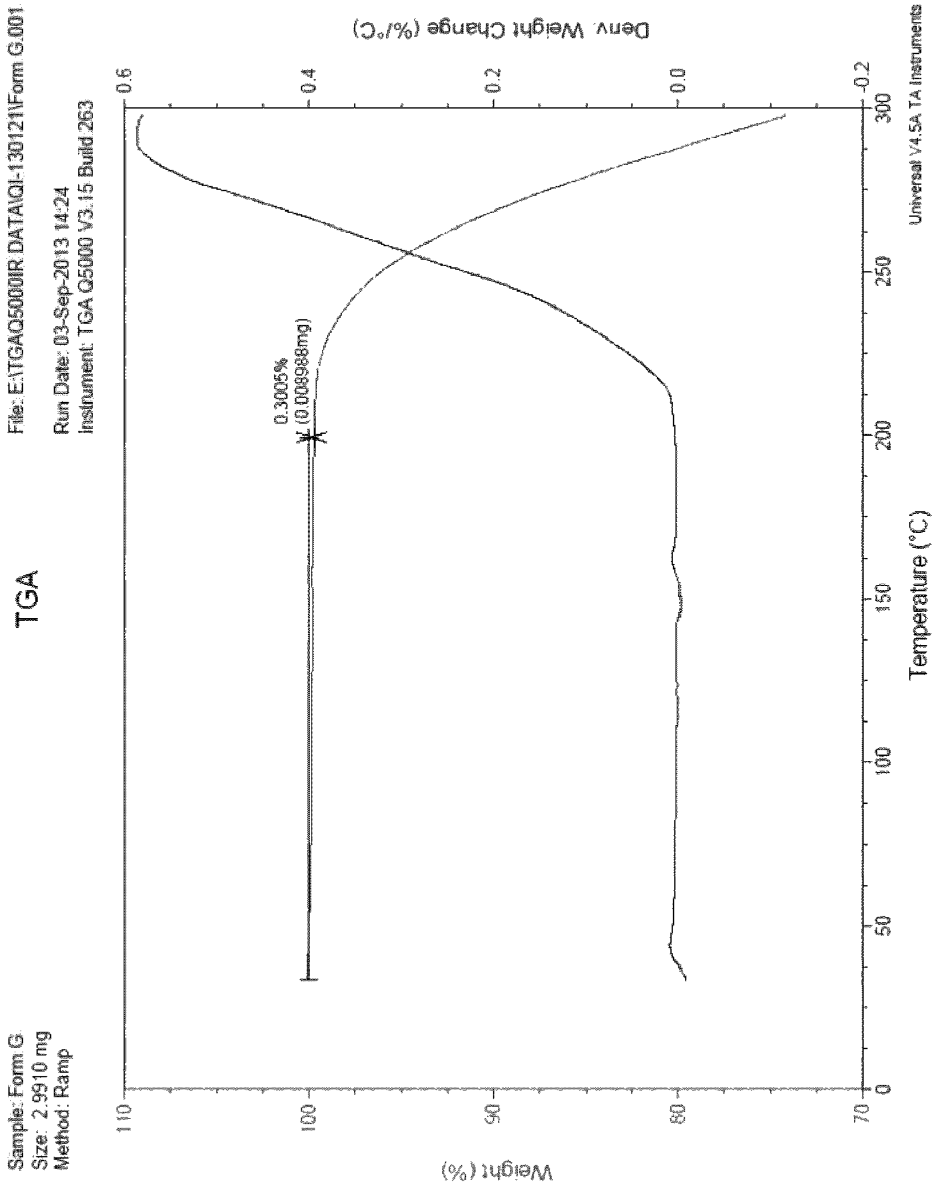
FIG. 15 shows a TGA scan of pattern G solids from slurry experiments.
Figure 16:
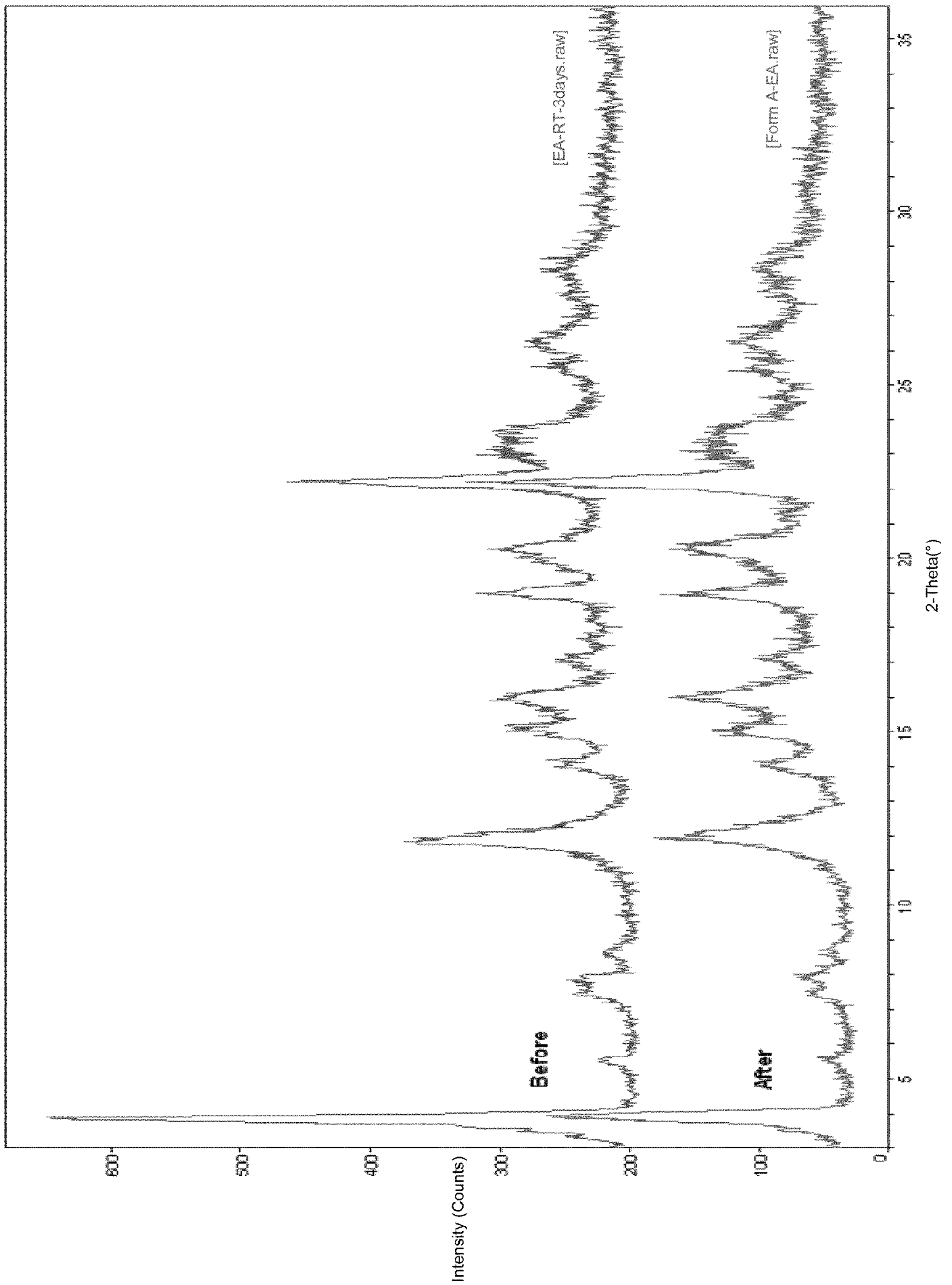
FIG. 16 shows an XRPD scan of Form A solids from 100% RH experiment.

XRPD, DSC, and TGA of a solid with pattern G are shown in FIGS. 13 to 15. The solid is crystalline, it shows a DSC melting onset of 216° C. (lower than those of Form A and C), exhibited weight loss of 0.3% in the range of 30° C.-200° C. The HPLC data shows the acid to base ratio to be 3.45:1, therefore it is not considered to be the di-tosylate salt.

Other Patterns

The efforts made to reproduce other XRPD patterns did not generate these patterns, meaning that these solids were only observed once or twice during form screening. Among these pattern B is significant, because it may point to a hydrate form. However, it is probably a hydrated form of the hydrolyzed salt, not the di-tosylate salt (hydrate of partial salt).

Stability Experiments

The objective of the work in this section is to observe the potential transformation of these forms when exposed to 100% RH as well as to identify the most stable polymorph observed in this study.

Exp 1: Exposing Forms a and C in 100% RH Experiment at RT for 6 Days

Forms A and C were exposed in 100% RH environment at RT for 6 days; the solids were subsequently analyzed using DSC and XRPD.

Figure 17:
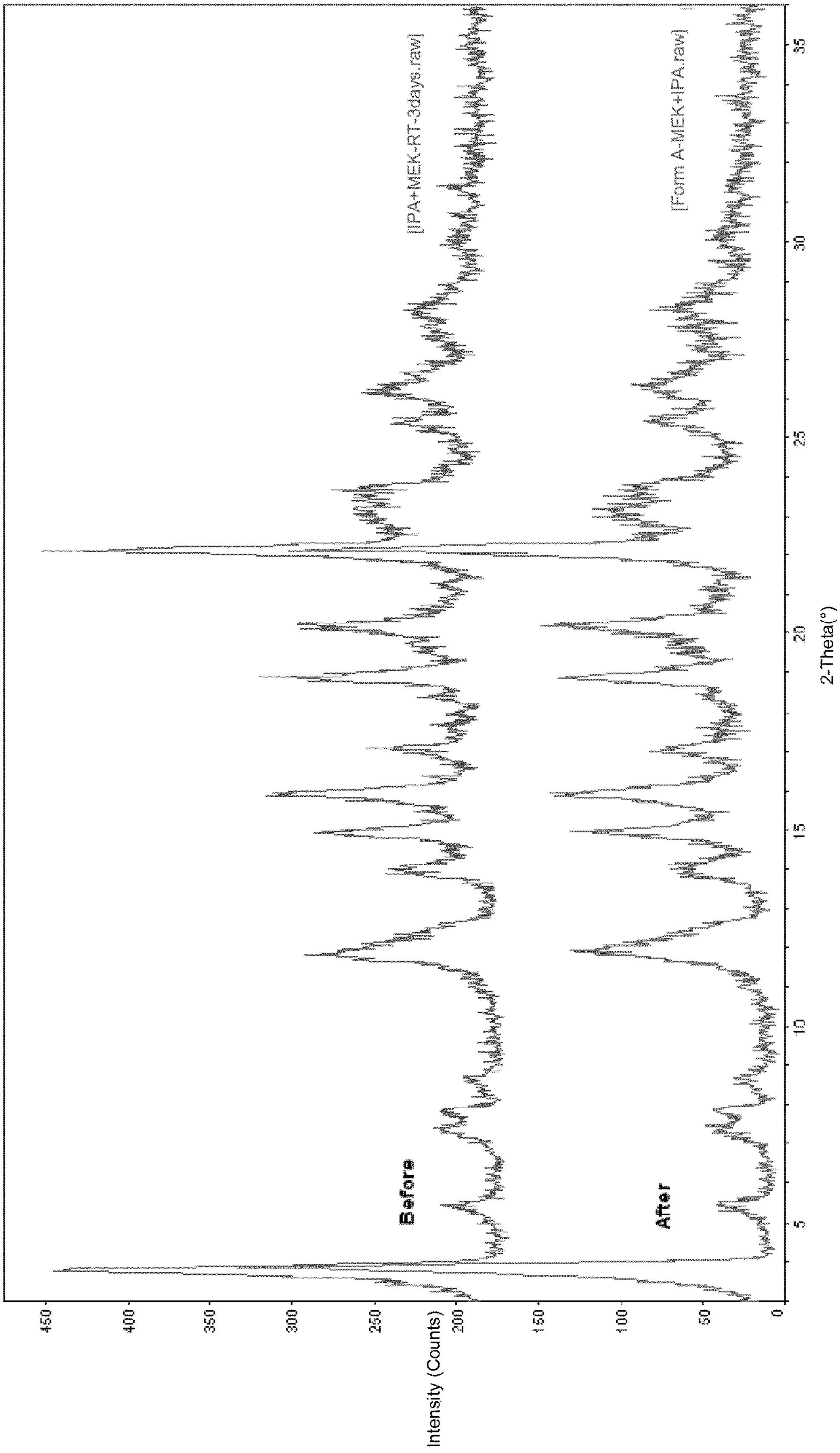
FIG. 17 shows an XRPD scan of Form A solids from 100% RH experiment.
Figure 18:
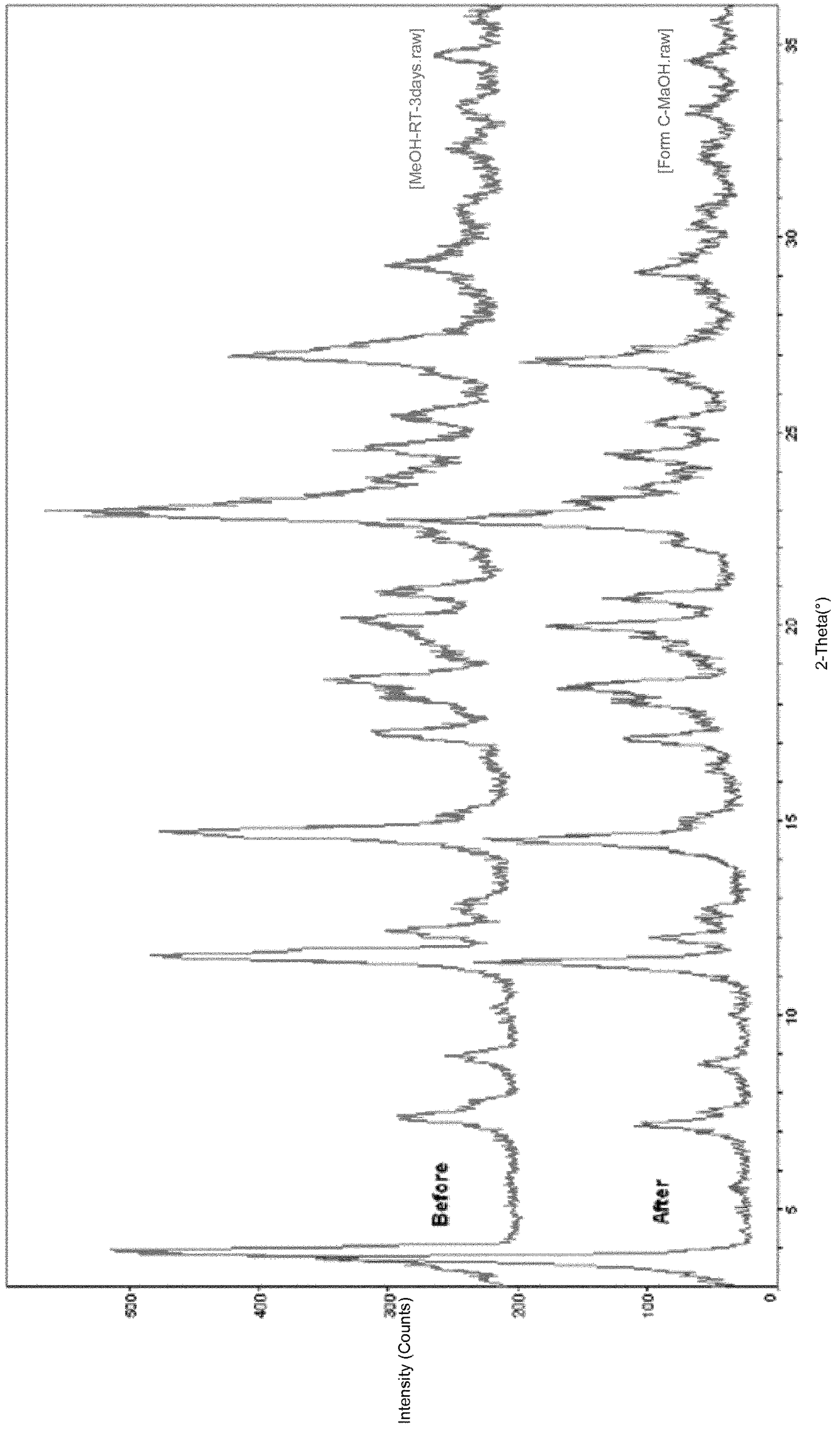
FIG. 18 shows an XRPD scan of Form C solids from 100% RH experiment.
Figure 19:
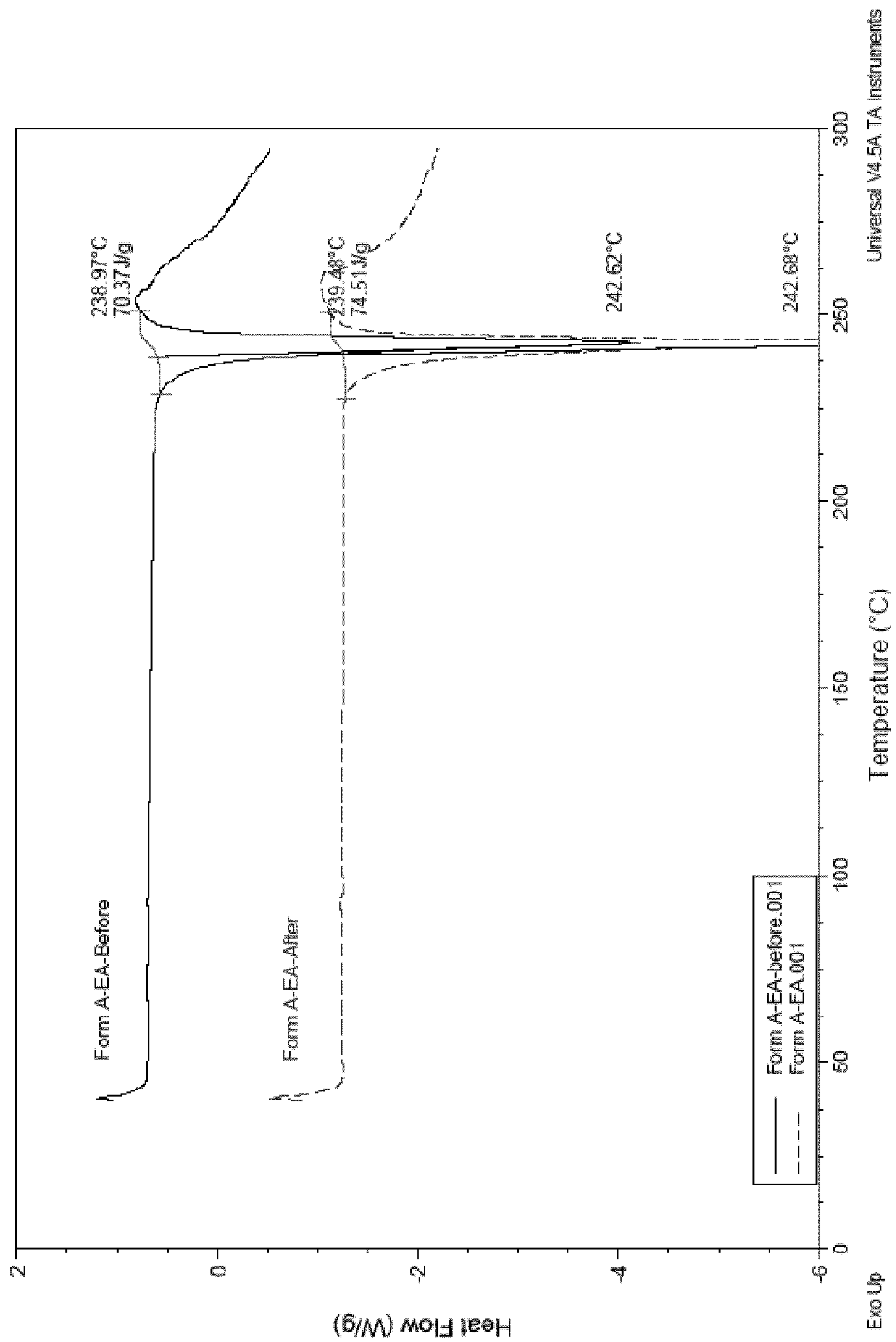
FIG. 19 shows DSC scans of Form A solids from 100% RH experiment.
Figure 20:
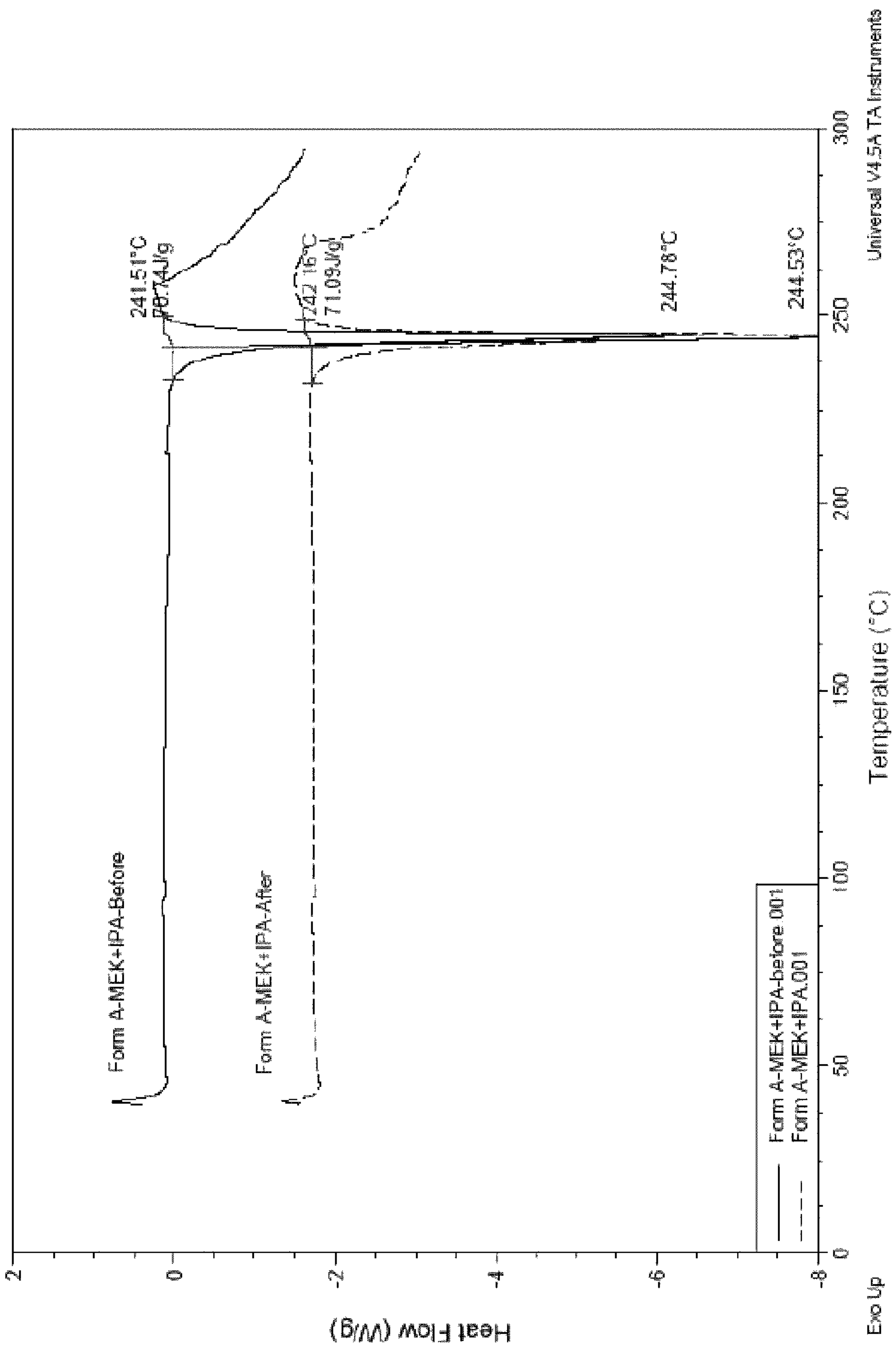
FIG. 20 shows DSC scan of Form A solids from 100% RH experiment.
Figure 21:
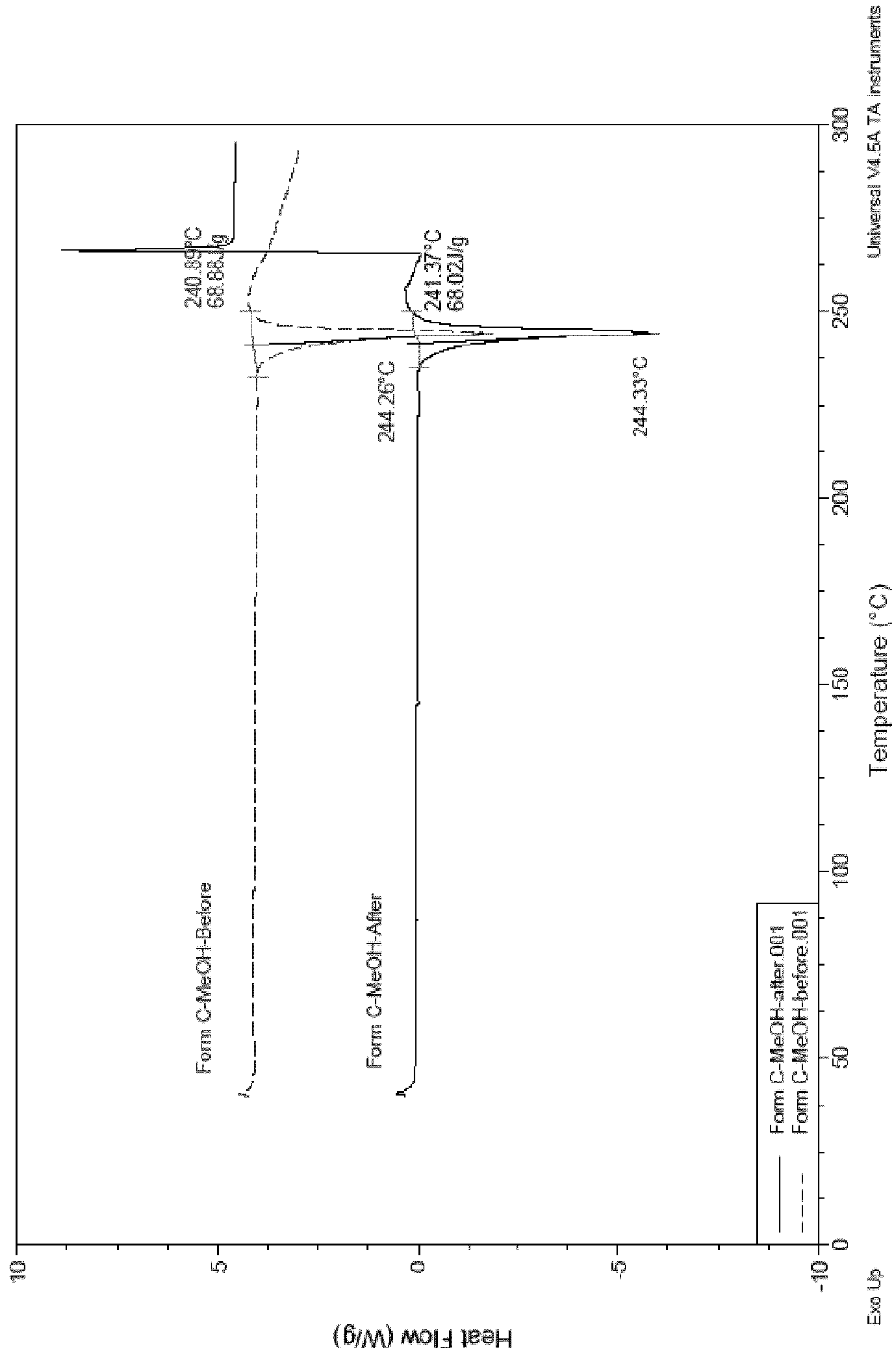
FIG. 21 shows DSC scans of From C solids from 100% RH experiment.

The results were shown in FIG. 16 to 21. In FIGS. 1 and 17, the XRPD of sample of Form A (previous obtained form EA and IPA/MEK) before and after 6 days exposure to 100% RH are sketched. FIGS. 19 and 20 show the DSC scan of the same samples after exposure. Both figures indicated no change to crystalline, shows Form A is stable (from polymorph point view) in high RH environment. FIGS. 18 and 21 show the result of the same treatment for Form C. The results show that the crystal structure does not change as a result of exposure to high RH.

Exp 2: Forms A and C Re-Slurry in 6 Different Pure Solvents at RT for 5 Days (Aging Experiments)

These experiments were performed to investigate potential transformation between Form A and C. The procedure of the experiments is shown below.

15 mg Form A and 15 mg Form C were add into a 1.5 ml vial with magnetic stirrer.

20 vol (600 ul) of various solvents was added into the vial

The suspensions were stir at RT for 5 days

Then filter and the solid was sent for XRPD (before and after drying in oven) and DSC The experimental data are shown in Table 10-1. Water, methanol, IPA, acetone, and THF were used as the slurry medium. The data from day 5 samples indicated partial hydrolysis of the di-tosylate salt in water (producing pattern G solid). One more times methanol as the slurry medium produced Form C, which is consistent with previous re-slurry findings. These data indicate that Form A is more stable than Form C (except in methanol) and thus appears to be the most stable form under most conditions.

TABLE 10-1

Results of Forms A and C re-slurry in 6 different pure solvents at RT for 5 days

| | RT | | | |
|---|---|---|---|---|
| | 4 days | | 5 days | |
| Solvents | wet | dry | wet | dry |
| Water | G | G | G | G |
| MeOH | C | C | C | C |
| EtOH | A | A | A | A |
| IPA | Unknown | A | A | A |
| THF | A | A | A | A |

Exp 3: Forms A, C, and H Re-Slurry in 6 Different Pure Solvents at RT and 50° C. For 3 Days The procedures for those experiments were shown below.

10 mg Form A and 5 mg Form C were added into a 1.5 ml vial with magnetic stirrer.

20 vol (300 ul) of various solvents was added into the vial and it was ensured that the solution was cloudy Add little Form H as seed The suspensions were stirred at RT for 3 days Then filter and the solid was sent for XRPD (after drying in oven) and DSC The results are shown in Table 11-1 except for water (partial hydrate) and methanol (From C), other treatment at both temperatures give Form A (as expected).

TABLE 11-1 results of the stability experiments of Forms A, C, and H

| | Form | |
|---|---|---|
| solvents | RT | 50° C. |
| IPA | A | A |
| THF | A | A |
| acetone | A | A |

TABLE 11-1-continued results of the stability experiments of Forms A, C, and H

| | Form | |
|---|---|---|
| solvents | RT | 50° C. |
| MeOH | C | N/A |
| EtOH | A | A |
| water | H | H |

Exp 4: the Stability of Form C Through Seeding Experiments

Salt formation screening (reactive crystallization experiments) produced Form C. To evaluate the polymorph stability of Form C, a small amount of Form A was added into the suspensions of Form C (in the below solvents) and stirred overnight at RT. The suspensions were filtered and the solids were analyzed using XRPD (wet and dry sample). The results are shown below. The data indicate that Form C converts to Form A in all solid, confirming previous results on stability of Form A.

TABLE 12-1 results of the stability experiments

| | RT | |
|---|---|---|
| solvents | Wet(overnight) | Dry(overnight) |
| IPA | A | A |
| IPA + 5% water | A | A |
| MEK | A | A |
| MA | A | A |
| Acetone | A | A |
| Acetone + 5% water | A | A |

Example 2

Inventors wanted to perform a salt/co-crystal screen of Q203 free base, shown below. To this end, a standard salt/co-crystal screen of Q203 was carried out in order to identify salts with acceptable properties and also physico-chemical characterisation of Q203 free base was conducted. The starting material used in this example 2 were Q203 free base, batch C12032302-J16001 and a ditosylate salt of Q203, batch C12032302-K16001M.

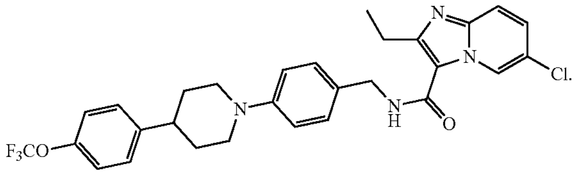 [SMILES: CCc1nc2ccc(Cl)cn2c1C(=O)NCc1ccc(N2CCC(c3ccc(OC(F)(F)F)cc3)CC2)cc1]

Chemical Formula: $C_{29}H_{28}ClF_3N_4O_2$

Molecular Weight: 557.01

Elemental Analysis: C, 62.53; H, 5.07; Cl, 6.36; F, 10.23; N, 10.06; O, 5.74

Q203 free base chemical structure

The following co-formers, listed in Table 1, have been used for the salt/co-crystal of Q203 free base:

TABLE 1

| List of co-formers used in this example 2<br>Co-formers | | | | |
|---|---|---|---|---|
| 2-furoic acid | isethionic (2-hydroxy-ethanesulfonic) acid | pamoic acid | hydriodic acid | oxalic acid |
| ascorbic acid | ketoglutaric (oxoglutaric) acid | phosphoric acid | hydrochloric acid | nitric acid |
| citric acid | lactobionic acid | p-toluenesulfonic acid | glycolic (hydroxyacetic) acid | naphtalene-2-sulfonic acid |
| estolic (laurylsulfonic) acid | maleic acid | pyroglutamic (L) acid | glucoheptonic acid | mono-methyl ester of sulfonic acid |
| ethane-1,2-disulfonic acid | malic (L) acid | pyruvic (2-oxopropanoic) acid | glucaric (saccharic) acid | methanesulfonic acid |
| fumaric acid | malonic acid | saccharin | gentisic (2,5-dihydroxybenzoic) acid | mandelic acid |
| gluconic acid | tartaric (L) acid | mucic acid | urea | sulphuric acid |
| succinic acid | salicylic acid | — | — | — |

2 Experimental

2.1 Solubility Estimation

Aliquots of the test solvent were added to an accurately weighed sample (~25 mg) of Q203 batch C12032302-J16001 at ambient temperature. The aliquot volumes were typically 50-100 μL. Complete dissolution of the test material was determined by visual inspection. The solubility was estimated from these experiments based on the total solvent used to provide complete dissolution. It should be noted that the actual solubility may be greater than that calculated because of the use of solvent aliquots that were too large or due to a slow rate of dissolution.

If dissolution did not occur after the last aliquot of solvent was added (typically ~40 volumes of solvent), the sample was subjected to two cycles of the following temperature cycling regime on the Clarity crystallisation station:

Heat from 20° C. to within 3° C. of solvent boiling point (or 100° C., whichever was lower) at 0.5° C./minute.

Cool to 20° C. at 0.2° C./minute.

Stirrer speed 800 rpm.

From the infrared (IR) transmission data of the sample vials, dissolution and precipitation events were recorded as the point of complete transmission of IR and the onset of turbidity by IR respectively. The solubility values for Q203 were expressed as a range and rounded to the nearest whole number.

2.2 Screening Methods

Experiments were carried out at a scale of ~25 mg with 1:1 stoichiometry and 2:1 stoichiometry (salt/co-crystal former: Q203 free base).

2.2.1 Slow Evaporation

A stock solution of coformer in a chosen solvent (1 eq.) was added to a stock solution of Q203 free base (Batch C12032302-J16001, 1 or 2 eq.). Where stock solutions of the coformer were not made, the coformer was added as a solid/liquid. The resultant solution was evaporated in a fume hood at ambient temperature in a vial covered with perforated aluminium foil. Isolated solids were dried under nitrogen then analysed by XRPD.

2.2.2 Slurry Experiments

Q203 free base (Batch C12032302-J16001, 1 eq.) and coformer (1 or 2 eq.) was added to a given solvent until undissolved solids remained at the desired temperature (20 or 40° C.). The vial was sealed and the slurry was maintained at the selected temperature and agitated by magnetic stirring for 5-7 days. Solids were isolated by centrifugation and liquid decantation and dried under nitrogen prior to analysis by XRPD.

2.2.3 Sonication

A selected neat or mixed solvent system was added to Q203 free base (Batch C12032302-J16001, 1 eq) and coformer (1 eq) to form a paste. The paste was sonicated at 70% intensity using a Cole-Parmer 130W ultrasonic processor using a pulsed program. All solids recovered from these experiments were dried under nitrogen prior to analysis by XRPD.

2.2.4 Liquid Assisted Grinding (LAG)

Q203 free base (~50 mg, 1 eq.) was added to a stainless steel milling chamber with selected co-former (1 eq.). A milling ball and solvent (25 μl) was added to the chamber, which was milled for 3×2 mins @25 Hz, scraping the walls of the chamber in between each run. The grinded solid was analysed by XRPD.

2.2.5 Co-Melting (Kofler Melt)

Q203 free base (~50 mg, 1 eq.) was added to a HPLC vial with selected co-former (1 eq.). The vial was pre-purged with nitrogen and the temperature of the hotplate was increased until one solid melted and diffused into the other. The molten material was allowed to cool to ambient prior to subsequent analysis by XRPD.

2.2.6 Humidity Stress of Generated Salts

Approximately 25 mg of generated salts of Q203 were added to vials and placed unsealed into a 75% relative humidity chamber (sealed cabinets with relative humidity conditions controlled by super-saturated salt solutions) at ambient temperature for 7 days prior to analysis by XRPD.

2.3 Experimental Techniques 2.3.1 X-ray Powder Diffraction (XRPD)

XRPD analyses were performed using a Panalytical Xpert Pro diffractometer equipped with a Cu X-ray tube and a Pixcel detector system. The isothermal samples were analysed in transmission mode and held between low density polyethylene films. 2 XRPD programs were used (range 3-40° 2θ, step size 0.013°, counting time 99 sec, ~22 min run time and range 3-40° 2θ, step size 0.013°, counting time 46 sec, ~11 min run time). XRPD patterns were sorted and manipulated using HighScore Plus 2.2c software.

2.3.2 Differential Scanning Calorimetry (DSC)

DSC analyses were carried out on a Perkin Elmer Jade Differential Scanning Calorimeter. Accurately weighed samples were placed in crimped aluminium pans. Each sample was heated under nitrogen at a rate of 10° C./minute to a maximum of 300° C. Indium metal was used as the calibration standard. Temperatures were reported at the transition onset to the nearest 0.01 degree. Note that DSC traces within this report may contain automated peak integrations which calculate ΔH of fusion. Where multiple thermal events are observed at similar temperatures, these ΔH values are prone to significant error.

2.3.3 Thermogravimetric Differential Thermal Analysis (TG/DTA)

Thermogravimetric analyses were carried out on a Mettler Toledo TGA/DSC1 STARe. The calibration standards were indium and tin. Samples were placed in an aluminium sample pan, inserted into the TG furnace and accurately weighed. The heat flow signal was stabilised for one minute at 25° C., prior to heating to 300° C. in a stream of nitrogen at a rate of 10° C./minute.

2.3.4 $^1H/^{13}C$ Nuclear Magnetic Resonance spectroscopy (NMR)

NMR analysis was carried out on a Bruker 500 MHz instrument in MeOD-$d_4$ or DMSO-$d_6$. Instrumental parameters are listed on the relevant spectrum plots.

2.3.5 Optical Microscopy

Microscopy analyses were carried out using an Olympus BX51 stereomicroscope with crossed-polarised light and a 1st order red compensator plate. Photomicrographic images were captured using a ColorView IIIu digital camera and SynchronizIR basic V5.0 imaging software with objective lens magnification of ×10.

2.3.6 HPLC

HPLC was used to determine equilibrium solubility in a variety of solvents. Samples in solvents that were immiscible with water were evaporated to dryness and re-dissolved in sample diluent.

2.3.7 Solubility Determination

To determine the solubility suspensions of Q203 salts (p-TSA, phosphate & HCl) in the chosen pH conditions (1, 4.5, 6.8 & 7.5), experiments were set up in duplicate. Salt was weighed into vial (~25 mg) and aliquot of chosen buffer was added (1 mL). Suspension were placed on the plate and stirred at room temperature for 22-72 hours. The pH of samples were monitored during the stirring and adjusted to maintain pH within +/−0.5 pH units of the parent buffer solution. At the end of the experiment the aliquot was withdrawn at the end of the experiment and filtered through syringe PTFE filter (0.45 μm), pH was checked and the solution was injected onto the HPLC system without dilution. If results showed samples were too concentrated, samples were diluted and rerun. The solids recovered were analysed by XRPD and checked for form change.

The preparation methods for the solutions used in this study are shown below:

2.3.8 Components for Standard Buffer Solutions Preparation (According to USP 27)

2.3.8.1 Potassium Chloride 0.2M

Potassium chloride (1.5 g) was weighed into 100 mL flask and filled to the mark with water.

8.2.1.2 Monobasic Potassium Phosphate 0.2M

Monobasic potassium phosphate (2.8 g) was weighed into 100 mL flask and filled to the mark with water.

2.3.8.2 Sodium Hydroxide 0.2M

Standard solution of NaOH (2.0M, 10 mL) was added to 100 mL flask and filled to the mark with water.

2.3.8.3 Potassium Biphthalate 0.2M

Potassium biphthalate (4.1 g) was added to 100 mL flask and filled to the mark with water.

8.2.1.4 Hydrochloric Acid 0.2M

HCl Standard solution (1.0M, 20 mL) was added to 100 mL flask and filled to the mark with water.

2.3.8.4 USP Buffer pH 1

0.2M Potassium chloride solution (50 mL)+0.2M HCl solution (85 mL) was added to 200 mL flask and filled to the mark with water.

2.3.8.5 USP Buffer pH 4.5

0.2M Potassium biphthalate solution (50 mL)+0.2M NaOH solution (6.6 mL) was added to 200 mL flask and filled to the mark with water 2.3.8.6 USP Buffer pH 6.8

0.2M monobasic Potassium phosphate solution (50 mL)+ 0.2M NaOH solution (22.4 mL) was added to 200 mL flask and filled to the mark with water.

2.3.8.7 USP Buffer pH 7.5

0.2M monobasic Potassium phosphate solution (50 mL)+ 0.2M NaOH solution (39.1 mL) was added to 200 mL flask and filled to the mark with water.

Buffers were adjusted with 1.0M HCl and 2.0M NaOH to reach correct pH if necessary.

2.3.9 pKa Analysis

The sample pKas were determined using the spectrometric (UV-metric) technique. The sample was titrated in a UV-metric triple titration from pH 2.0-12.0 at concentrations of 31-23 μM, under methanol-water co-solvent conditions (the methanol mixing ratio varied from 63.9 to 46.7% w/w).

3 Characterisation and Solvent Screen on Q203

3.1 pKa Determination

For pKa determination, no precipitation of the sample from solution was observed and two pKas, with aqueous values of 3.70 t 0.06 and 4.97±0.01 determined from the spectroscopic data collected by Yasuda-Shedlovsky extrapolation of the individual results obtained (see Table 2).

It should be noted that an additional potentiometric assay was carried out which confirmed the pKas and that there were no further pKas associated with the sample within the measurable pH range (2.0-12.0).

TABLE 2 pKa results of Q203 free base

| pKa | T/° C. | Ionic environment | Method |
|---|---|---|---|
| 3.70 ± 0.06 | 25.0-25.1 | 0.15M KCl | UV-metric |
| 4.97 ± 0.01 | 25.0-25.1 | 0.15M KCl | UV-metric |

3.2 Characterisation of Q203 Free Base

Figure 22:
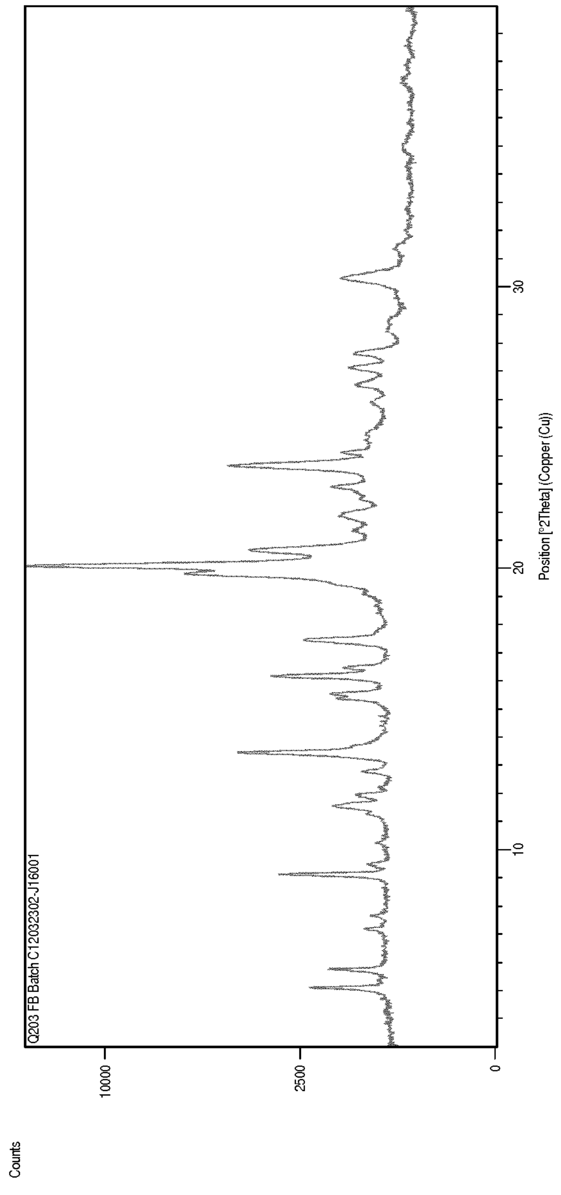
FIG. 22 shows an XRPD pattern of Q203 free base, batch C12032302-J16001.

The XRPD pattern obtained for Q203 free base batch C12032302-J16001, is shown in FIG. 22. The XRPD pattern is indicative of a highly crystalline material. Proton NMR analysis of Q203 free base showed the material conformed to the molecular structure, with a likely presence of residual solvent (potentially acetone ~80 ppm) (data not shown).

3.3 Characterisation of Q203 Ditoyslate Salt

Figure 23:
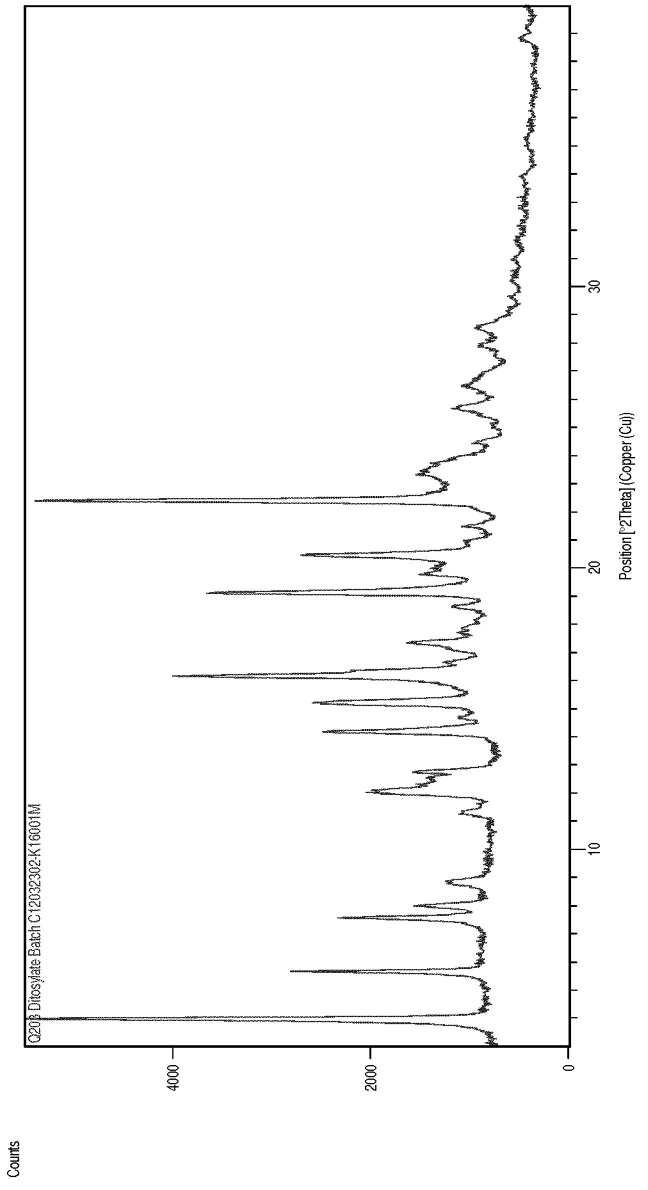
FIG. 23 shows XRPD pattern of Q203 ditosylate, batch C12032302-K16001M, form A (i. e proper "Q203" ditosylate).

The XRPD pattern obtained for Q203 ditosylate batch C12032302-K16001M, is shown in FIG. 23 (Form A or "pattern A"). The XRPD pattern is indicative of a crystalline material, with a slight elevation of the baseline and broadening of peaks suggesting possible amorphous content. Proton NMR analysis of Q203 ditosylate showed the material conformed to the molecular structure with a 2:1 acid/API stoichiometry (data not shown).

3.4 Estimated Solubility of Q203 Free Base

The solubility of Q203 free base was estimated in 10 solvent systems using the aliquot addition method. Temperature cycling experiments were also performed using the Clarity crystallisation station in order to assess the solubility of the compound with heating. The solubility data are detailed in Table 3. Observations recorded for each experiment are described in Table 3. Q203 free base was found in 4 solvents at room temperature at ~25 mg/mL and in further 4 other solvents upon heating. It was shown no dissolution upon temperature in acetone and MTBE.

TABLE 3

Solubility estimates of Q203 free base at 20° C.

| Solvents | Acronym | Solubility range (mg/mL) | $T_{disso}$ (° C.) | $T_{cryst}$ (° C.) |
|---|---|---|---|---|
| acetone | — | <25.4 | *35 | *not observed |
| acetonitrile | ACN | <25.0 | 58.2-58.9 | 47.4-47.9 |
| dimethyl sulfoxide | DMSO | <25.5 | 53.6-54.7 | 32.8-39.3 |
| ethyl acetate | EtOAc | 34-36 | ambient | not observed |
| IPA | IPA | <25.3 | 52.5-55.7 | 37.0-39.3 |
| methanol | MeOH | <25.0 | 45.6-47.1 | 25.3-26.6 |
| MEK | MEK | 50-56 | ambient | not observed |
| methyl tert-butyl ether | MTBE | <25.6 | not observed | not observed |
| tetrahydrofuran | THF | 128-255 | ambient | not observed |
| dichloromethane | DCM | 169-253 | ambient | not observed |

*= showed partial solubility when heated however solid remained after two Clarity heat/cool cycles 3.5 Conclusions from Characterisation and Solvent Screening Q203 Free Base

- XRPD analysis indicated that Q203 free base ("free base" herein also sometimes abbreviated as "FB") batch C12032302-J16001, is indicative of a highly crystalline material.
- Proton NMR analysis of Q203 free base (data not shown) showed the material conformed to the molecular structure, with a likely presence of residual solvent (potentially acetone ~80 ppm).
- TG/DTA data showed ~0.4% of weight loss ~40° C. to 235° C. suggesting minimal moisture or solvent content, indicating Q203 free base, batch C12032302-J16001 to be an anhydrous material with some residual moisture/solvent. A second weight loss at temperatures greater than 235° C. corresponds to the initiation of decomposition of the material. A melting endotherm was observed at onset temperature 166.8° C.
- DSC analysis confirmed the TG/DTA results showing an endotherm event at temperature onset of ~167° C.
- Polarised light microscopy of Q203 free base showed the presence of individual and agglomerated particles suggesting a polydispersed PSD.
- pKA analysis showed two pKA's aqueous values of 3.70±0.06 and 4.97±0.01.

4 Salt/Co-Crystal Screening

An extended salt/cocrystal screen has been performed on Q203 using 37 co-formers, the objective of which was to find alternative salts with more desirable properties (e.g. reduced hygroscopicity, chemical stability, dissolution rate, crystallinity, physical stability, etc.).

The approach was to generate solids under a wide and diverse range of nucleation conditions, designed to mimic the process conditions and solvents used during development and formulation. A tailored, manual/semi-automated investigation conducted by experienced specialists is widely regarded as the preferred approach and has been found to perform as well as, or better, than high throughput screening while using fewer experiments[1].

[1] A. J. Alvarez, A. Singh, A. S. Myerson, "Polymorph Screening: Comparing a Semi-Automated Approach with a High Throughput Method", Crystal Growth and Design, 2009, 9, 4181-4188

All solids from the crystallisation experiments were analysed by XRPD and the resulting patterns compared to that exhibited by the starting material. Novel XRPD patterns were assigned an alphabetical descriptor in order of discovery (Type 2, Type 3 etc). Where sufficient material was available, further analysis (e.g. NMR or TGA) was conducted on solids with novel XRPD patterns to allow tentative assignment of the novel pattern as a polymorph, solvate, hydrate, degradant or mixture thereof. A summary of all the experiments performed are listed in Appendix 1, table 25, further below.

4.1 Solvent Based Screening Techniques

Solvent based experiments were performed on approximately 25-40 mg scale in glass vials or in thin walled glass capillaries. The methods employed are described in detail in section 2.2. Evaporation, slow cooling, crash cooling, crash precipitation and prolonged slurry (at ambient and elevated temperatures) mimic conditions that are likely to be encountered during process development and manufacturing. Varying the nucleation conditions in this way maximises the chance of finding new forms and also the frequency of occurrence of these forms under typical processing conditions.

4.1.1 Slow Evaporation

Slow evaporation experiments were carried out as described in section 2.2.1 and the results are shown in the Table 4. XRPD analysis of resultant solids showed 14 novel Types (pure or in mixtures) from coformers including fumaric acid (Type 4), urea (Type 5), BSA (Type 6), pTSA (Types 7 and 8), EDSA (Type 9), NDSA (Types 10 and ii), saccharin (Type 25+3), gentisic (Type 27) and salicylic acid (Type 48). Types 2 and 3 were also observed both pure and in mixtures from multiple coformers. These Types are discussed further in section 5.

TABLE 4

Screening results from slow evaporation experiments involving Q203 free base

| Salt former | Sample No. (ND-0006E-) | Solvent | Antisolvent | Acid:API (molar eq.) | Result | XRPD |
|---|---|---|---|---|---|---|
| 2-furoic | 003-01 | THF | methanol | 1:1 | solution/solid | Type 2 |
| 2-furoic | 006-01 | THF | methanol | 2:1 | solid | Type 2 + co-former |
| ascorbic | 006-02 | THF | methanol | 2:1 | solid | Type 3 + co-former |
| ascorbic | 003-02 | THF | methanol | 1:1 | solution/solid | Type 3 + co-former |
| benzenesulfonic | 003-15 | THF | acetone | 1:1 | solid | Type 3 + Type 6 |
| benzenesulfonic | 006-15 | THF | acetone | 2:1 | solid | Type 6 |
| citric | 006-03 | THF | methanol | 2:1 | gel | amorphous |
| citric | 003-03 | THF | methanol | 1:1 | solution/solid | Type 3 |
| ethane-1,2-disulfonic | 003-22 | THF | acetone | 1:1 | solid | Type 9 |
| ethane-1,2-disulfonic | 006-22 | THF | acetone | 2:1 | gel | v. disordered |
| fumaric | 003-04 | THF | methanol | 1:1 | solution/solid | Type 4 |
| fumaric | 006-04 | THF | methanol | 2:1 | solid | Type 4 |
| galactaric (mucic) | 003-29 | THF | none | 1:1 | solution/solid | Type 3 + co-former |
| galactaric (mucic) | 006-29 | THF | none | 2:1 | solid | Type 3 + co-former |
| gentisic | 006-17 | THF | methanol | 2:1 | solid | Type 27 |
| gentisic | 003-17 | THF | methanol | 1:1 | solution/solid | Type 3 |
| gluconic (D) | 006-25 | THF | methanol | 2:1 | solid | Type 2 + Type 3 |
| gluconic (D) | 003-25 | THF | methanol | 1:1 | solution/solid | Type 3 |
| gluconic (D) | 003-32 | THF | water | 1:1 | solution/solid | Type 3 |
| glycolic (hydroxyacetic) | 006-05 | THF | methanol | 2:1 | solid | Type 2 |
| glycolic (hydroxyacetic) | 003-05 | THF | methanol | 1:1 | solution/solid | Type 2 + Type 3 |
| HCl | 003-18 | THF | water | 1:1 | solid | Type 3 |
| HCl | 006-18 | THF | water | 2:1 | solid | Type 3 |
| HI | 003-31 | THF | water | 1:1 | solution/solid | Type 3 (disordered) |
| isethionic | 003-35 | THF | methanol | 1:1 | solution/solid | Type 3 |
| ketoglutaric (oxoglutaric) | 006-06 | THF | methanol | 2:1 | solid | disordered |
| ketoglutaric (oxoglutaric) | 003-06 | THF | methanol | 1:1 | solution/solid | Type 3 |
| lactobionic | 003-19 | THF | water | 1:1 | solution/solid | Type 3 |
| lactobionic | 006-19 | THF | water | 2:1 | solid | Type 3 |
| maleic | 006-20 | THF | methanol | 2:1 | solid | amorphous |
| maleic | 003-20 | THF | methanol | 1:1 | solution/solid | Type 2 + Type 3 |
| malic (L) | 006-07 | THF | methanol | 2:1 | solid | Type 2 + Type 3 |
| malic (L) | 003-07 | THF | methanol | 1:1 | solution/solid | Type 3 |
| malonic | 006-08 | THF | methanol | 2:1 | solid | Type 2 + Type 3 |
| malonic | 003-08 | THF | methanol | 1:1 | solution/solid | Type 3 |
| mandelic (DL) | 003-09 | THF | methanol | 1:1 | solution/solid | Type 2 + Type 3 |
| mandelic (DL) | 006-09 | THF | methanol | 2:1 | solid | Type 2 + Type 3 |
| methanesulfonic | 006-23 | THF | acetone | 2:1 | gel | amorphous |
| methanesulfonic | 003-23 | THF | acetone | 1:1 | solution/solid | Type 3 |
| naphtalene-1,5-disulfonic | 003-24 | THF | acetone | 1:1 | solid | Type 10 |
| naphtalene-1,5-disulfonic | 006-24 | THF | acetone | 2:1 | solid | Type 11 |
| nitric | 003-30 | THF | water | 1:1 | solid | Type 3 |
| oxalic | 006-10 | THE | methanol | 2:1 | solid | disordered |
| oxalic | 003-10 | THE | methanol | 1:1 | solution/solid | Type 2 + Type 3 |
| pamoic | 003-33 | THF | DMSO | 1:1 | solution/gel | n/a |
| phosphoric | 006-26 | THF | methanol | 2:1 | solid | Type 2 + Type 3 |
| phosphoric | 003-26 | THF | methanol | 1:1 | solution/solid | Type 3 |
| p-toluenesulfonic | 003-16 | THF | acetone | 1:1 | solid | Type 7 |
| p-toluenesulfonic | 006-16 | THF | acetone | 2:1 | solid | Type 8 |

TABLE 4-continued

Screening results from slow evaporation experiments involving Q203 free base

| Salt former | Sample No. (ND-0006E-) | Solvent | Antisolvent | Acid:API (molar eq.) | Result | XRPD |
|---|---|---|---|---|---|---|
| pyroglutamic (L) | 006-11 | THF | methanol | 2:1 | solid | Type 2 + co-former |
| pyroglutamic (L) | 003-11 | THF | methanol | 1:1 | solution/solid | Type 3 + co-former |
| pyruvic (2-oxopropanoic) | 003-21 | THF | methanol | 1:1 | solution/solid | Type 3 |
| pyruvic (2-oxopropanoic) | 006-21 | THF | methanol | 2:1 | solid | Type 3 |
| saccharin | 006-27 | THF | acetone | 2:1 | gel | n/a |
| saccharin | 003-27 | THF | acetone | 1:1 | solution/solid | Type 25 + Type 3 |
| salicylic | 003-34 | THF | acetone | 1:1 | solution/solid | Type 48 |
| succinic | 006-12 | THF | methanol | 2:1 | solid | Type 2 + Type 3 |
| succinic | 003-12 | THF | methanol | 1:1 | solution/solid | Type 3 |
| sulphuric | 006-28 | THF | water | 2:1 | solid | — |
| sulphuric | 003-28 | THF | water | 1:1 | solution/solid | Type 3 |
| tartaric (L) | 006-13 | THF | methanol | 2:1 | solid | Type 2 + additonal peak |
| tartaric (L) | 003-13 | THF | methanol | 1:1 | solution/solid | Type 3 |
| urea | 003-14 | THF | methanol | 1:1 | solution/solid | Type 3 + co-former |
| urea | 006-14 | THF | methanol | 2:1 | solid | Type 5 |

4.1.2 Rt Slurry

RT (ambient) temperature slurrying experiments were conducted as described in section 2.2.2 using solid generated from slow evaporation experiments involving Q203 free base and coformer (1:1 eq.). Results are shown in Table 5. Novel patterns were observed from XRPD analysis of solids involving urea (Type 5), EDSA (Type 9), 2-furoic (Type 13), citric (Type 14), fumaric (Type 15), ketoglutaric (Type 16), NDSA (Type 17), maleic (Type 8), gentisic (Type 9), pTSA (Type 20), tartaric (Type 21), succinic (Type 22), mandelic (Type 23), malic (Type 24), HCl (Type 36), pamoic (Type 50), salicylic (Type 52) and MSA (Type 54). Type3 was also observed both pure and in mixtures from multiple coformers. These Types are discussed further in section 5.

TABLE 5

Screening results from RT slurry experiments

| Co-former | Sample No (ND-0006E-) | Solvent | RT slurry (20° C.) |
|---|---|---|---|
| 2-furoic | 004-01 | MTBE | Type 13 |
| ascorbic | 004-02 | MTBE | Type 3+ |
| benzenesulfonic | 004-15 | MTBE | Type 3 + Type 6 |
| citric | 004-03 | MTBE | Type 14 |
| ethane-1,2-disulfonic | 004-22 | MTBE | Type 9 |
| fumaric | 004-04 | MTBE | Type 15 |
| galactaric (mucic) | 004-29 | MTBE | Type 3 + co-former |
| gentisic | 004-17 | MTBE | Type 19 |
| gluconic (D) | 004-25 | MTBE | Type 3 |
| gluconic (D) | 004-32 | MTBE | Type 3 + additional peaks |
| glycolic (hydroxyacetic) | 004-05 | MTBE | Type 3+ |
| HCl | 004-18 | MTBE | Type 36 |
| HI | 004-31 | MTBE | Type 3 (disordered) |
| ketoglutaric | 004-06 | MTBE | Type 16 |
| lactobionic | 004-19 | MTBE | Type 3 |
| maleic | 004-20 | MTBE | Type 18 |
| malic (L) | 004-07 | MTBE | Type 24 |
| malonic | 004-08 | MTBE | Type 3 |
| mandelic (DL) | 004-09 | MTBE | Type 23 |

TABLE 5-continued

Screening results from RT slurry experiments

| Co-former | Sample No (ND-0006E-) | Solvent | RT slurry (20° C.) |
|---|---|---|---|
| methanesulfonic | 004-23 | MTBE | Type 54 |
| naphtalene-1,5- | 004-24 | MTBE | Type 17 |
| nitric | 004-30 | MTBE | Type 3 |
| oxalic | 004-10 | MTBE | Type 3 |
| pamoic | 004-33 | MTBE | Type 50 |
| phosphoric | 004-26 | MTBE | Type 3 |
| p-toluenesulfonic | 004-16 | MTBE | Type 20 |
| pyroglutamic (L) | 004-11 | MTBE | Type 3+ |
| pyruvic (2- | 004-21 | MTBE | Type 3 |
| saccharin | 004-27 | MTBE | Type 3 |
| salicylic | 004-34 | MTBE | Type 52 |
| succinic | 004-12 | MTBE | Type 22 |
| sulphuric | 004-28 | MTBE | Type 3 (disordered) |
| tartaric (L) | 004-13 | MTBE | Type 21 |
| urea | 004-14 | MTBE | Type 5 |

4.1.3 HT Slurry (40° C.)

High temperature slurrying experiments were conducted as described in section 2.2.2 using solid generated from slow evaporation experiments involving Q203 free base and coformer (both 1:1 and 2:1 eq.). Results are shown in Table 6. Novel patterns were observed from XRPD analysis of solids involving urea (Type 5), 2-furoic (Type 13), fumaric (Type 15), tartaric (Type 21), mandelic (Type 23), NDSA (Type 26), sulphuric (Type 31), BSA (Type 33), EDSA (Type 34) and HCl (Type 35). Types 32, 40 and 41 solid (pure and in mixtures) was observed from multiple coformers. These Types are discussed in more detail in section 5.

TABLE 6

Screening results from slow evaporation experiments involving Q203 free base

| Co-former | Sample No. (ND-0006E-) | Solvent | Antisolvent | Acid:API (molar eq.) | Result | XRPD |
|---|---|---|---|---|---|---|
| 2-furoic | 007-01 | THF | methanol | 2:1 | solid | Type 13 |
| ascorbic | 007-02 | IPA | none | 2:1 | solid | co-acid + additional peaks |
| ascorbic | 010-01 | IPA | water | 1:1 | solid | Type 41 |
| benzenesulfonic | 007-15 | IPA | none | 2:1 | solid | Type 33 |
| citric | 007-03 | IPA | none | 2:1 | solution | n/a |
| ethane-1,2-disulfonic | 007-22 | IPA | none | 2:1 | solid | Type 34 |
| fumaric | 007-04 | IPA | none | 2:1 | solid | Type 15 |
| galactaric (mucic) | 007-29 | IPA | none | 2:1 | solid | Type 32 + co-acid |
| galactaric (mucic) | 010-14 | IPA | water | 1:1 | solid | Type 41 + T28 |
| gentisic | 007-17 | IPA | none | 2:1 | solid | Type 32 |
| gluconic (D) | 007-25 | IPA | none | 2:1 | solid | Type 32 |
| gluconic (D) | 010-11 | acetone | none | 1:1 | solid | Type 40 |
| glycolic (hydroxyacetic) | 007-05 | IPA | none | 2:1 | solid | Type 32 |
| glycolic (hydroxyacetic) | 010-02 | acetone | none | 1:1 | solid | Type 40 |
| HCl | 007-18 | IPA | none | 2:1 | solid | Type 35 |
| ketoglutaric (oxoglutaric) | 007-06 | IPA | none | 2:1 | solid | Type 32 |
| lactobionic | 007-19 | IPA | none | 2:1 | solid | Type 32 + additional peaks |
| lactobionic | 010-07 | IPA | water | 1:1 | solid | Type 41 |
| maleic | 007-20 | IPA | none | 2:1 | solid | Type 32 |
| malic (L) | 007-07 | IPA | none | 2:1 | solid | Type 32 |
| malonic | 007-08 | IPA | none | 2:1 | solid | Type 32 |
| malonic | 010-03 | acetone | none | 1:1 | solid | Type 41 + T28 |
| mandelic (DL) | 007-09 | IPA | none | 2:1 | solid | Type 23 + additional peaks |
| methanesulfonic | 007-23 | IPA | none | 2:1 | solution | n/a |
| methanesulfonic | 010-09 | IPA | water | 1:1 | solid | Type 40 |
| methanesulfonic | 010-10 | acetone | none | 1:1 | solid | Type 40 |
| naphtalene-1,5-disulfonic | 007-24 | IPA | none | 2:1 | solid | Type 26 |
| oxalic | 007-10 | IPA | none | 2:1 | solid | disordered (Type 2?) |
| oxalic | 010-04 | acetone | none | 1:1 | solid | Type 41 |
| oxalic | 010-05 | methanol | none | 1:1 | solid | Type 41 + T28 |
| phosphoric | 007-26 | IPA | none | 2:1 | solid | Type 32 |
| phosphoric | 010-12 | acetone | none | 1:1 | solid | Type 40 |
| p-toluenesulfonic | 007-16 | IPA | none | 2:1 | solid | Pattern A |
| pyroglutamic (L) | 007-11 | IPA | none | 2:1 | solid | Type 32 |
| pyroglutamic (L) | 010-06 | acetone | none | 1:1 | solid | Type 40 |
| pyruvic (2-oxopropanoic) | 007-21 | IPA | none | 2:1 | solid | Type 32 |
| pyruvic (2-oxopropanoic) | 010-08 | acetone | none | 1:1 | solid | Type 41 |
| saccharin | 007-27 | IPA | none | 2:1 | solution | n/a |
| saccharin | 010-13 | IPA | water | 1:1 | solid | Type 41 + T28 |
| succinic | 007-12 | IPA | none | 2:1 | solid | Type 32 |
| sulphuric | 007-28 | IPA | none | 2:1 | solid | Type 31 |
| tartaric (L) | 007-13 | IPA | none | 2:1 | solid | Type 21 |
| urea | 007-14 | IPA | none | 2:1 | solid | Type 5 |

4.1.4 Sonication

A selected neat or mixed solvent system was added to sufficient Q203 free base (Batch C12032302-J16001M) to form a paste. The paste was sonicated at 70% intensity using a Cole-Parmer 130W ultrasonic processor using a pulsed program. All solids recovered from these experiments were dried under nitrogen prior to analysis by XRPD. The results of these experiments are shown in Table 7. XRPD analysis of the resultant solids showed new patterns from experiments involving pTSA (Type 7), NDSA (Type 10), mandelic (Type 23), malic (Type 24), ketoglutaric (Type 29), nitric (Type 49), pamoic (Type 51) and salicylic acid (Type 53).

Type 3 and 25 solid (pure and in mixtures) was observed from multiple coformers. These Types are discussed in more detail in section 5. Each Type is further detailed in section 5.

TABLE 7

Screening results from sonication experiments

| Co-former | Sample N° (ND-0006E-) | Solvent | Sonication |
|---|---|---|---|
| ketoglutaric | 005-06 | THF | Type 29 |
| lactobionic | 005-19 | THF | Type 3 |
| maleic | 005-20 | THF | Type 25 |
| malic (L) | 005-07 | THF | Type 24 |
| malonic | 005-08 | THF | Type 25 + Type 3 |
| mandelic (DL) | 005-09 | THF | Type 23 |
| methanesulfonic | 005-23 | THF | Type 3 (disordered) |
| naphtalene-1,5- | 005-24 | THF | Type 10 |
| nitric | 005-30 | THF | Type 49 |
| oxalic | 005-10 | THF | Type 25 + Type 3 |
| pamoic | 005-33 | THF | Type 51 |
| phosphoric | 005-26 | THF | Type 25 + Type 3 |
| p-toluenesulfonic | 005-16 | THF | Type 7 |
| pyroglutamic (L) | 005-11 | THF | Type 25 + Type 3 |
| pyruvic (2- | 005-21 | THF | Type 3 (disordered) |
| saccharin | 005-27 | THF | Type 25 |
| salicylic | 005-34 | THF | Type 53 |
| succinic | 005-12 | THF | Type 3 + unknown |
| sulphuric | 005-28 | THF | Type 3 (disordered) |
| tartaric (L) | 005-13 | THF | Type 25 |
| urea | 005-14 | THF | Type 3 |

4.2 Solid State Screening Techniques

The non-solvent based (solid state) screening methods include ball milling, sublimation, melting and compression (section 2.2). These techniques mimic conditions that are likely to be encountered in large scale processing, e.g. on hot reactor walls or during drying and tabletting operations. Varying the nucleation conditions in this way maximises the chance of finding new forms and also the frequency of occurrence of these forms under typical processing conditions.

4.2.1 Co-Melting (Kofler Melt)

Co-melting (Kofler melt) experiments were conducted as described in section 2.2.5 using Q203 free base and coformer (1:1 eq.). Results are detailed in Table 8. These experiments generally produced amorphous or very disordered solids. XRPD analysis of solid produced from melting Q203 free base with gluconic acid showed a novel pattern, assigned as Type 38. A novel pattern (Type 39) was also observed from melting experiments involving multiple coformers. These two Types are discussed in more detail in section 5.

TABLE 8

Results from co-melting experiments

| Salt former | Sample (ND-0006E-) | Result | XRPD |
|---|---|---|---|
| ascorbic | 009-01 | solid | Form A + co-former |
| galactaric (mucic) | 009-10 | solid | amorphous |
| gluconic (D) | 009-07 | solid | Type 38 |
| glycolic (hydroxyacetic) | 009-02 | solid | v. disordered |
| lactobionic | 009-05 | solid | amorphous |
| malonic | 009-03 | solid | Type 39 |
| phosphoric | 009-08 | solid | amorphous |
| pyroglutamic (L) | 009-04 | solid | v. disordered |
| pyruvic (2-oxopropanoic) | 009-06 | solid | Type 39 |
| saccharin | 009-09 | solid | Type 39 + saccharin |

4.2.2 Liquid Assisted Grinding (LAG)

Co-melting (Kofler melt) experiments were conducted as described in section 2.2.5 using Q203 free base and coformer (1:1 eq.). Results are detailed in Table 9. XRPD analysis of resultant solids showed new patterns from LAG experiments involving phosphoric (Type 37) and ascorbic acid (Type 43). Types 28, 40 and 41 were observed from multiple coformers. These Types are detailed in section 5.

TABLE 9

Results from LAG experiments

| Salt former | Sample (ND-0006E-) | Solvent | Antisolvent | Result | XRPD |
|---|---|---|---|---|---|
| 2-furoic | 008-01 | acetone | none | solid | Type 41 + T28 |
| ascorbic | 008-02 | IPA | water | solid | Type 43 |
| citric | 008-03 | acetone | none | solid | Type 40 + additional peaks |
| galactaric (mucic) | 008-15 | IPA | water | solid | Type 28 |
| gentisic | 008-08 | acetone | none | solid | Type 42 |
| gluconic (D) | 008-12 | acetone | none | solid | Type 28 + trace T3 |
| glycolic (hydroxyacetic) | 008-04 | acetone | none | solid | Type 40 + additional peaks |
| lactobionic | 008-09 | IPA | water | solid | Type 41 |
| malonic | 008-05 | acetone | none | solid | Type 40 |
| methanesulfonic | 008-11 | acetone | none | solid | amorphous |
| oxalic | 008-06 | methanol | none | solid | amorphous |
| phosphoric | 008-13 | acetone | none | solid | Type 37 |
| pyroglutamic (L) | 008-07 | acetone | none | solid | Type 40 + Form A + co-former |
| pyruvic (2-oxopropanoic) | 008-10 | acetone | none | solid | Type 40 |
| saccharin | 008-14 | IPA | water | solid | Type 41 + T28 |

4.3 Conclusions from Salt/Co-Crystal Screening

Approximately 20 T experiments were carried out using solvent and non-solvent based techniques. 2 crystalline XRPD patterns were observed during this study, including the as received material. This showed a high tendency of Q203 to generate new patterns from various co-formers and techniques. Polymorphism of the Q203 was observed but most of the new patterns are likely attributed to salts and/or potential co-crystals of Q203 free base.

TABLE 10

Summary of the observed solids of Q203 (sorted out by co-former)

| oType | Co-former | Comments/<br>Tentative Assignments |
|---|---|---|
| 13 | 2-furoic | Crystalline, prepared by a range of techniques and solvents<br>$^1$H NMR suggests no salt formation<br>Potential co-crystal or polymorph of Q203 free base |
| 43 | ascorbic | Disordered crystalline, prepared by LAG using a mixture of IPA/water<br>Proton NMR: no PS, ~0.8 molar eq. co-former, no residual IPA |
| 6 | benzenesulfonic | Disordered crystalline, prepared by slow evaporation using THF/acetone<br>$^1$H NMR suggests salt formation with ~0.25 molar eq. of THF<br>Q203 benzenesulfonate salt (1:1 or 2:1 stoichiometry) |
| 12 | benzenesulfonic | Crystalline, prepared by sonication using THF<br>$^1$H NMR suggests salt formation with ~0.03 molar eq. of THF<br>Q203 benzenesulfonate (1:1 stoichiometry) |
| 33 | benzenesulfonic | Crystalline, prepared by HT slurrying for 7 d using IPA<br>$^1$H NMR suggests salt formation with no residual solvent<br>Q203 benzenesulfonate salt (likely 2:1 stoichiometry) |
| 14 | citric | Crystalline, prepared by RT slurrying for 7 d using MTBE<br>$^1$H NMR suggests no salt formation<br>Potential co-crystal or polymorph of Q203 free base |
| 9 | ethane-1,2-disulfonic | Disordered crystalline, prepared by a range of techniques and solvents<br>$^1$H NMR suggests salt formation with ~0.07 molar eq. of MTBE<br>Q203 edisylate (potential 1:1 stoichiometry) |
| 34 | ethane-1,2-disulfonic | Disordered crystalline, prepared by HT slurrying for 7 d using IPA<br>$^1$H NMR suggests salt formation with no residual solvent<br>Q203 edisylate salt (2:1 stoichiometry) |
| 4 | fumaric | Crystalline, prepared by slow evaporation using a mixture of THF/MeOH<br>$^1$H NMR suggests no salt formation and~0.5 eq residual MeOH<br>Potential MeOH hemi-solvate of co-crystal or polymorph of Q203 free base |
| 15 | fumaric | Crystalline, prepared by RT/HT slurrying for 7 d using MTBE/IPA<br>$^1$H NMR suggests no salt formation (~0.7molar eq. fumaric acid)<br>Potential co-crystal or polymorph of Q203 free base |
| 30 | fumaric | Crystalline, prepared by sonication using THF<br>$^1$H NMR shows no peak shifting, no residual solvent and ~0.9 molar eq. of fumaric acid suggesting possible co-crystal or polymorph of Q203 free base. |
| 28 | Galactaric, gluconic | Crystalline, prepared by LAG experiments using a mixture of IPA/water and acetone from galactaric and gluconic respectively<br>$^1$H NMR suggests no salt formation (~0.08 molar eq. IPA).<br>Likely polymorph of the Free base |
| 19 | gentisic | Crystalline (similar to T3), prepared by RT slurrying for 7 d using MTBE<br>$^1$H NMR suggests no salt formation<br>(~0.1 eq residual MTBE and 0.2 eq. free acid)<br>Potential co-crystal or polymorph of Q203 free base |
| 27 | gentisic | Disordered crystalline, prepared by slow evaporation using a mixture THF/methanol<br>$^1$H NMR shows no peak shifting, with ~0.5 molar eq. of THF, ~2 mol. eq. of co-former, suggesting possible THF hemisolvate of co-crystal or polymorph of the free base. |
| 42 | gentisic | Disordered crystalline, prepared by LAG using a mixture of IPA/water |
| 38 | gluconic | Crystalline, prepared by co-melt<br>Proton NMR: no PS as expected, no solvent, no presence of co-former<br>TG/DTA: melt at ~165° C.<br>Likely polymorph of the free base |
| 35 | HCl | Disordered crystalline, prepared by HT slurrying for 7 d using IPA<br>$^1$H NMR suggests salt formation with no residual solvent<br>Q203 HCl salt.<br>The stoichiometry has not been determined |
| 36 | HCl | Crystalline, prepared by HT slurrying for 7 d using IPA<br>$^1$H NMR suggests salt formation with ~0.007 molar eq. of MTBE<br>Q203 HCl salt.<br>The stoichiometry has not been determined |
| 55 | HCl | Crystalline with the presence of disordered material, prepared by evaporation from THE<br>Proton NMR: shifting confirming salt formation. |
| 56 | HCl | Crystalline with the presence of disordered material, generated as part of the pH profile analysis from Type 55 and phosphate salt at pH1<br>Proton NMR: shifting confirming salt formation |

TABLE 10-continued

| Summary of the observed solids of Q203 (sorted out by co-former) | | |
|---|---|---|
| oType | Co-former | Comments/ Tentative Assignments |
| 16 | ketoglutaric (oxoglutaric) | Crystalline, prepared by RT slurrying for 7 d using MTBE $^1$H NMR shows possibly PS at 2.9 ppm, 0.02 eq residual MTBE. Nature of this Type needs to be confirmed |
| 29 | ketoglutaric (oxoglutaric) | Disordered crystalline, prepared by sonication using THF $^1$H NMR shows no peak shifting, with ~0.16 molar eq. of THF and ~0.9 molar eq. of ketoglutaric acid suggesting possible co-crystal or polymorph of Q203 free base. |
| 18 | maleic | Crystalline (similar to T19), prepared by RT slurrying for 7 d using MTBE $^1$H NMR suggests salt formation and ~0.2 eq residual MTBE Potential Q203 maleate (1:1 stoichiometry), possible non-stoichiometric MTBE solvate |
| 24 | malic (L) | Crystalline, prepared by RT slurrying using MTBE and by sonication using THE $^1$H NMR shows no peak shifting, no residual solvent and ~1 molar eq. of malic acid suggesting possible co-crystal or polymorph of the free base. |
| 23 | mandelic (DL) | Crystalline, prepared by RT and HT slurrying using MTBE and IPA, and by sonication $^1$H NMR shows no Peak shifting and ~0.8 molar eq. of mandelic acid suggesting possible co-crystal or polymorph of the free base. |
| 54 | methanesulfonic | Disordered crystalline, prepared by RT slurry for 7 d using MTBE Very similar to Type 3 Proton NMR: peak shifting with ~0.18 molar eq. of MTBE suggesting likely MSA salt of Q203 with a 1:1 stoichiometry. |
| 2 | multiple co-formers | Crystalline, prepared by slow evaporation using THF/MeOH $^1$H NMR suggests no salt formation and no visible degradation Potential polymorph of Q203 free base |
| 3 | multiple co-formers | Crystalline, prepared by a range of techniques and solvents 1H NMR suggests no salt formation. Potential polymorph of Q203 free base |
| 25 | multiple co-formers | Crystalline, prepared by multiple solvents and techniques obtained as pure or as a mixture with Type 3. This suggests polymorph of the free base. But $^1$H NMR analysis of material from maleic suggests salt formation with residual solvent (~0.5 molar eq THF). Likely a THF hemi-solvate of the salt of Q203. This may be explained by possible salt formation in-situ during NMR preparation sample. |
| 32 | multiple co-formers and stoichiometry | Crystalline, prepared by HT slurrying for 7 d using IPA $^1$H NMR shows no peak shifting, no residual solvent and ~0.2 molar eq. of ketoglutaric acid. As obtained from multiple co-formers, likely a polymorph of Q203 free base. |
| 39 | multiple co-formers | Crystalline, prepared from various co-formers (malonic, pyruvic and saccharin) by co-melting technique suggesting polymorph of the free base Proton NMR of saccharin and pyruvic solids showed salt formation suggesting salt formation had occurred during NMR sample preparation. |
| 40 | multiple co-formers | Crystalline, prepared from various co-formers (gluconic, malonic, pyruvic. . .) and various techniques co-melting technique suggesting polymorph of the free base |
| 41 | multiple co-formers | Crystalline, prepared from various co-formers (ascorbic, lactobionic, galactaric) and techniques (HT slurry, LAG) Likely polymorph of the free base |
| 1 | n/a | material, crystalline, free based $^1$H NMR analysis showed no visible degradation and trace of residual solvent (may be acetone around ~80 ppm). |
| 10 | naphtalene-1,5-disulfonic | Crystalline, prepared by a range of techniques and solvents $^1$H NMR suggests salt formation and ~0.5 molar eq. residual THF Potential THF hemisolvate of Q203 napthalenedisulfonate (2:1 stoichiometry) |
| 11 | naphtalene-1,5-disulfonic | Crystalline (similar to T10), prepared by slow evaporation using THF $^1$H NMR suggests salt formation and ~0.7 molar eq. residual THF Potential THF solvate of Q203 napthalenedisulfonate Stoichiometry not determined due to the presence of free acid |
| 17 | naphtalene-1,5-disulfonic | Crystalline (similar to T11), prepared by RT slurrying for 7 d using MTBE $^1$H NMR suggests salt formation with ~0.08 molar eq. of MTBE Potential Q203 NDSA salt (2:1 stoichiometry) |
| 26 | naphtalene-1,5-disulfonic | Crystalline, prepared by slow evap, followed by HT slurrying for 7 d using IPA $^1$H NMR suggests salt formation (~0.04 molar eq. IPA). The stoichiometry needs to be confirmed |
| 49 | nitric | Disordered crystalline, prepared by sonication using THF Very similar to Type 3 + additional peaks Proton NMR: peak shifting with ~0.25 molar eq. of THF suggesting likely Type 49 to be a nitrate salt of Q203. |

TABLE 10-continued

Summary of the observed solids of Q203 (sorted out by co-former)

| oType | Co-former | Comments/ Tentative Assignments |
|---|---|---|
| 45 | oxalic | Crystalline, prepared by HT slurry using acetone<br>Proton NMR: peak shifting with ~0.06 molar eq. of acetone.<br>Stoichiometry not determined.<br>Oxalate salt of Q203. |
| 46 | oxalic | Crystalline, prepared by HT slurry using methanol<br>Proton NMR: no peak shifting. Stoichiometry not determined.<br>Likely polymorph of the free base. |
| 50 | pamoic | Crystalline, prepared by RT slurry using MTBE<br>Similarities with Type 3<br>Proton NMR: no peak shifting with ~0.07 molar eq. of MTBE and ~0.65 molar eq. of co-former<br>Possibly polymorph of Q203 free base or co-crystal. |
| 51 | pamoic | Crystalline, prepared by sonication using THF<br>Proton NMR: no PS, ~0.9 molar eq. co-former, ~0.02 molar eq. of THF<br>Potential polymorph or co-crystal of Q203. |
| 37 | phosphoric | Crystalline, prepared by HT slurry and by LAG using acetone<br>Proton NMR showed peak shifting with ~0.09 molar eq. of acetone<br>Suggesting Q203 phosphate salt.<br>The stoichiometry has not been determined |
| Pat A | p-toluenesulfonic | Crystalline, prepared by slow evap. then HT slurrying using IPA, XRPD pattern similar to the ditosylate salt (Pattern A)<br>$^1$H NMR confirmed salt formation with a 2:1 stoichiometry |
| 7 | p-toluenesulfonic | Crystalline, prepared by a range of techniques and solvents<br>$^1$H NMR suggests salt formation with no residual solvents. Additional peaks were observed.<br>Q203 tosylate (potential 1:1 stoichiometry) |
| 8 | p-toluenesulfonic | Crystalline, prepared by slow evaporation using THF/acetone<br>$^1$H NMR suggests salt formation with ~0.15 molar eq. of THF<br>Q203 tosylate (potential 2:1 stoichiometry) |
| 20 | p-toluenesulfonic | Crystalline, prepared by RT slurrying for 7 d using MTBE<br>$^1$H NMR suggests salt formation (~0.01 molar eq. MTBE)<br>Q203 tosylate (1:1 stoichiometry) |
| 44 | saccharin | Disordered material, very similar to Type 41, prepared by LAG using a mixture of IPA/water.<br>Proton NMR: peak shifting, ~1 molar eq. of saccharin and ~0.5 molar eq. of IPA suggesting IPA hemisolvate of saccharin salt |
| 47 | saccharin | Crystalline, prepared by HT slurry using a mixture of IPA/water<br>Proton NMR: peak shifting with trace of IPA, ~0.7 mol. eq. of co-former suggesting salt formation of Q203 saccharin salt. |
| 48 | salicylic | Crystalline, prepared by HT slurry using a mixture of THF/acetone<br>Proton NMR: no peak shifting, ~0.9 molar eq. co-former, ~0.1 molar eq. of THF and no residual acetone suggesting potential co-crystal or polymorph of the free base. |
| 52 | salicylic | Crystalline, prepared by RT slurry using MTBE<br>Similarities with Type 3<br>Proton NMR: no PS, ~0.4 molar eq. co-former, ~0.4 molar eq. of MTBE<br>Likely polymorph of Q203. |
| 53 | salicylic | Crystalline, prepared by sonication using THF<br>Proton NMR: no PS, ~1.0 molar eq. co-former, ~0.04 molar eq. of THF<br>TG/DTA: melt at ~132° C.<br>Potential co-crystal of Q203. |
| 22 | succinic | Crystalline, prepared by RT slurrying for 7 d using MTBE<br>1H NMR suggests salt formation (~0.01 molar eq. MTBE)<br>Potential Q203 tosylate (1:1 stoichiometry) |
| 31 | sulphuric | Crystalline, prepared by HT slurrying for 7 d using IPA<br>$^1$H NMR suggests salt formation with no residual solvent and the presence of additional peaks (possibly degradation).<br>The stoichiometry has not been determined |
| 21 | tartaric (L) | Crystalline, prepared by RT/HT slurrying for 7 d using MTBE/IPA<br>1H NMR suggests no salt formation<br>(~0.6 eq tartaric acid + unknown peak at 8.1 ppm)<br>Potential co-crystal or polymorph of Q203 free base |
| 5 | urea | Crystalline, prepared by a range of techniques and solvents<br>$^1$H NMR suggests no salt formation, no residual solvent<br>Potential co-crystal or polymorph of Q203 free base |

5 Preparation and Characterisation of Novel Types 5.1 Pattern a (p-Toluenesulfonic)

Figure 24:
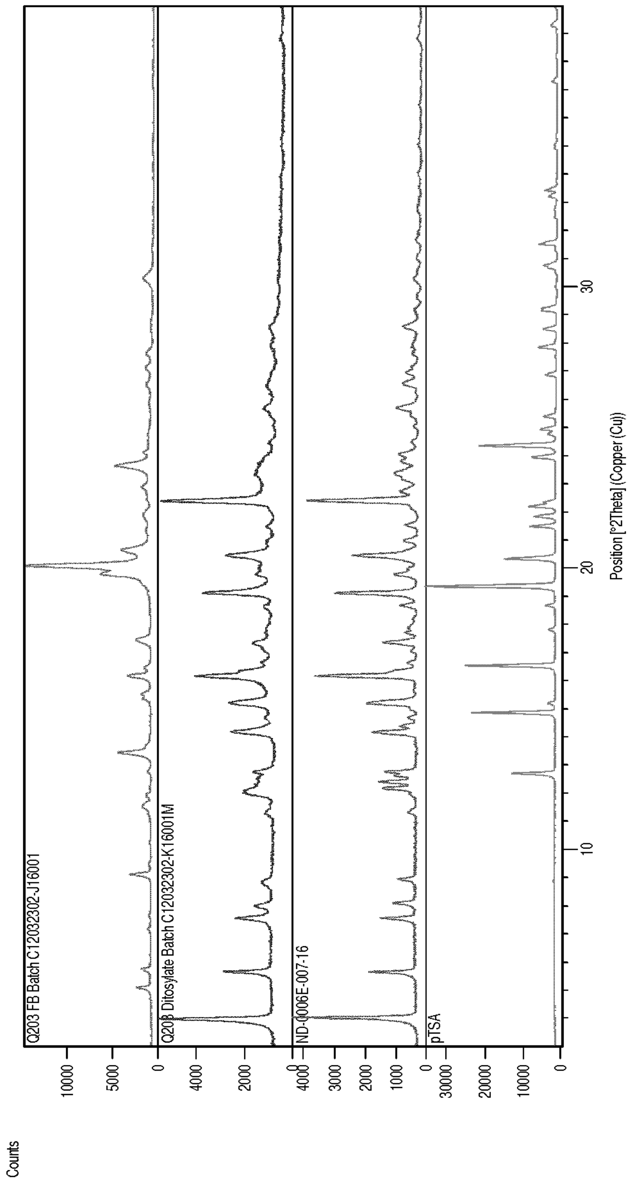
FIG. 24 shows XRPD patterns of Q203 free base (top trace), ditosylate salt (Pattern A, 2nd trace from top), ND-0006E-007-16 ($3^{rd}$ trace from top) and pTSA (bottom trace).

Pattern A material (ditosylate salt "form A") was isolated from slow evaporation then HT slurry experiment using pTSA and Q203 free base (1:1 acid/API) in IPA. XRPD analysis of Pattern A (ND-0006E-003-16) showed the material was crystalline (see also figures 24+30).

5.2 Type 2

Figure 25:
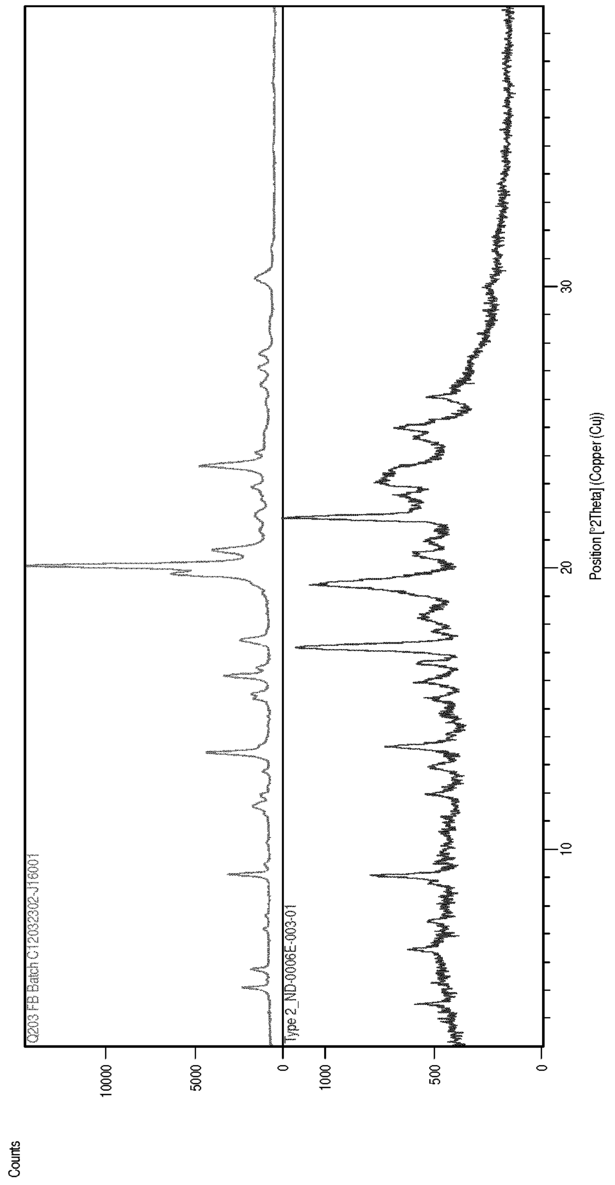
FIG. 25 shows XRPD patterns of Q203 free base (top trace) and ND-0006E-003-01 (Type 2, bottom trace).

Type 2 material was generated from slow evaporation experiments involving various acids and Q203 free base (both 1:1 and 2:1 acid/API) in THF/MeOH. Experimental conditions leading to pure Type 2 and Type 2 mixtures (with co-former or Type 3) are highlighted in Table 11. XRPD analysis of Type 2 solid (ND-0006E-003-01) showed the material was crystalline with some disorder present (FIG. 25). $^{1}H$ NMR analysis of Type 2 material showed no salt formation (data not shown). As this Type was obtained from different co-formers, it is likely to be a polymorph of Q203 free base.

TABLE 11

Experimental conditions leading to Type 2 solid (pure and mixtures)

| Salt former | Sample No. (ND-0006E-) | Acid:API (molar ratio) | Result | XRPD |
|---|---|---|---|---|
| 2-furoic | 003-01 | 1:1 | solution/solid | Type 2 |
| glycolic (hydroxyacetic) | 006-05 | 2:1 | solid | Type 2 |
| 2-furoic | 006-01 | 2:1 | solid | Type 2 + co-former |
| pyroglutamic (L) | 006-11 | 2:1 | solid | Type 2 + co-former |
| tartaric (L) | 006-13 | 2:1 | solid | Type 2 + additional peak |
| glycolic (hydroxyacetic) | 003-05 | 1:1 | solution/solid | Type 2 + 3 |

TABLE 11-continued

Experimental conditions leading to Type 2 solid (pure and mixtures)

| Salt former | Sample No. (ND-0006E-) | Acid:API (molar ratio) | Result | XRPD |
|---|---|---|---|---|
| mandelic (DL) | 003-09 | 1:1 | solution/solid | Type 2 + 3 |
| oxalic | 003-10 | 1:1 | solution/solid | Type 2 + 3 |
| maleic | 003-20 | 1:1. | solution/solid | Type 2 + 3 |
| malic (L) | 006-07 | 2:1 | solid | Type 2 + 3 |
| malonic | 006-08 | 2:1 | solid | Type 2 + 3 |
| mandelic (DL) | 006-09 | 2:1 | solid | Type 2 + 3 |
| succinic | 006-12 | 2:1 | solid | Type 2 + 3 |
| gluconic (D) | 006-25 | 2:1 | solid | Type 2 + 3 |
| phosphoric | 006-26 | 2:1 | solid | Type 2 + 3 |

5.3 Type 3

Figure 26:
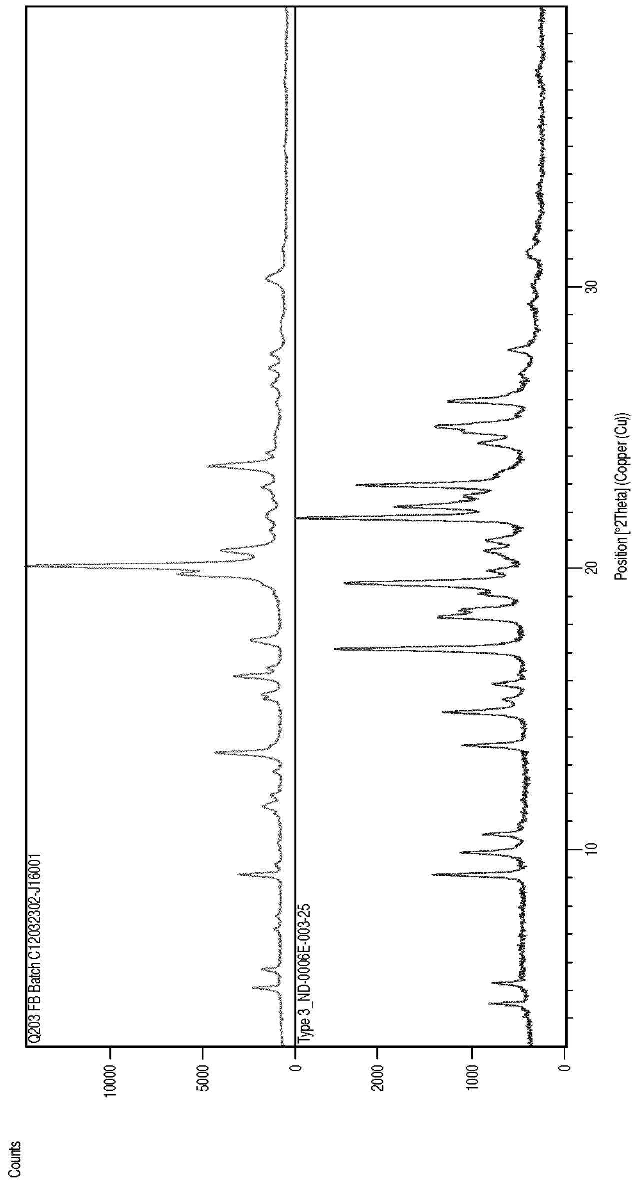
FIG. 26 shows XRPD patterns of Q203 free base (top trace) and ND-0006E-003-25 (Type 3, bottom trace).

Type 3 material was generated from a range of experiments involving selected acids and Q203 free base (both 1:1 and 2:1 acid/API) in neat and mixed solvent systems. Experimental conditions leading to pure Type 3 and Type 3 mixtures (with co-former, Type 2, Type 6 or unknown) are highlighted in Table 12. XRPD analysis of Type 3 solid (ND-0006E-003-25) showed the material was crystalline (FIG. 26). $^{1}H$ NMR analysis of Type 3 material showed no salt formation (data not shown). As this Type was obtained from different co-formers and solvent systems, it is likely to be a polymorph of Q203 free base.

TABLE 12

Experimental conditions leading to Type 3 solid (pure and mixtures)

| Salt former | Sample No. (ND-0006E-) | Solvent | Antisolvent | Screen method | Acid:API (molar ratio) | Result | XRPD |
|---|---|---|---|---|---|---|---|
| succinic | 003-12 | THF | methanol | slow evap | 1:1 | solution/solid | Type 3 |
| tartaric (L) | 003-13 | THF | methanol | slow evap | 1:1 | solution/solid | Type 3 |
| gluconic (D) | 003-25 | THF | methanol | slow evap | 1:1 | solution/solid | Type 3 |
| phosphoric | 003-26 | THF | methanol | slow evap | 1:1 | solution/solid | Type 3 |
| sulphuric | 003-28 | THF | water | slow evap | 1:1 | solution/solid | Type 3 |
| oxalic | 004-10 | MTBE | none | slurry (20° C.) | 1:1 | solid | Type 3 |
| gluconic (D) | 004-25 | MTBE | none | slurry (20° C.) | 1:1 | solid | Type 3 |
| phosphoric | 004-26 | MTBE | none | slurry (20° C.) | 1:1 | solid | Type 3 |
| saccharin | 004-27 | MTBE | none | slurry (20° C.) | 1:1 | solid | Type 3 |
| urea | 005-14 | THF | none | sonication | 1:1 | solid | Type 3 |
| gluconic (D) | 005-25 | THF | none | sonication | 1:1 | solid | Type 3 |
| citric | 003-03 | THF | methanol | slow evap | 1:1 | solution/solid | Type 3 |
| ketoglutaric (oxoglutaric) | 003-06 | THF | methanol | slow evap | 1:1 | solution/solid | Type 3 |
| malic (L) | 003-07 | THF | methanol | slow evap | 1:1 | solution/solid | Type 3 |
| malonic | 003-08 | THF | methanol | slow evap | 1:1 | solution/solid | Type 3 |
| gentisic | 003-17 | THF | methanol | slow evap | 1:1. | solution/solid | Type 3 |
| HCl | 003-18 | THF | water | slow evap | 1:1 | solid | Type 3 |
| lactobionic | 003-19 | THF | water | slow evap | 1:1 | solution/solid | Type 3 |
| pyruvic (2-oxopropanoic) | 003-21 | THF | methanol | slow evap | 1:1 | solution/solid | Type 3 |
| methanesulfonic | 003-23 | THF | acetone | slow evap | 1:1 | solution/solid | Type 3 |

TABLE 12-continued

Experimental conditions leading to Type 3 solid (pure and mixtures)

| Salt former | Sample No. (ND-0006E-) | Solvent | Antisolvent | Screen method | Acid:API (molar ratio) | Result | XRPD |
|---|---|---|---|---|---|---|---|
| malonic | 004-08 | MTBE | none | slurry (20° C.) | 1:1 | solid | Type 3 |
| lactobionic | 004-19 | MTBE | none | slurry (20° C.) | 1:1 | | Type 3 |
| pyruvic (2-oxopropanoic) | 004-21 | MTBE | none | slurry (20° C.) | 1:1 | solid | Type 3 |
| glycolic (hydroxyacetic) | 005-05 | THF | none | sonication | 1:1 | solid | Type 3 |
| lactobionic | 005-19 | THF | none | sonication | 1:1 | solid | Type 3 |
| HCl | 006-18 | THF | water | slow evap | 2:1 | solid | Type 3 |
| lactobionic | 006-19 | THF | water | slow evap | 2:1 | solid | Type 3 |
| pyruvic (2-oxopropanoic) | 006-21 | THF | methanol | slow evap | 2:1 | solid | Type 3 |
| sulphuric | 004-28 | MTBE | none | slurry (20° C.) | 1:1 | | Type 3 (disordered) |
| pyruvic (2-oxopropanoic) | 005-21 | THF | none | sonication | 1:1 | solid | Type 3 (disordered) |
| methanesulfonic | 005-23 | THF | none | sonication | 1:1 | solid | Type 3 (disordered) |
| sulphuric | 005-28 | THF | none | sonication | 1:1 | solid | Type 3 (disordered) |
| ascorbic | 004-02 | MTBE | none | slurry (20° C.) | 1:1 | solid | Type 3 + co-former |
| glycolic (hydroxyacetic) | 004-05 | MTBE | none | slurry (20° C.) | 1:1 | solid | Type 3 + co-former |
| pyroglutamic (L) | 004-11 | MTBE | none | slurry (20° C.) | 1:1 | solid | Type 3 + co-former |
| ascorbic | 006-02 | THF | methanol | slow evap | 2:1 | solid | Type 3 + co-former |
| methanesulfonic | 004-23 | MTBE | none | slurry (20° C.) | 1:1 | solid | Type 3 + additional peaks |
| ascorbic | 003-02 | THF | methanol | slow evap | 1:1 | solution/ solid | Type 3 + co-former |
| pyroglutamic (L) | 003-11 | THF | methanol | slow evap | 1:1 | solution/ solid | Type 3 + co-former |
| urea | 003-14 | THF | methanol | slow evap | 1:1 | solution/ solid | Type 3 + co-former |
| galactaric (mucic) | 003-29 | THF | none | slow evap | 1:1 | solution/ solid | Type 3 + co-former |
| galactaric (mucic) | 004-29 | MTBE | none | slurry (20° C.) | 1:1 | solid | Type 3 + co-former |
| ascorbic | 005-02 | THF | none | sonication | 1:1 | solid | Type 3 + co-former |
| galactaric (mucic) | 005-29 | THF | none | sonication | 1:1 | solid | Type 3 + co-former |
| galactaric (mucic) | 006-29 | THF | none | slow evap | 2:1 | solid | Type 3 + co-former |
| benzenesulfonic | 003-15 | THF | acetone | slow evap | 1:1 | solid | Type 3 + Type 6 |
| benzenesulfonic | 004-15 | MTBE | none | slurry (20° C.) | 1:1 | solid | Type 3 + Type 6 |
| succinic | 005-12 | THF | none | sonication | 1:1 | solid | Type 3 + unknown |

5.4 Type 4 (Fumaric)

Figure 27:
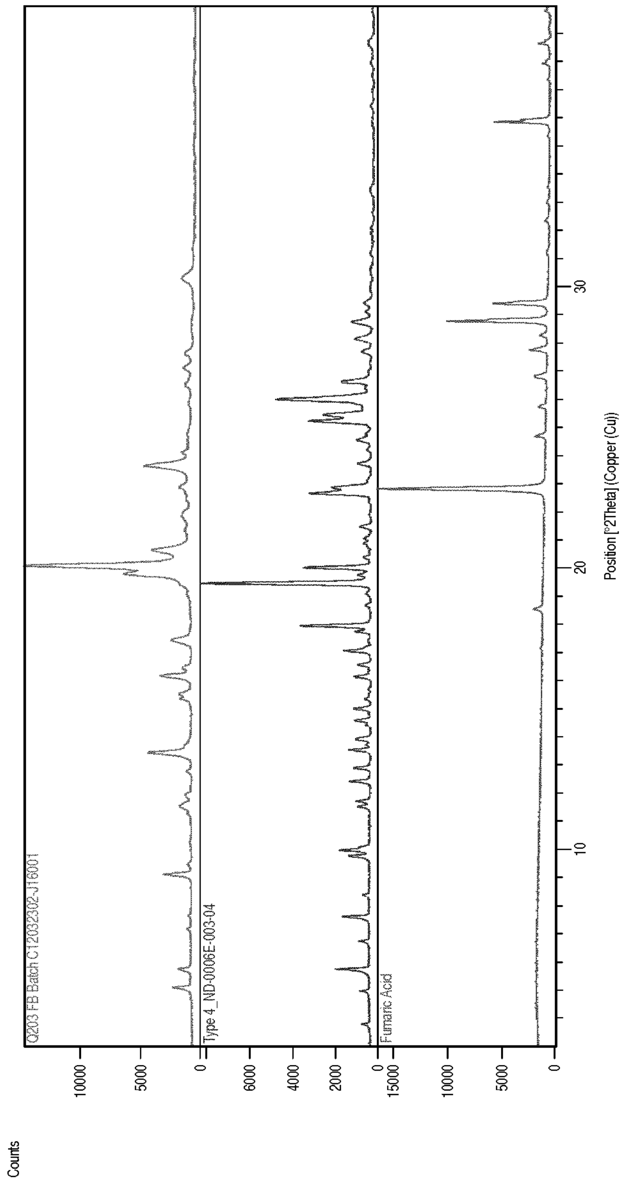
FIG. 27 shows XRPD patterns of Q203 free base (top trace), ND-0006E-003-04 (Type 4, middle trace) and fumaric acid (bottom trace).

Type 4 material was generated from slow evaporation experiments involving fumaric acid and Q203 free base (both 1:1 and 2:1 acid/API) in THF/MeOH. XRPD analysis of Type 4 solid (ND-0006E-003-04) showed the material was crystalline (FIG. 27) and $^1$H NMR analysis in acetone-$d_6$ showed no salt formation with residual MeOH (~0.5 molar eq.) (data not shown). This suggests that Type 4 is a potentially a co-crystal or polymorph of Q203 free base, possibly hemisolvated with MeOH.

5.5 Type 5 (Urea)

Figure 28:
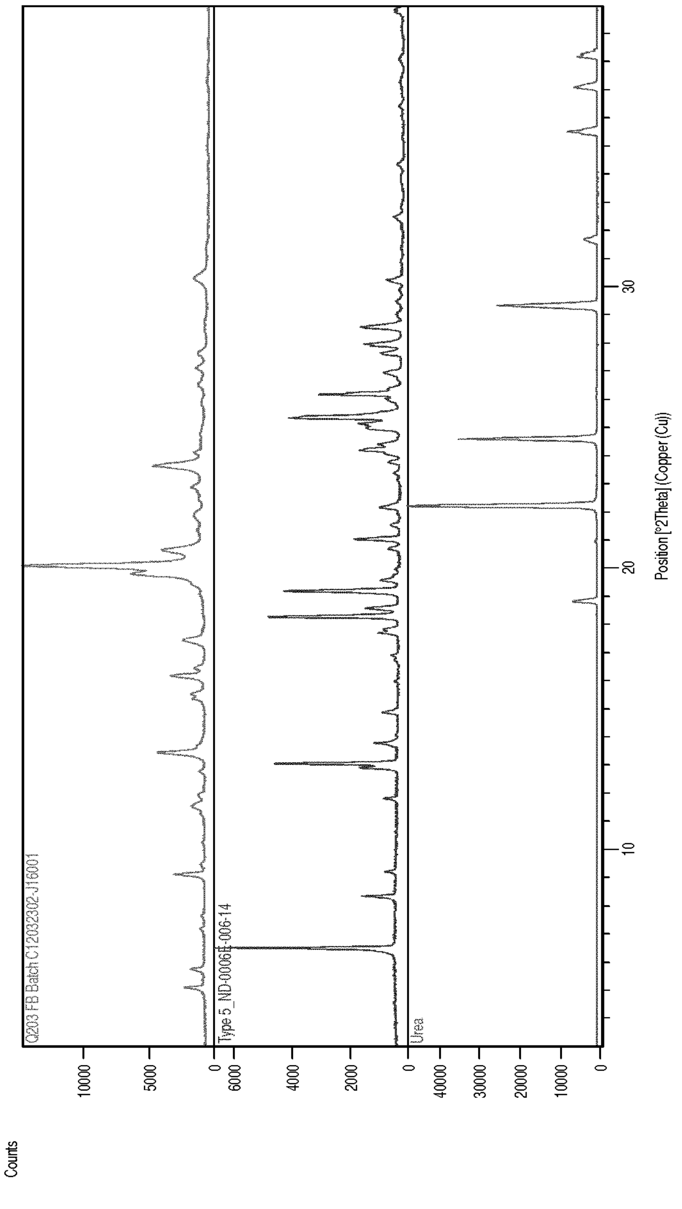
FIG. 28 shows XRPD patterns of Q203 free base (top trace), ND-0006E-006-14 (Type 5, middle trace) and urea (bottom trace).

Type 5 material was generated from experiments involving urea and Q203 free base (both 1:1 and 2:1 acid/API) in a mixture of THF/MeOH, MTBE and IPA. Experimental conditions leading to Type 5 solid are highlighted in Table 13. XRPD analysis of Type 5 solid (ND-0006E-006-14) showed the material was crystalline (FIG. 28). $^1$H NMR analysis of Type 5 material showed no peak shifting suggesting a salt has not been formed (data not shown) with no residual solvent. A DSC was carried out to determine if a Q203:urea co-crystal had been formed however the thermogram corresponded to a melt of the free base and urea. Further investigation would be required to determine whether Type 5 is a co-crystal.

TABLE 13

| Experimental conditions leading to Type 5 solid | | | | | |
|---|---|---|---|---|---|
| Sample No. (ND-0006E-) | Solvent | Antisolvent | Screen method | Acid:API (molar ratio) | Result |
| 004-14 | MTBE | none | slurry (20° C.) | 1:1 | solid |
| 006-14 | THF | methanol | slow evap | 2:1 | solid |
| 007-14 | IPA | none | slow evap/slurry (40° C.) | 2:1 | solid |

5.6 Type 6 (Benzenesulfonic)

Figure 29:
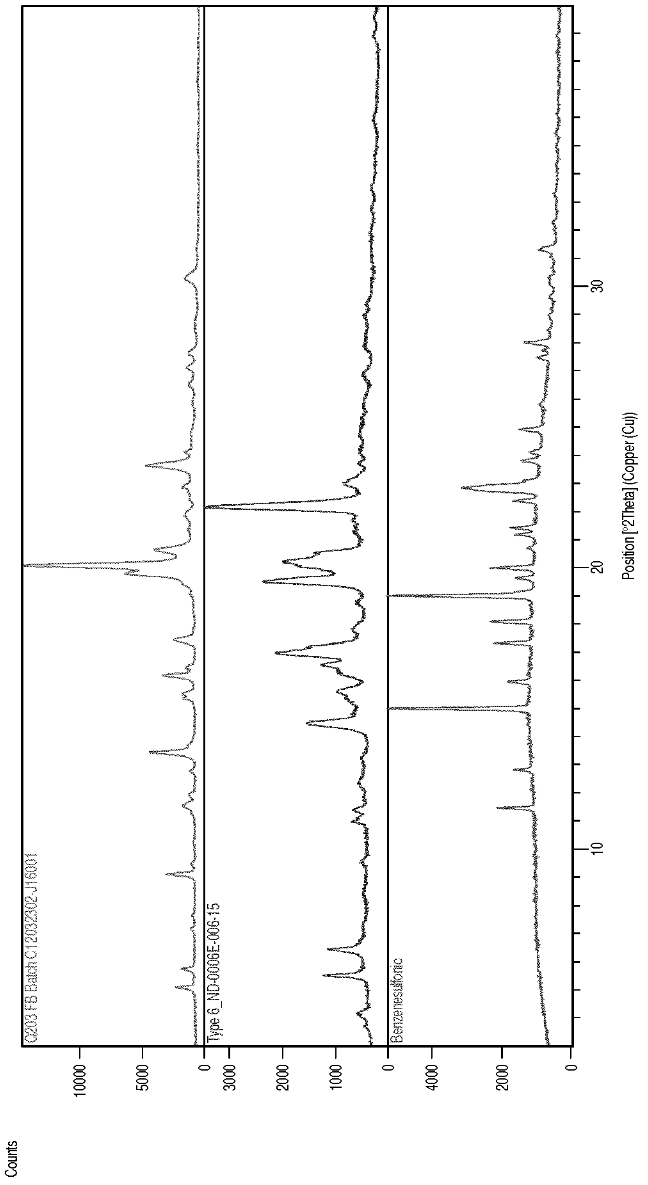
FIG. 29 shows XRPD patterns of Q203 free base (top trace), ND-0006E-006-15 (Type 6, bottom trace) and benzenesulfonic acid.

Type 6 material was isolated from a slow evaporation experiment using benzenesulfonic acid and Q203 free base (2:1 acid/API) in a mixture of THF/acetone. Type 6 was also observed as a mixture with Type 3. XRPD analysis of Type 6 solid (ND-0006E-006-15) showed the material was disordered crystalline (FIG. 29) and $^{1}H$ NMR analysis (data not shown) showed peak shifting suggesting salt formation, possibly with a 1:1 or 2:1 stoichiometry (to be confirmed) with ~0.25 molar eq. of THF.

5.7 Type 7 (p-Toluenesulfonic)

Figure 30:
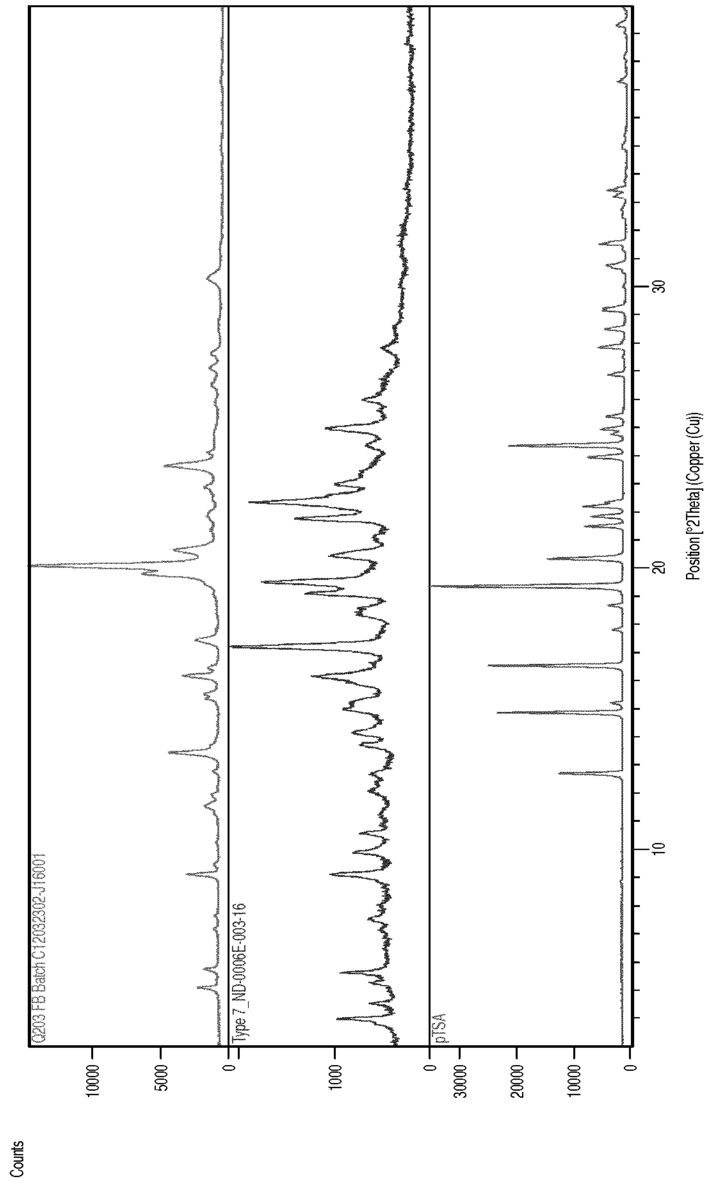
FIG. 30 shows XRPD patterns of Q203 free base (top trace), ND-0006E-003-16 (Type 7, middle trace) and pTSA (bottom trace).

Type 7 material was isolated from both a slow evaporation experiment using pTSA and Q203 free base (1:1 acid/API) in a mixture of THF/acetone and a sonication experiment using THF. XRPD analysis of Type 7 solid (ND-0006E-003-16) showed the material was crystalline (FIG. 30) and $^{1}H$ NMR analysis showed peak shifting suggesting salt formation with no residual solvent, possibly with a 1:1 (acid:API) stoichiometry (data not shown). It should be noted the presence of additional peaks.

5.8 Type 8 (p-Toluenesulfonic)

Figure 31:
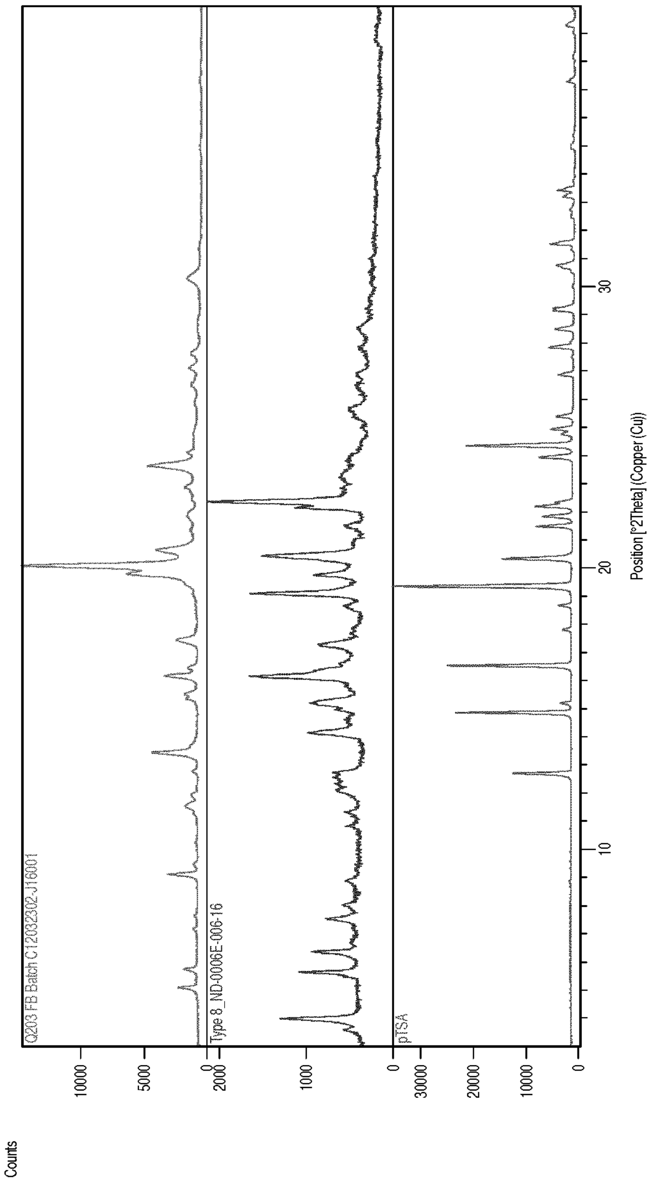
FIG. 31 shows XRPD patterns of Q203 free base (top trace), ND-0006E-006-16 (Type 8, middle trace) and pTSA (bottom trace).

Type 8 solid was generated from a slow evaporation experiment using pTSA and Q203 free base (2:1 acid/API) in a mixture of THF/acetone. XRPD analysis of Type 8 solid (ND-0006E-006-16) showed the material was crystalline (FIG. 31) and $^{1}H$ NMR analysis showed peak shifting with ~0.15 molar eq. of THF suggesting salt formation, possibly with a 2:1 stoichiometry (data not shown).

5.9 Type 9 (Ethane-1,2-Disulfonic Acid)

Figure 32:
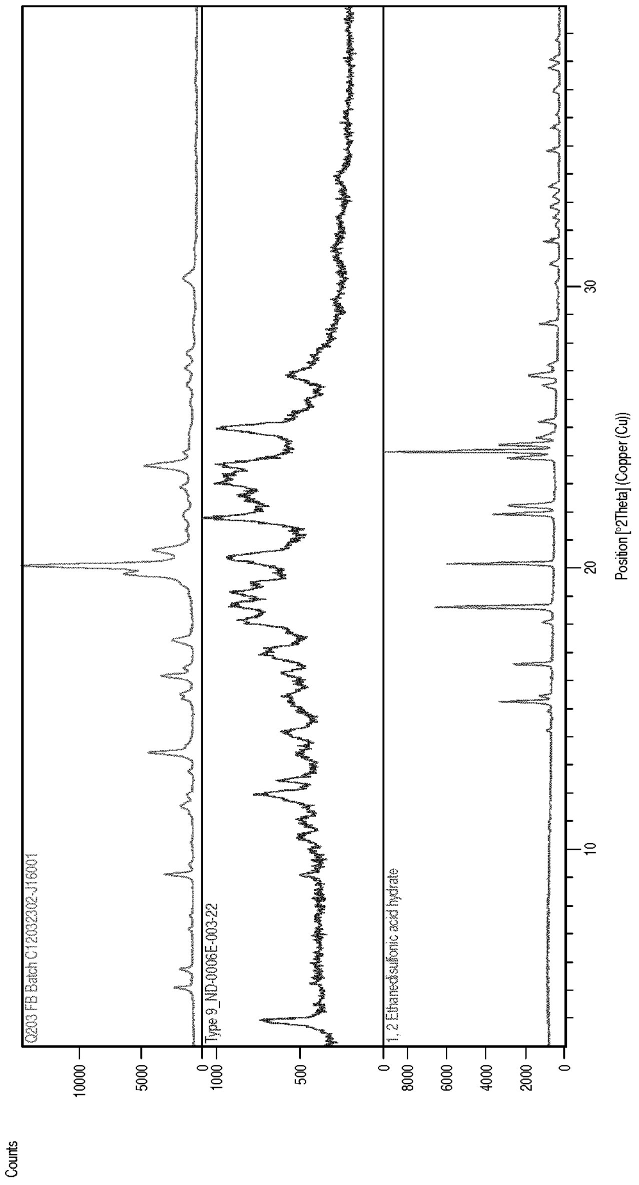
FIG. 32 shows XRPD patterns of Q203 free base (top trace), ND-0006E-003-22 (Type 9, middle trace) and EDSA (bottom trace).

Type 9 material was generated from experiments involving EDSA and Q203 free base (1:1 acid/API). Experimental conditions leading to Type 9 solid are highlighted in Table 14. XRPD analysis of Type 9 solid (ND-0006E-006-14) showed the material was crystalline (FIG. 32). $^{1}H$ NMR analysis showed peak shifting with ~0.07 molar eq. of MTBE suggesting salt formation, possibly with a 1:1 stoichiometry (data not shown).

TABLE 14

| Experimental conditions leading to Type 9 solid | | | | |
|---|---|---|---|---|
| Sample No. (ND-0006E-) | Solvent | Antisolvent | Screen method | Result |
| 003-22 | THF | acetone | slow evap | solid |
| 004-22 | MTBE | none | slurry (20° C.) | solid |
| 005-22 | THF | none | sonication | solid |

5.10 Type 10 (1,5-Napthalenedisulfonic Acid)

Figure 33:
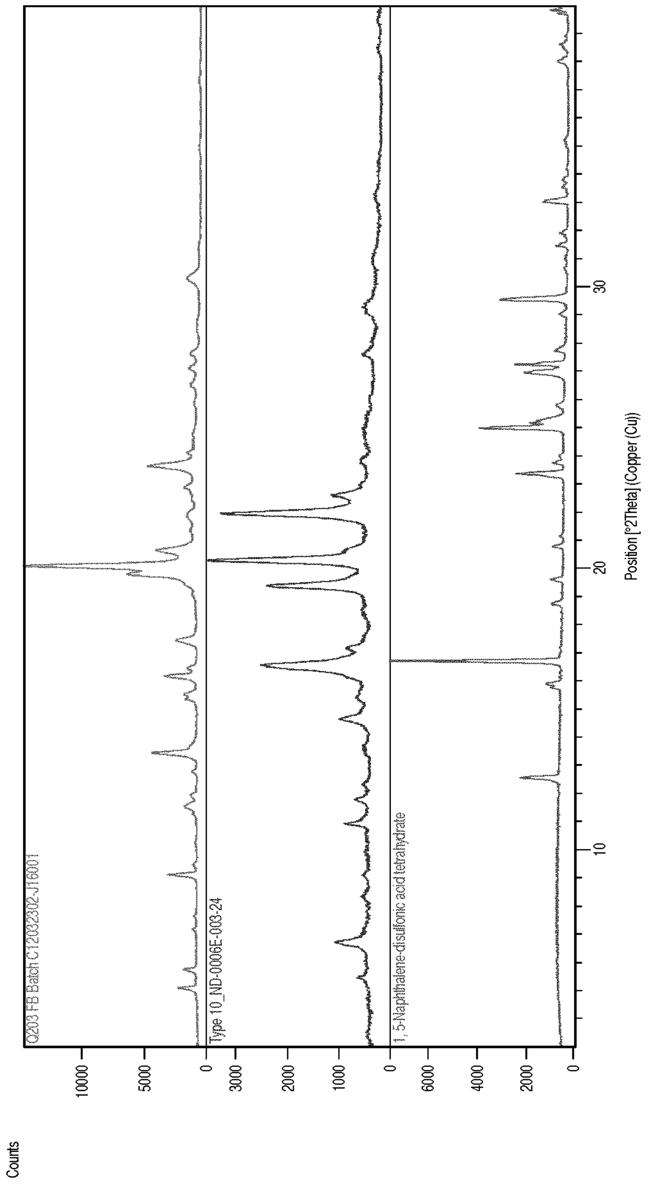
FIG. 33 shows XRPD patterns of Q203 free base (top trace), ND-0006E-003-24 (Type 10, middle trace) and NDSA (bottom trace).

Type 10 material was isolated from both a slow evaporation experiment using NDSA and Q203 free base (1:1 acid/API) in a mixture of THF/acetone and a sonication experiment using THF. XRPD analysis of Type 10 solid (ND-0006E-003-24) showed the material was crystalline (FIG. 33) and $^{1}H$ NMR analysis showed peak shifting suggesting salt formation, with a likely 2:1 (acid:API) stoichiometry (data not shown). Residual THF (~0.5 molar eq.) also suggests a possible THF hemisolvate of Q203 salt.

5.11 Type 11 (1,5-Napthalenedisulfonic Acid)

Figure 34:
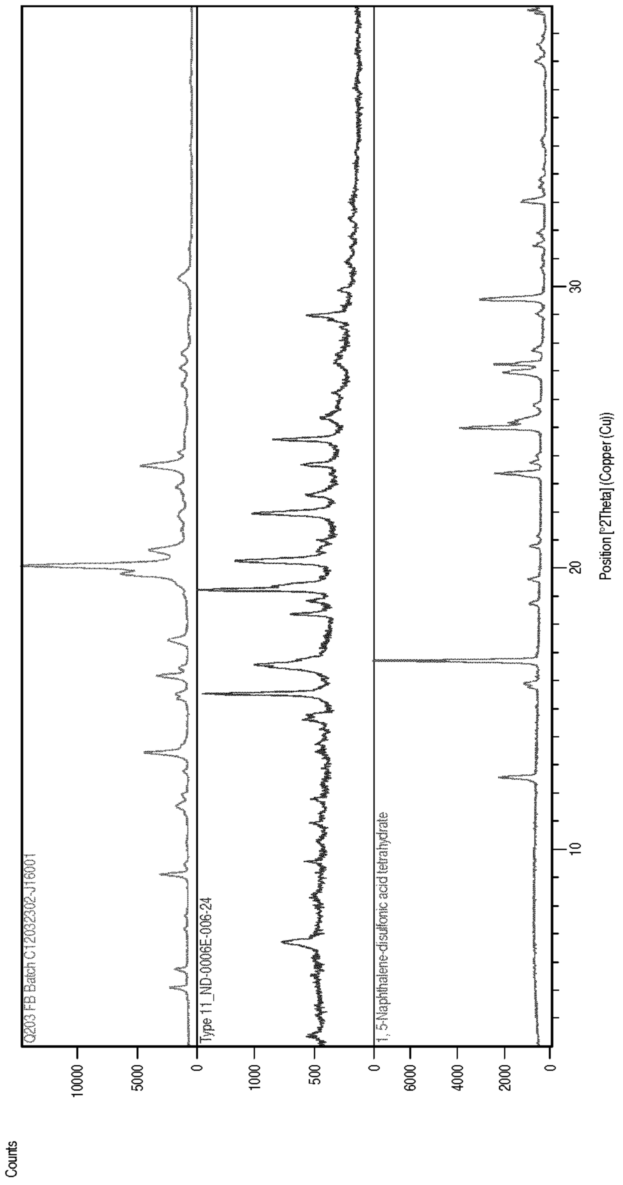
FIG. 34 shows XRPD patterns of Q203 free base (top trace), ND-0006E-006-24 (Type 10, middle trace) and NDSA (bottom trace).

Type 11 material was generated from a slow evaporation experiment using NDSA and Q203 free base (2:1 acid/API) in a mixture of THF/acetone. XRPD analysis of Type 11 solid (ND-0006E-006-$2_4$) showed the material was crystalline and the pattern was similar to Type 10 with minor differences (FIG. 34). $^{1}H$ NMR analysis showed peak shifting suggesting salt formation (data not shown). Residual THF (~0.7 molar eq.) also suggests a possible THF solvate. The stoichiometry of this salt has not been determined due to the presence of free acid.

5.12 Type 12 (Benzenesulfonic)

Figure 35:
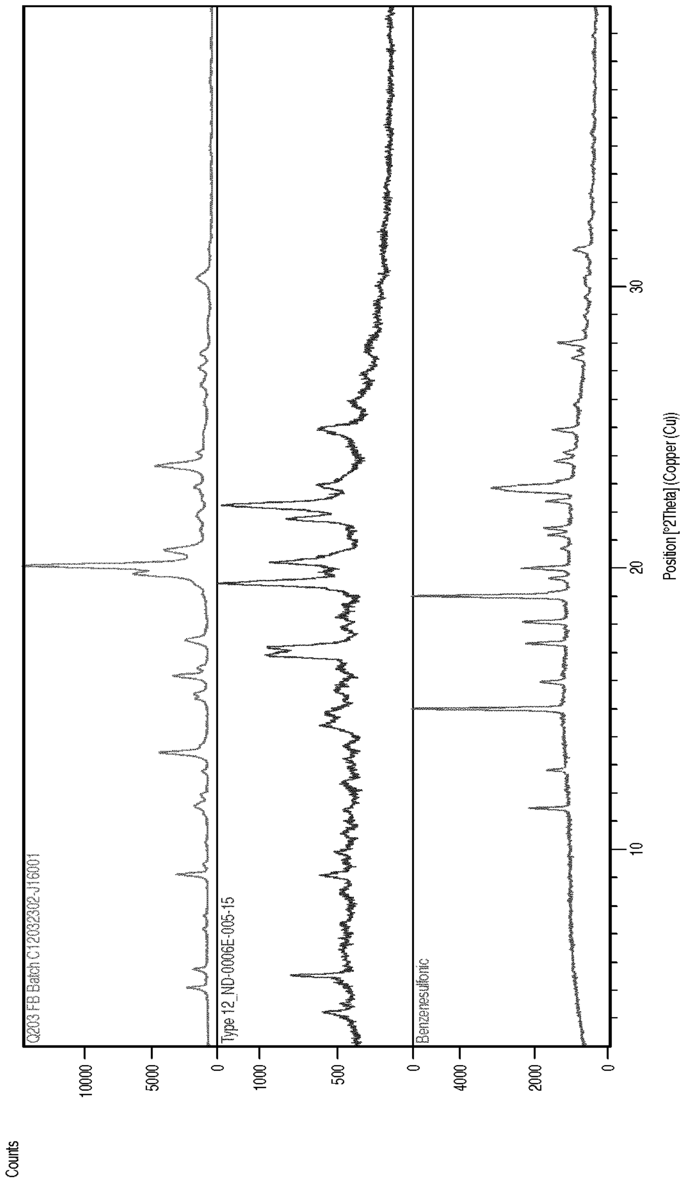
FIG. 35 shows XRPD patterns of Q203 free base (top trace), ND-0006E-005-15 (Type 12, middle trace) and BSA (bottom trace).

Type 12 material was isolated from a sonication experiment using BSA and Q203 free base (1:1 acid/API) in THF. XRPD analysis of Type 12 solid (ND-0006E-005-15) showed the material was crystalline (FIG. 35). Proton NMR analysis showed peak shifting, ~0.03 molar eq. of THF suggesting salt formation with a 1:1 stoichiometry (data not shown).

5.13 Type 13 (Furoic)

Figure 36:
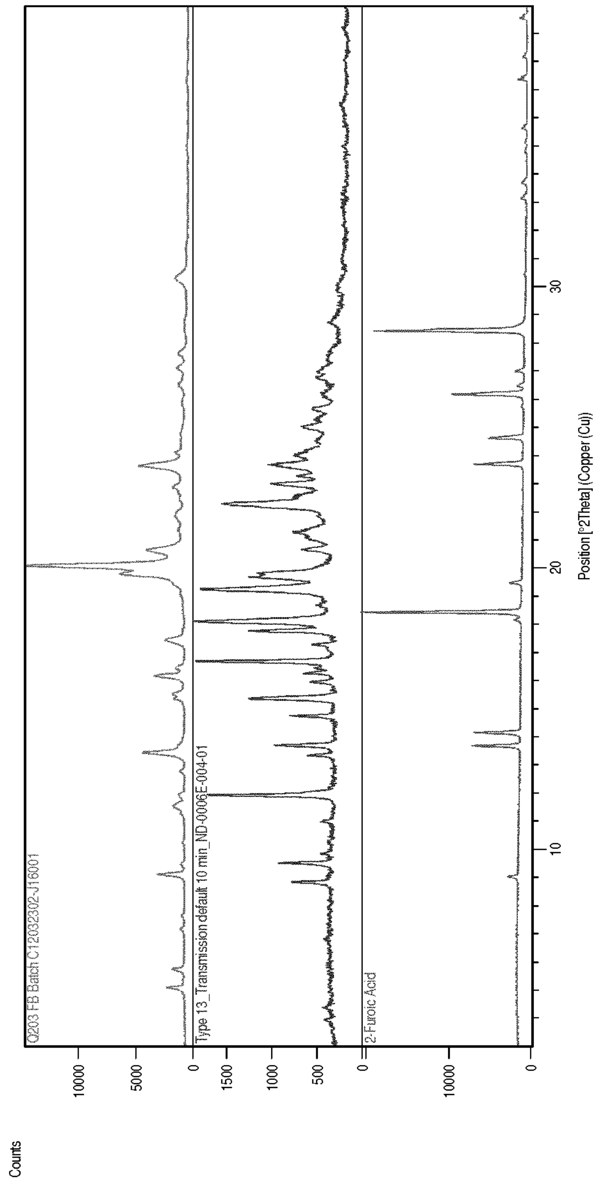
FIG. 36 shows XRPD patterns of Q203 free base (top trace), ND-0006E-004-01 (Type 13, middle trace) and 2-furoic acid (bottom trace).

Type 13 material was generated from experiments involving furoic acid and Q203 free base (1:1 and 2:1 acid/API). Experimental conditions leading to Type 13 solid are highlighted in Table 15. XRPD analysis of Type 13 solid (ND-0006E-004-01) showed the material was crystalline (FIG. 36). $^{1}H$ NMR analysis in DMSO-$d_6$ showed no peak shifting or residual solvent suggesting a possible polymorph of the free base, a Q203:furoic acid co-crystal or a degradant (data not shown).

TABLE 15

| Experimental conditions leading to Type 13 solid | | | | | |
|---|---|---|---|---|---|
| Sample No. (ND-0006E-) | Solvent | Anti-solvent | Screen method | Acid:API (molar ratio) | Result |
| 004-01 | MTBE | none | slurry (20° C.) | 1:1 | solid |
| 005-01 | THF | none | sonication | 1:1 | solid |
| 007-01 | THF | methanol | slow evap/slurry (40° C.) | 2:1 | solid |

5.14 Type 14 (Citric)

Figure 37:
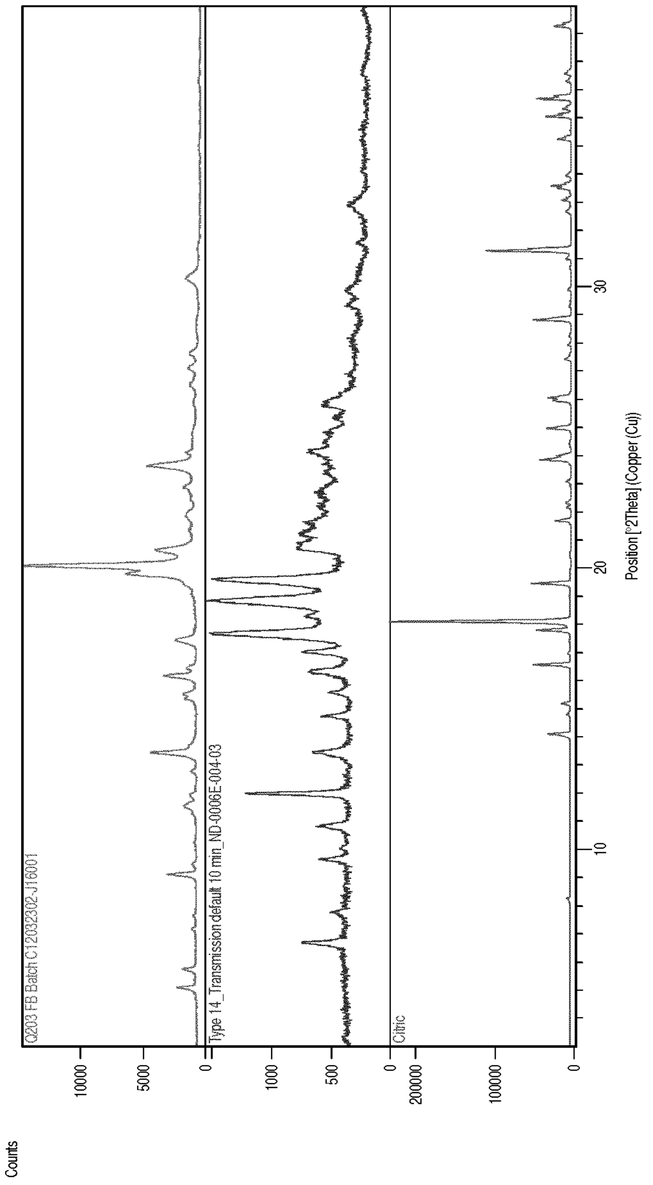
FIG. 37 shows XRPD patterns of Q203 free base (top trace), ND-0006E-004-03 (Type 14, middle trace) and citric acid (bottom trace).

Type 14 material was generated from an ambient temperature slurrying experiment using citric acid and Q203 free base (1:1 acid/API) in MTBE for 7 days. XRPD analysis of Type 14 solid (ND-0006E-004-03) showed the material was crystalline (FIG. 37) and $^{1}H$ NMR analysis showed no peak shifting or residual solvent suggesting a possible polymorph of the free base or a Q203:citric acid co-crystal (data not shown).

5.15 Type 15 (Fumaric)

Figure 38:
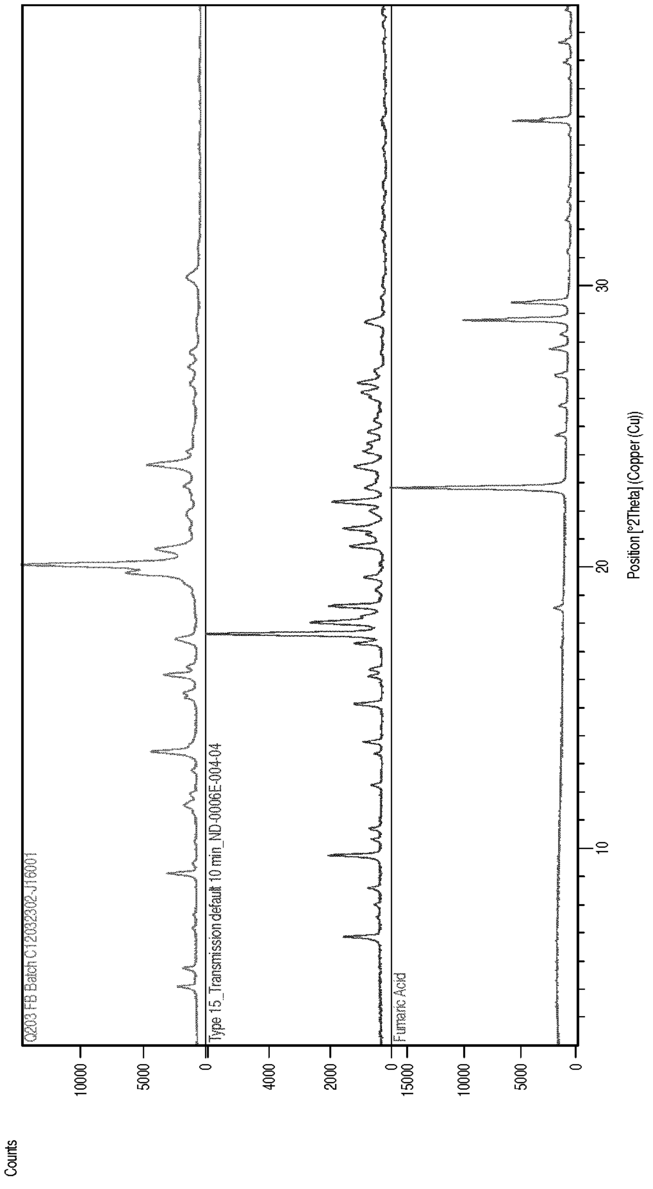
FIG. 38 shows XRPD patterns of Q203 free base (top trace), ND-0006E-004-04 (Type 14, middle trace) and fumaric acid (bottom trace).

Type 15 material was isolated from slurrying experiments using fumaric acid and Q203 free base (1:1 acid/API) in MTBE (20° C.) and IPA (40° C.). XRPD analysis of Type 15 solid (ND-0006E-004-04) showed the material was crystalline (FIG. 38) and $^{1}H$ NMR analysis showed no peak shifting or residual solvent suggesting a possible polymorph of the free base or a Q203:fumaric acid co-crystal (~0.7 molar eq. of fumaric acid) (data not shown).

5.16 Type 16 (Ketoglutaric)

Figure 39:
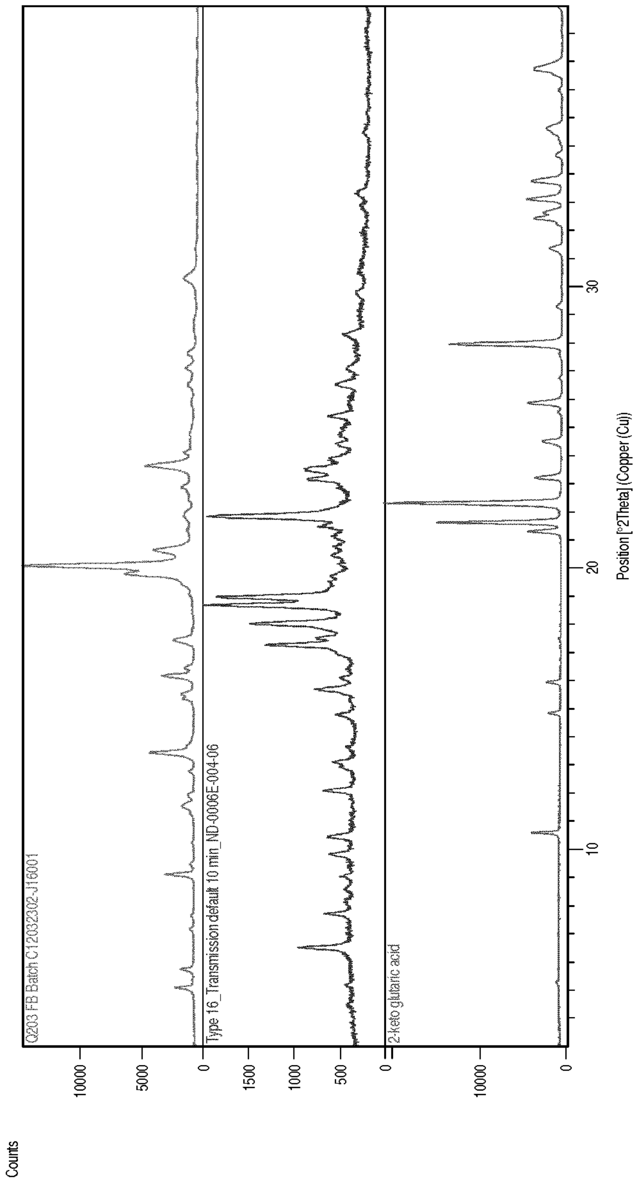
FIG. 39 shows XRPD patterns of Q203 free base (top trace), ND-0006E-004-06 (Type 16, middle trace) and ketoglutaric acid (bottom trace).

Type 16 material was generated from an ambient temperature slurrying experiment using ketoglutaric acid and Q203 free base (1:1 acid/API) in MTBE for 7 days. XRPD analysis of Type 16 solid (ND-0006E-004-06) showed the material was crystalline (FIG. 39). Proton NMR analysis showed possibly peak shifting at 2.9 ppm, ~0.02 molar eq. of MTBE. Further analysis would need to be carried out in order to determine the nature of this Type (data not shown).

5.17 Type 17 (1,5-Napthalenedisulfonic Acid)

Figure 40:
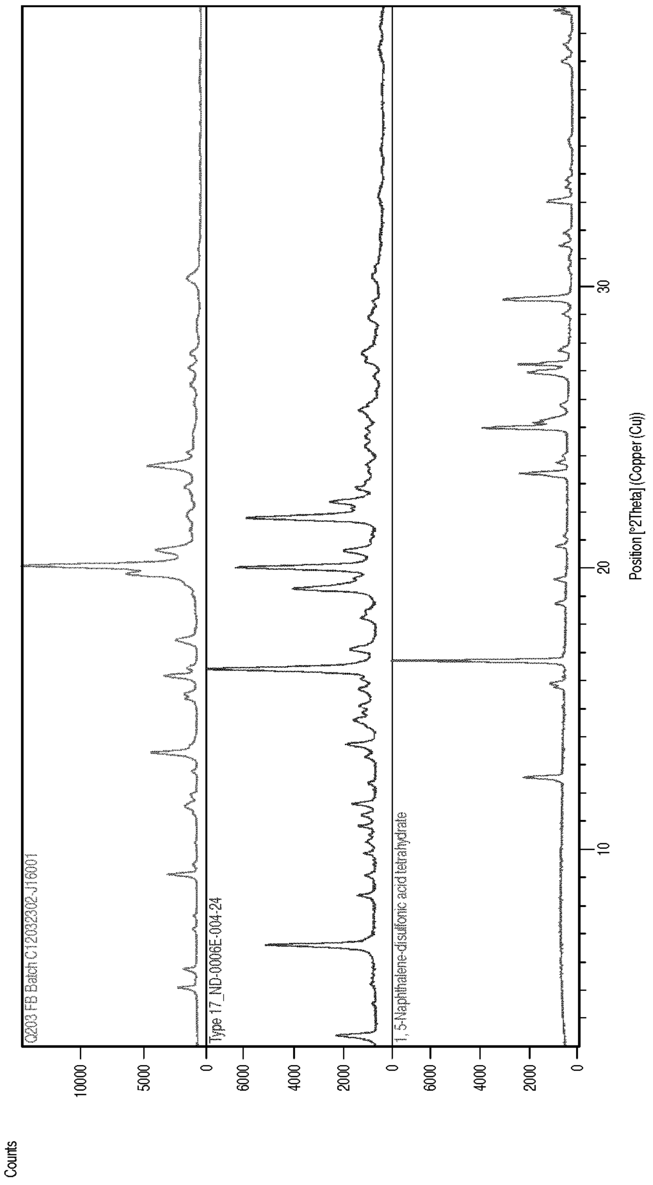
FIG. 40 shows XRPD patterns of Q203 free base (top trace), ND-0006E-004-24 (Type 17, middle trace) and NDSA (bottom trace).

Type 17 material was generated from an ambient temperature slurrying experiment using NDSA and Q203 free base (1:1 acid/API) in MTBE for 7 days. XRPD analysis of Type 17 solid (ND-0006E-004-$2_4$) showed the material was crystalline and the pattern was similar to Type 11 with both additional and missing peaks (FIG. 40). $^1$H NMR analysis showed peak shifting with ~0.08 molar eq. of MTBE suggesting salt formation with likely a 2:1 acid/API stoichiometry (data not shown).

5.18 Type 18 (Maleic)

Figure 41:
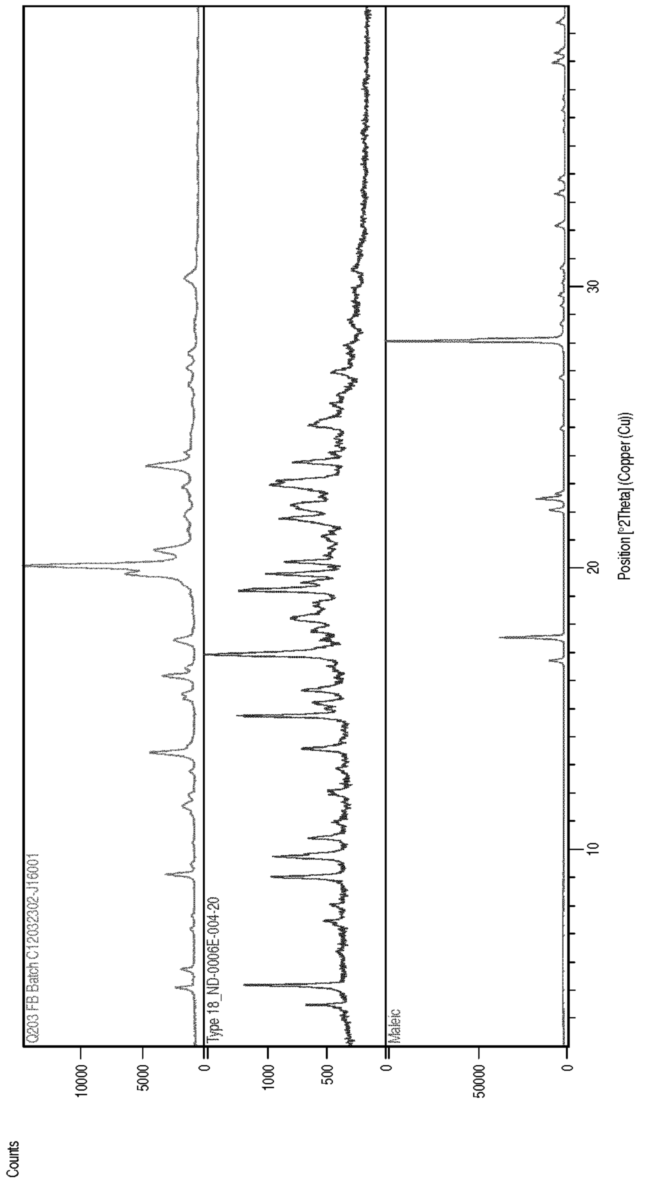
FIG. 41 shows XRPD patterns of Q203 free base (top trace), ND-0006E-004-20 (Type 18, middle trace) and maleic acid (bottom trace).

Type 18 material was isolated from an ambient temperature slurrying experiment using maleic acid and Q203 free base (1:1 acid/API) in MTBE for 7 days. XRPD analysis of Type 18 solid (ND-0006E-004-20) showed the material was crystalline and the pattern was similar to Type 19 with an additional peak present in the diffractogram (FIG. 41). $^1$H NMR analysis showed peak shifting suggesting salt formation, with a likely 1:1 (acid:API) stoichiometry and residual MTBE (~0.2 eq) (data not shown).

5.19 Type 19 (Gentisic)

Figure 42:
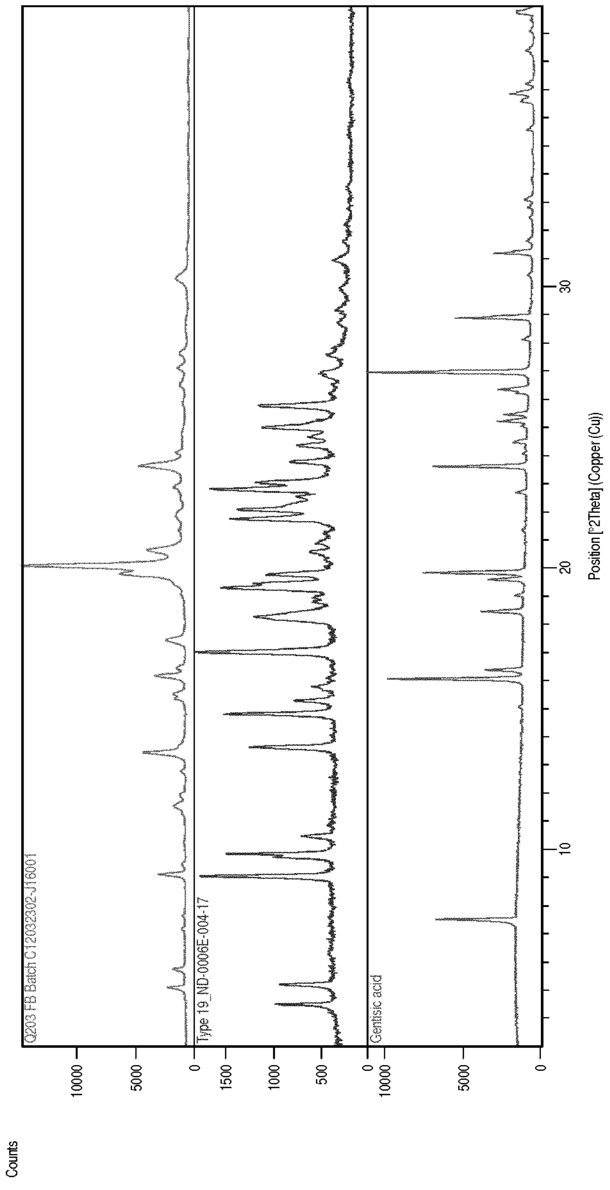
FIG. 42 shows XRPD patterns of Q203 free base (top trace), ND-0006E-004-17 (Type 19, middle trace) and gentisic acid (bottom trace).

Type 19 material was generated from an ambient temperature slurrying experiment using maleic acid and Q203 free base (1:1 acid/API) in MTBE for 7 days. XRPD analysis of Type 19 solid (ND-0006E-004-17) showed the material was crystalline and the pattern showed some similarity to Type 3 (FIG. 42). $^1$H NMR analysis showed no peak shifting with some residual MTBE (0.1 molar eq.) and free acid (0.2 molar eq.) suggesting a possible polymorph of the free base or a Q203:gentisic acid co-crystal (data not shown).

5.20 Type 20 (p-Toluenesulfonic)

Figure 43:
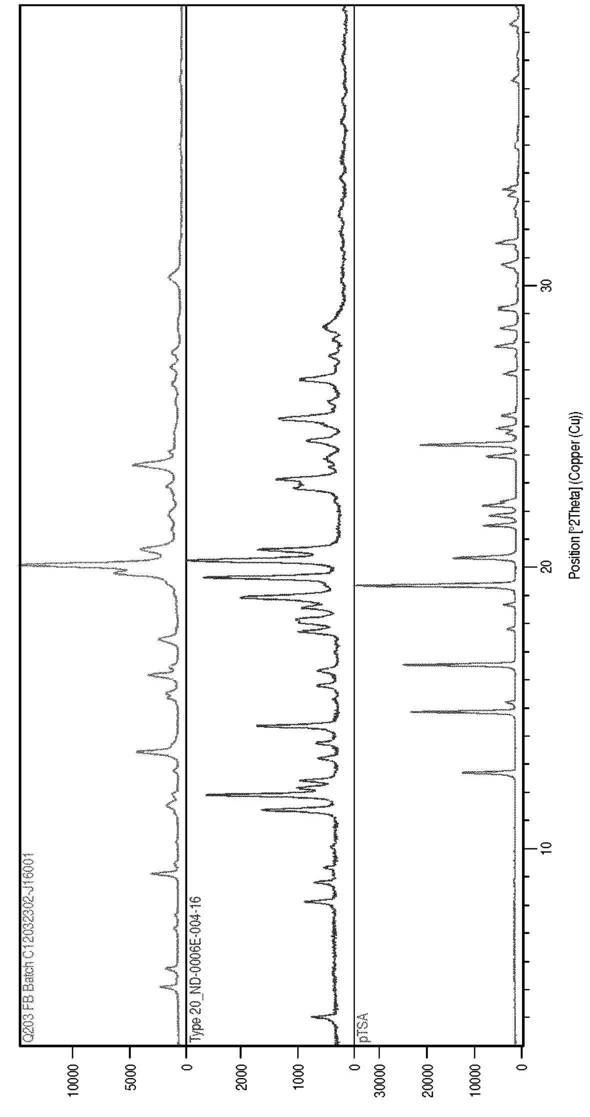
FIG. 43 shows XRPD patterns of Q203 free base (top trace), ND-0006E-004-16 (Type 20, middle trace) and pTSA (bottom trace).

Type 20 material was isolated from an ambient temperature slurrying experiment using pTSA and Q203 free base (1:1 acid/API) in MTBE for 7 days. XRPD analysis of Type 20 solid (ND-0006E-004-16, FIG. 43 showed the material was crystalline and 1H NMR analysis showed peak shifting with trace amounts of residual MTBE (0.01 molar eq.) suggesting salt formation with a 1:1 acid/API stoichiometry (data not shown).

5.21 Type 21 (Tartaric)

Figure 44:
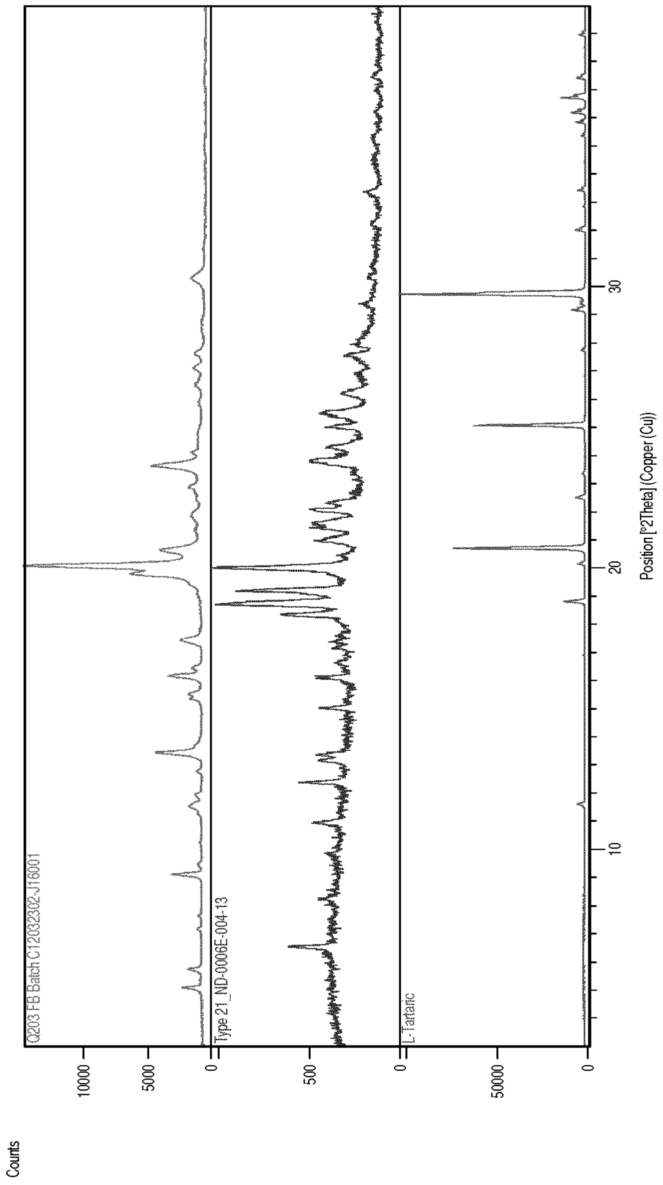
FIG. 44 shows XRPD patterns of Q203 free base (top trace), ND-0006E-004-13 (Type 21, middle trace) and tartaric acid (bottom trace).

Type 21 material was isolated from slurrying experiments using tartaric acid and Q203 free base (1:1 and 2:1 acid/API) in MTBE and IPA (20° C. and 40° C. respectively). XRPD analysis of Type 21 solid (ND-0006E-004-$1_3$) showed the material was crystalline (FIG. 44) and $^1$H NMR analysis (data not shown) of solid (ND-0006E-007-13) showed no peak shifting or residual solvent with ~0.6 molar eq. of tartaric acid and an unknown peak at 8.1 ppm. TG/DTA analysis showed a weight loss of ~0.4% prior the melt observed at onset temperature of 168° C. These results suggests a possible co-crystal or polymorph of Q203 free base.

5.22 Type 22 (Succinic)

Figure 45:
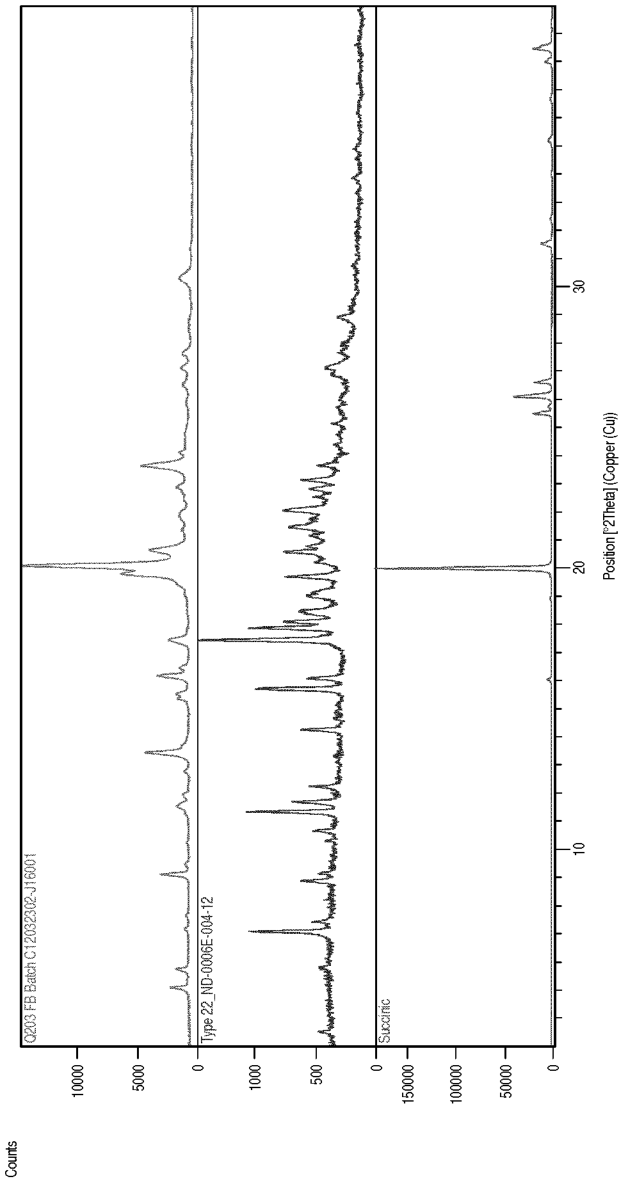
FIG. 45 shows XRPD patterns of Q203 free base (top trace), ND-0006E-004-12 (Type 22, middle trace) and succinic acid (bottom trace).

Type 22 material was isolated from an ambient temperature slurrying experiment using succinic acid and Q203 free base (1:1 acid/API) in MTBE for 7 days. XRPD analysis of Type 20 solid (ND-0006E-004-12, FIG. 45 showed the material was crystalline and $^1$H NMR analysis showed no peak shifting with trace amounts of residual MTBE (0.003 molar eq.) and ~1 molar eq. of succinic acid suggesting a possible co-crystal or polymorph of Q203 free base (data not shown).

5.23 Type 23 (Mandelic)

Figure 46:
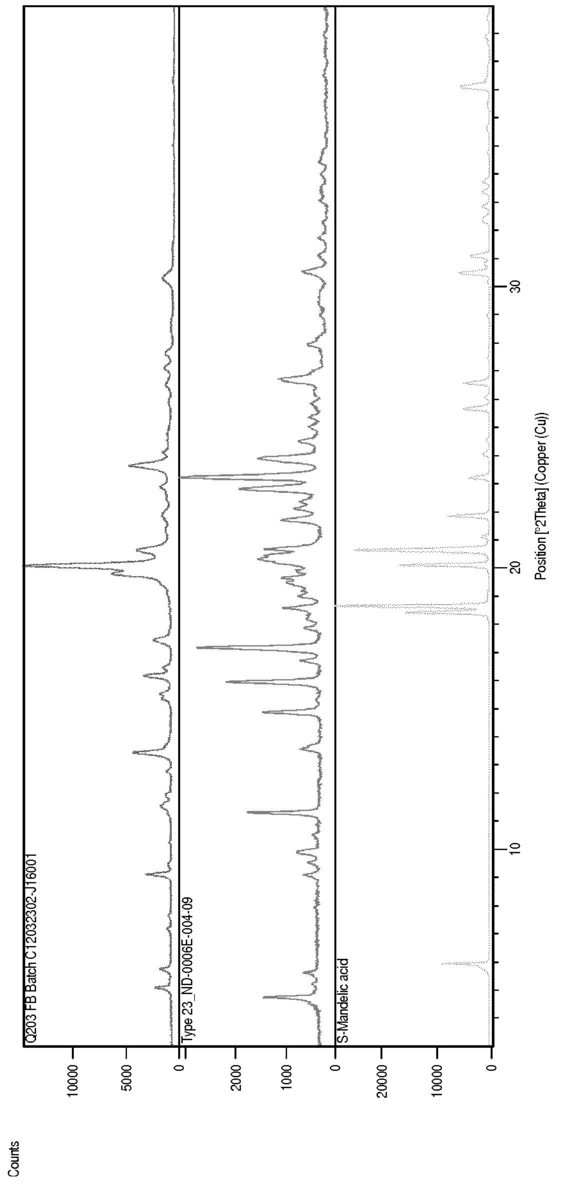
FIG. 46 shows XRPD patterns of Q203 free base (top trace), ND-0006E-004-12 (Type 22, bottom trace) and mandelic acid (bottom trace).

Type 23 material was generated from experiments involving mandelic acid and Q203 free base (1:1 and 2:1 acid/API). Experimental conditions leading to Type 23 solid are highlighted in Table 16. XRPD analysis of Type 23 solid (ND-0006E-004-01) showed the material was crystalline (FIG. 46) with additional peaks observed in sample ND-0006E-007-09. $^1$H NMR analysis of solid (ND-0006E-004-09) showed no peak shifting, trace amounts of residual solvent (0.01 molar eq.) and ~0.8 molar eq. of mandelic acid which may suggest possible polymorph or mandelic acid co-crystal of Q203 free base (data not shown).

TABLE 16

Experimental conditions leading to Type 23 solid

| Sample No. (ND-0006E-) | Solvent | Antisolvent | Screen method | Acid:API (molar ratio) | Result |
|---|---|---|---|---|---|
| 004-09 | MTBE | none | slurry (20° C.) | 1:1 | solid |
| 005-09 | THF | none | sonication | 1:1 | solid |
| 007-09 | IPA | none | slow evap/slurry (40° C.) | 2:1 | solid |

5.24 Type 24 (Malic)

Figure 47:
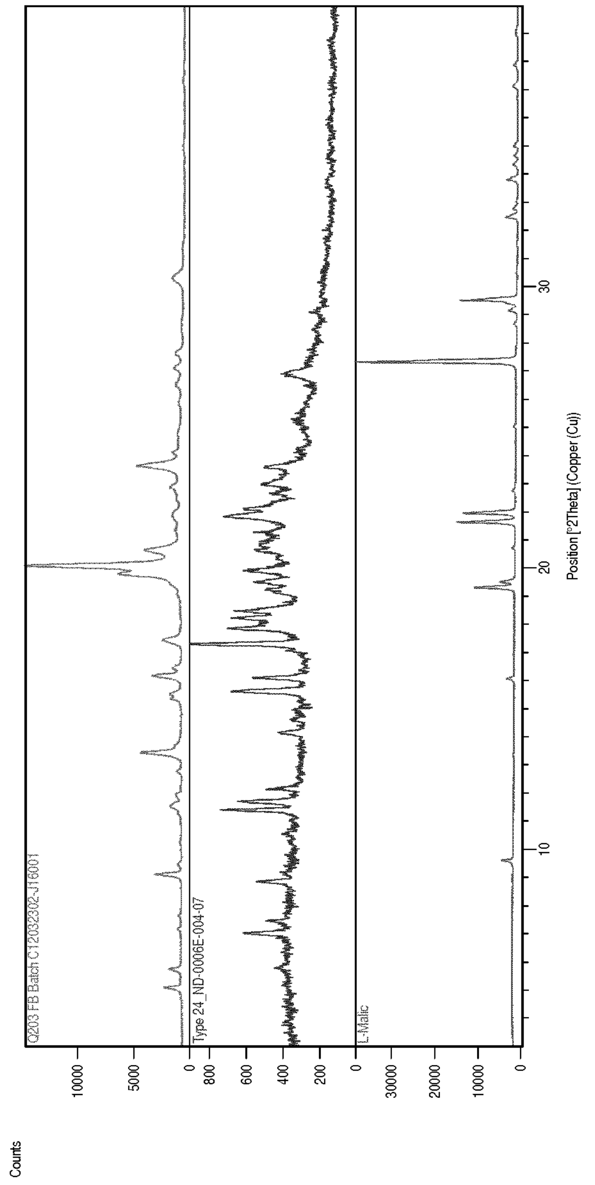
FIG. 47 shows XRPD patterns of Q203 free base (top trace), ND-0006E-004-07 (Type 24, middle trace) and malic acid (bottom trace).

Type 24 material was isolated from an ambient temperature slurrying experiment using malic acid and Q203 free base (1:1 acid/API) in MTBE and a sonication experiment using THF. XRPD analysis of Type 24 solid (ND-0006E-004-07) showed the material was disordered crystalline (FIG. 47) and $^1$H NMR analysis of solid (ND-0006E-005-07) showed no peak shifting or residual solvent, with 1 molar eq. of malic acid which may suggest a possible polymorph or malic acid co-crystal of Q203 free base (data not shown).

5.25 Type 25

Figure 48:
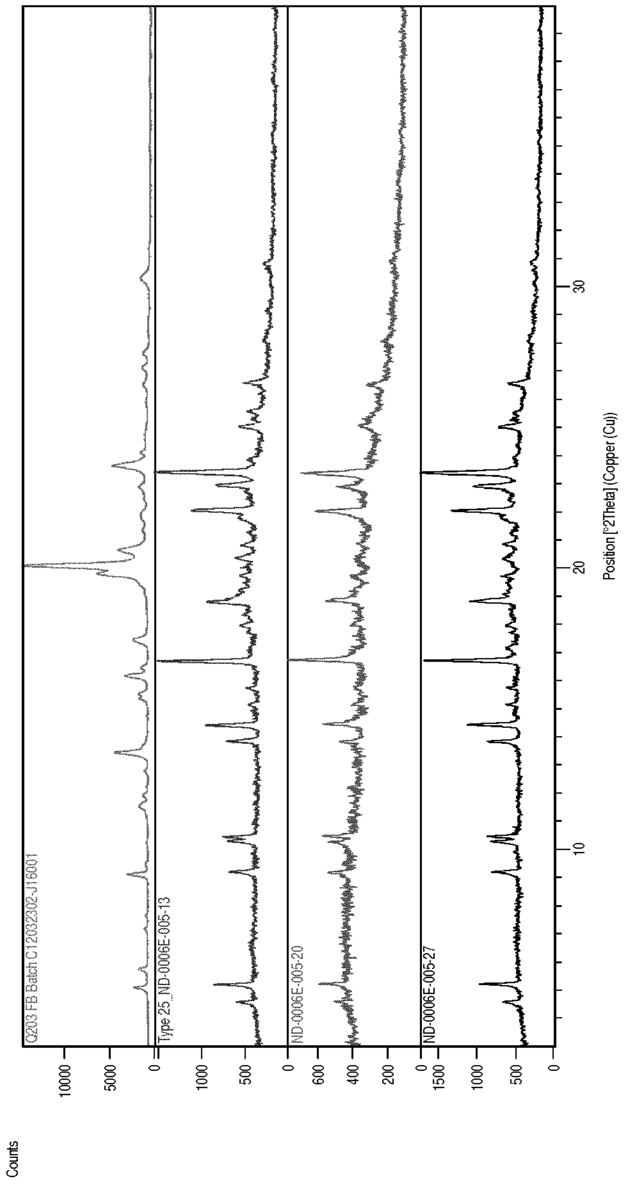
FIG. 48 shows XRPD patterns of Q203 free base (top trace), ND-0006E-005-13/20/27 (Type 25, $2^{nd}$/$3^{rd}$/bottom trace).

Type 25 material was generated from sonication experiments involving various acids and Q203 free base (1:1 acid/API) in THF. Experimental conditions leading to pure Type 25 and Type 25 mixtures (with Type 3) are highlighted in Table 17. XRPD analysis of pure Type 25 solid (ND-0006E-005-13,20,27) showed the material was crystalline (FIG. 48). As this Type was obtained from different coformers using THF, Type 25 is a likely a polymorph of Q203 free base and possibly solvated (THF).

It should be noted that proton NMR analysis of Type 25 material (ND-0006E-005-20) showed peak shifting suggesting salt formation (1:1 acid/API) with ~0.5 molar eq. of THF which may indicate a possible hemi-solvate of the Q203 maleate salt (data not shown). This may be explained by the formation of a salt in-situ during preparation of the sample in deuterated methanol for NMR spectroscopy analysis.

TABLE 17

Experimental conditions leading to Type 25 solid (pure and mixtures)

| Salt former | Sample No. (ND-0006E-) | Solvent | Anti-solvent | Acid:API (molar ratio) | Result | XRPD |
|---|---|---|---|---|---|---|
| maleic | 005-20 | THF | none | sonication | solid | Type 25 |
| saccharin | 005-27 | THF | none | sonication | solid | Type 25 |
| tartaric (L) | 005-13 | THF | none | sonication | solid | Type 25 |
| citric | 005-03 | THF | none | sonication | solid | Type 25 + Type 3 |
| gentisic | 005-17 | THF | none | sonication | solid | Type 25 + Type 3 |
| HCl | 005-18 | THF | none | sonication | solid | Type 25 + Type 3 |
| malonic | 005-08 | THF | none | sonication | solid | Type 25 + Type 3 |
| oxalic | 005-10 | THF | none | sonication | solid | Type 25 + Type 3 |
| phosphoric | 005-26 | THF | none | sonication | solid | Type 25 + Type 3 |
| pyroglutamic (L) | 005-11 | THF | none | sonication | solid | Type 25 + Type 3 |
| saccharin | 003-27 | THF | acetone | slow evap | solution/solid | Type 25 + Type 3 |

5.26 Type 26 (1,5-Napthalenedisulfonic Acid)

Figure 49:
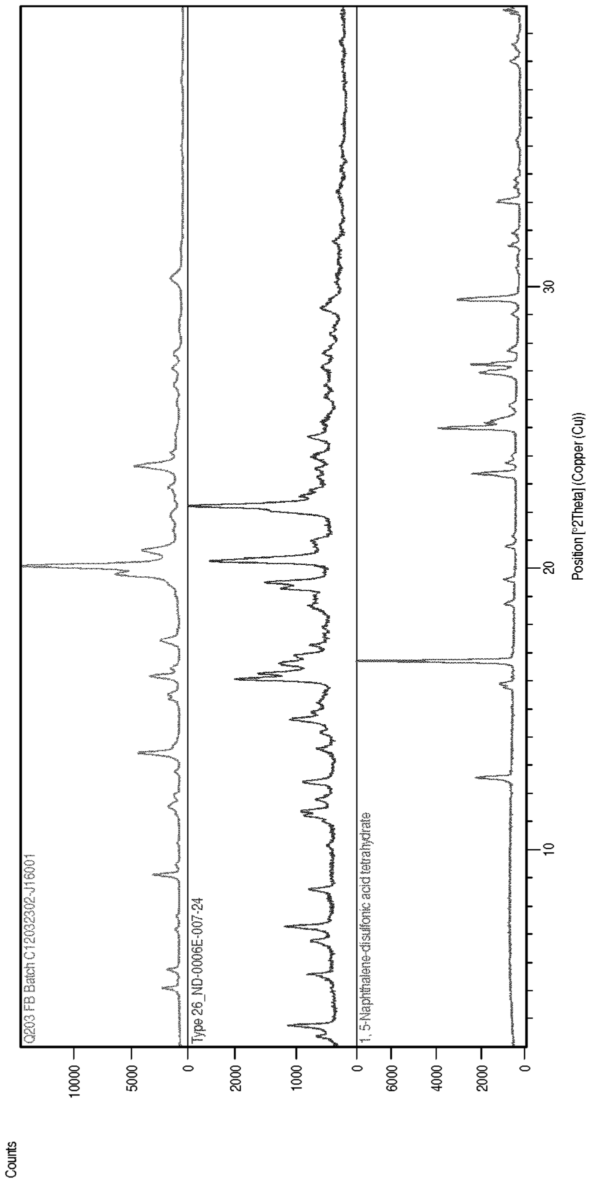
FIG. 49 shows XRPD patterns of Q203 free base (top trace), ND-0006E-007-24 (Type 26, middle trace) and NDSA (bottom trace).

Type 26 material was generated from a slow evaporation followed by high temperature slurrying experiment (40° C.) using NDSA and Q203 free base (2:1 acid/API) in IPA for 7 days. XRPD analysis of Type 26 solid (ND-0006E-007-24, FIG. 49) showed the material was crystalline and proton NMR spectroscopy shows peak shifting suggesting salt formation (data not shown) with ~0.04 molar eq. of IPA. The stoichiometry needs to be confirmed.

5.27 Type 27 (Gentisic)

Figure 50:
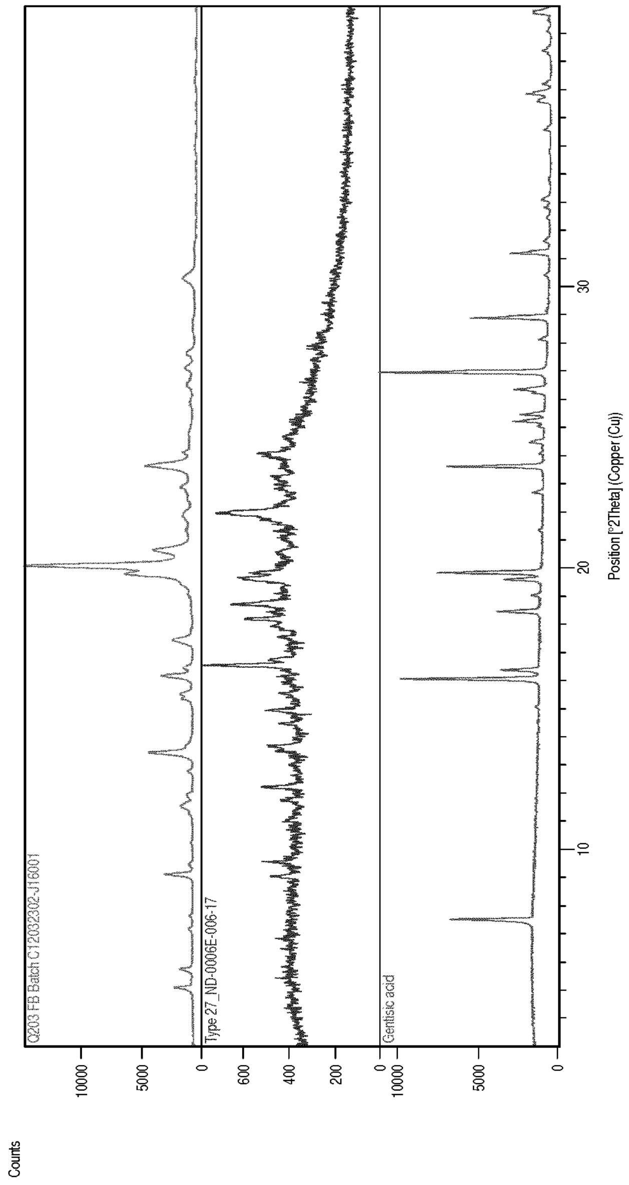
FIG. 50 shows XRPD patterns of Q203 free base (top trace), ND-0006E-006-17 (Type 27, middle trace) and gentisic acid (bottom trace).

Type 27 solid was generated from a slow evaporation experiment using gentisic acid and Q203 free base (2:1 acid/API) in a mixture of THF/methanol. XRPD analysis of Type 27 solid (ND-0006E-006-17) showed the material was disordered crystalline (FIG. 50) and $^1$H NMR analysis showed no peak shifting with ~0.5 molar eq. of THF, ~2 mol. eq. of co-former suggesting a possible hemisolvate of THF of gentisic co-crystal or polymorph of Q203 free base (data not shown).

5.28 Type 28 (Galactaric)

Figure 51:
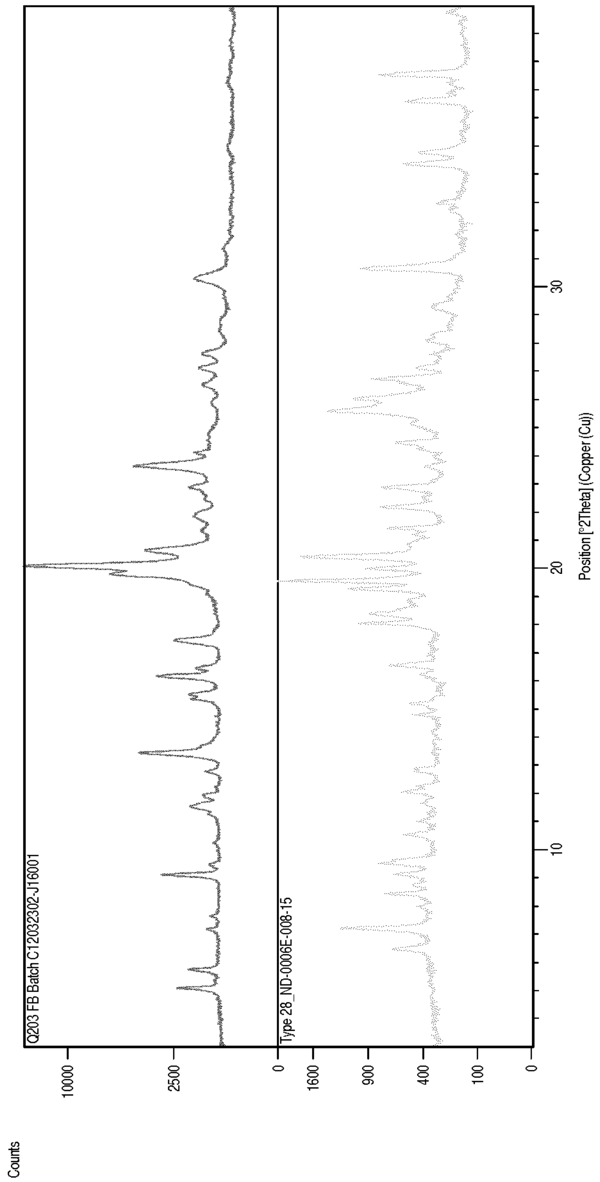
FIG. 51 shows XRPD patterns of Q203 free base (top trace), ND-0006E-008-15 (Type 28, bottom trace).

Type 28 material was isolated from two LAG experiments using galactaric and gluconic acid and Q203 free base 1:1 acid:API) in a mixture of IPA/water and acetone respectively. XPRD analysis of Type 28 (ND-0006E-008-15) showed the material was disordered crystalline (FIG. 51). Proton NMR analysis (data not shown) showed no peak shifting, ~0.07 molar eq. of IPA. TG/DTA results showed multiple endothermic events. Type 28 is likely a polymorph of the free base as obtained from different co-formers.

5.29 Type 29 (Ketoglutaric)

Figure 52:
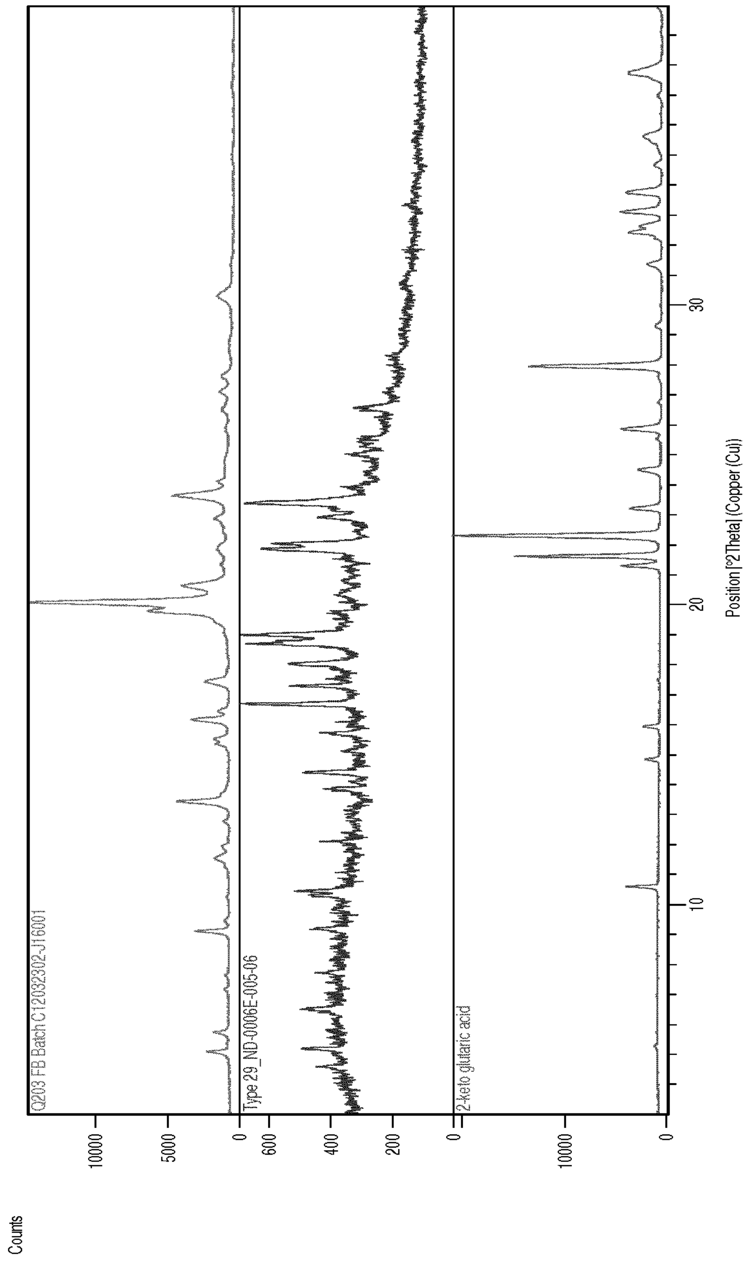
FIG. 52 shows XRPD patterns of Q203 free base (top trace), ND-0006E-005-06 (Type 29, middle trace) and ketoglutaric acid (bottom trace).

Type 29 material was isolated from a sonication experiment using ketoglutaric acid and Q203 free base (1:1 acid/API) in THF. XRPD analysis of Type 29 solid (ND-0006E-005-06, FIG. 52) showed the material was disordered crystalline and similar to Type 25 with additional peaks observed. Proton NMR analysis showed no peak shifting, ~0.16 molar eq. of THF and ~0.9 molar eq. of ketoglutaric acid which may suggest a possible co-crystal or polymorph of Q203 free base (data not shown).

5.30 Type 30 (Fumaric)

Figure 53:
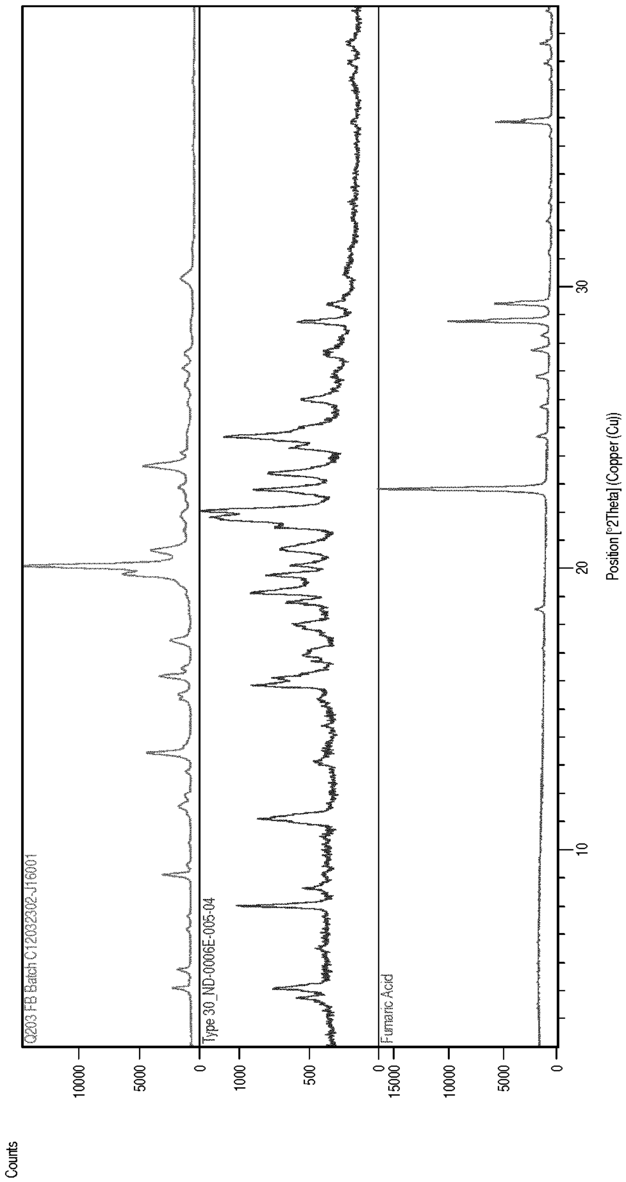
FIG. 53 shows XRPD patterns of Q203 free base (top trace), ND-0006E-005-04 (Type 30, middle trace) and fumaric acid (bottom trace).

Type 30 material was isolated from a sonication experiment using ketoglutaric acid and Q203 free base (1:1 acid/API) in THF. XRPD analysis of Type 30 solid (ND-0006E-005-04, FIG. 53) showed the material was crystalline and $^1$H NMR analysis (data not shown) showed no peak shifting or residual solvent, with ~0.85 molar eq. of fumaric acid which may suggest a possible polymorph or fumaric acid co-crystal of Q203 free base.

5.31 Type 31 (Sulphuric)

Figure 54:
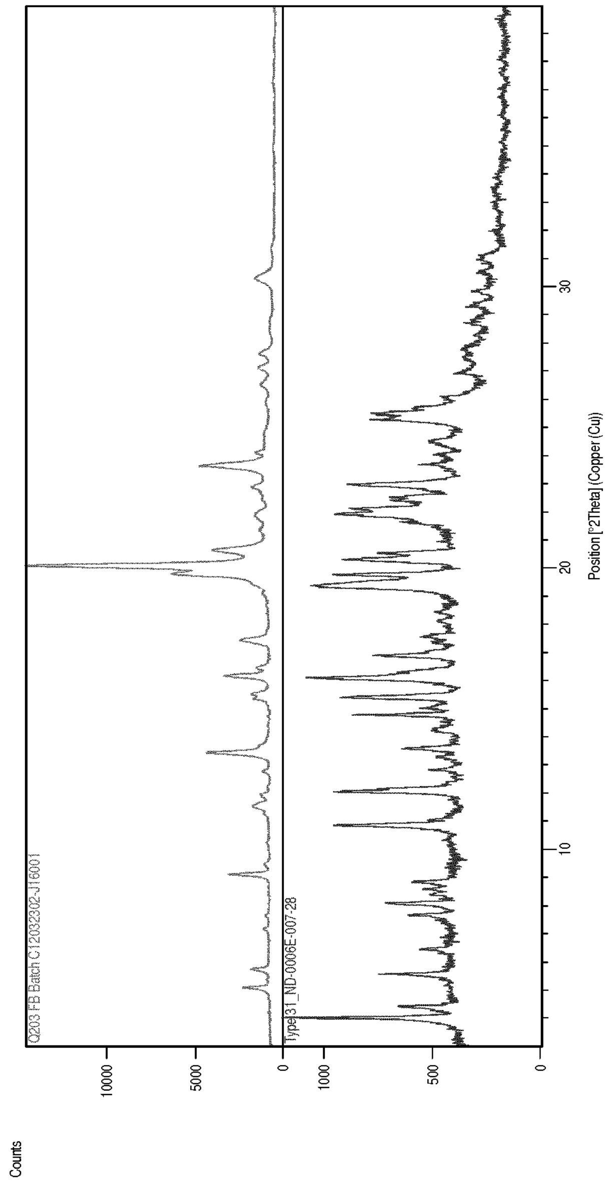
FIG. 54 shows XRPD patterns of Q203 free base (top trace) and ND-0006E-007-28 (Type 31, bottom trace).

Type 31 material was generated from a slow evaporation followed by high temperature slurrying experiment (40° C.) using sulphuric acid and Q203 free base (2:1 acid/API) in IPA for 7 days. XRPD analysis of Type 31 solid (ND-0006E-007-28, FIG. 54) showed the material was crystalline and proton NMR spectroscopy showed significant peak shifting with no residual solvent suggesting salt formation (data not shown). It should be noted the presence of additional peaks which may be explained by degradation. The stoichiometry was not determined.

5.32 Type 32

Figure 55:
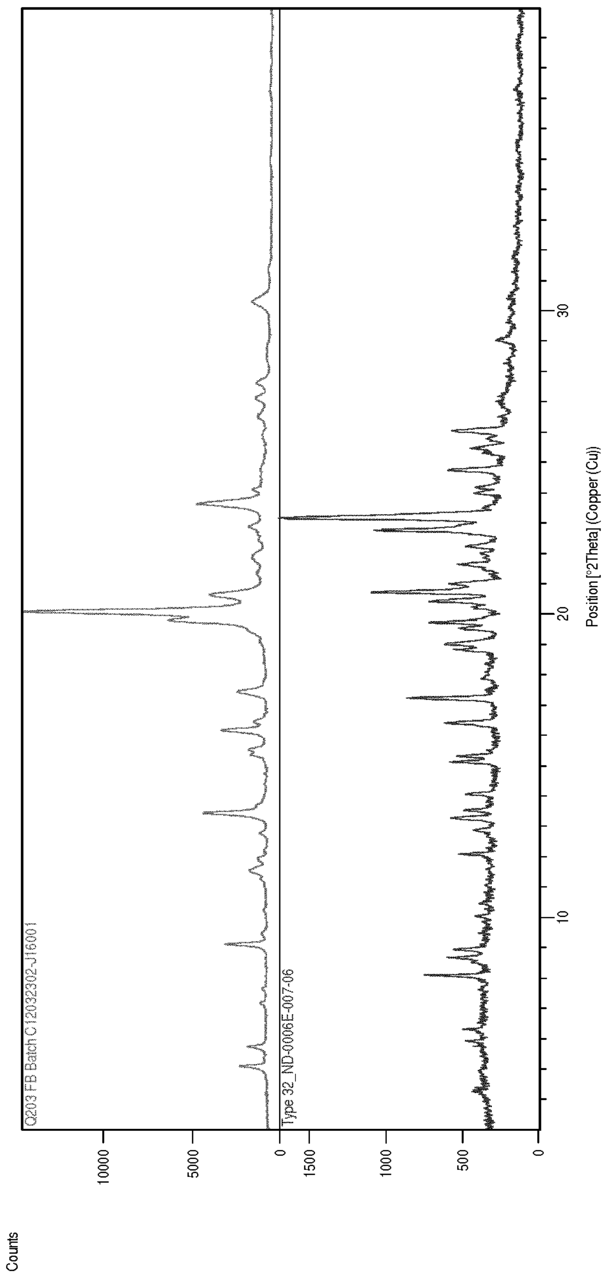
FIG. 55 shows XRPD patterns of Q203 free base (top trace) and ND-0006E-007-06 (Type 32, bottom trace).

Type 32 material was generated from high temperature slurrying experiments (40° C.) involving various acids and Q203 free base (2:1 acid/API) in IPA. Experimental conditions leading to pure Type 32 and Type 32 mixtures (with co-acid) are highlighted in Table 18. XRPD analysis of Type 32 solid (ND-0006E-007-06) showed the material was crystalline present (FIG. 55). $^1$H NMR analysis of Type 32 material showed no peak shifting (data not shown) and residual solvent and ~0.2 molar equivalent of co-former. As this Type was obtained from different co-formers, it is likely to be a polymorph of Q203 free base.

TABLE 18

Experimental conditions leading to Type 32 solid (pure and mixtures)

| Salt former | Sample No. (ND-0006E-) | Solvent | Result | XRPD |
|---|---|---|---|---|
| gentisic | 007-17 | IPA | solid | Type 32 |
| gluconic (D) | 007-25 | IPA | solid | Type 32 |
| glycolic (hydroxyacetic) | 007-05 | IPA | solid | Type 32 |
| ketoglutaric (oxoglutaric) | 007-06 | IPA | solid | Type 32 |
| maleic | 007-20 | IPA | solid | Type 32 |
| malic (L) | 007-07 | IPA | solid | Type 32 |

TABLE 18-continued

| Experimental conditions leading to Type 32 solid (pure and mixtures) | | | | |
|---|---|---|---|---|
| Salt former | Sample No. (ND-0006E-) | Solvent | Result | XRPD |
| malonic | 007-08 | IPA | solid | Type 32 |
| phosphoric | 007-26 | IPA | solid | Type 32 |
| pyroglutamic (L) | 007-11 | IPA | solid | Type 32 |
| pyruvic (2-oxopropanoic) | 007-21 | IPA | solid | Type 32 |
| succinic | 007-12 | IPA | solid | Type 32 |
| galactaric (mucic) | 007-29 | IPA | solid | Type 32 + co-acid |
| lactobionic | 007-19 | IPA | solid | Type 32 + additional peaks |

5.33 Type 33 (Benzenesulfonic)

Figure 56:
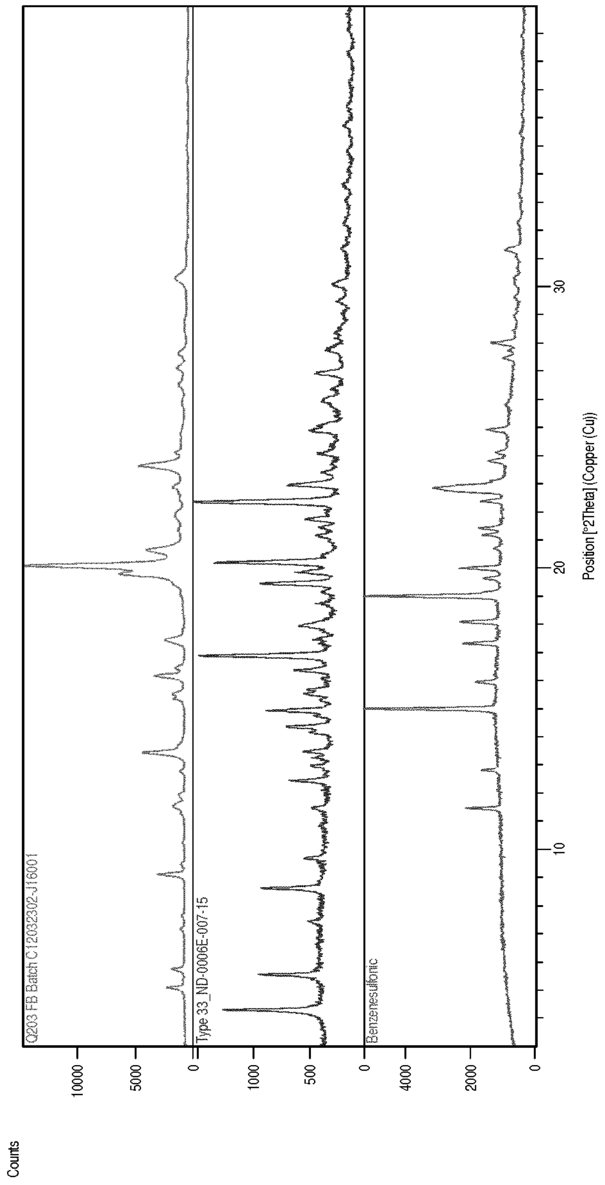
FIG. 56 shows XRPD patterns of Q203 free base (top trace), ND-0006E-007-15 (Type 33, middle trace) and benzenesulfonic acid (BSA) (bottom trace).

Type 33 material was generated from a high temperature slurrying experiment (40° C.) using BSA and Q203 free base (2:1 acid/API) in IPA for 7 days. XRPD analysis of Type 33 solid (ND-0006E-007-15, FIG. 56) showed the material was crystalline and proton NMR spectroscopy (data not shown) suggested possible salt formation with no residual solvent and likely a 2:1 acid/API stoichiometry. It should be noted similarities with Type 6 observed.

5.34 Type 34 (Ethane-1,2-Disulfonic Acid)

Figure 57:
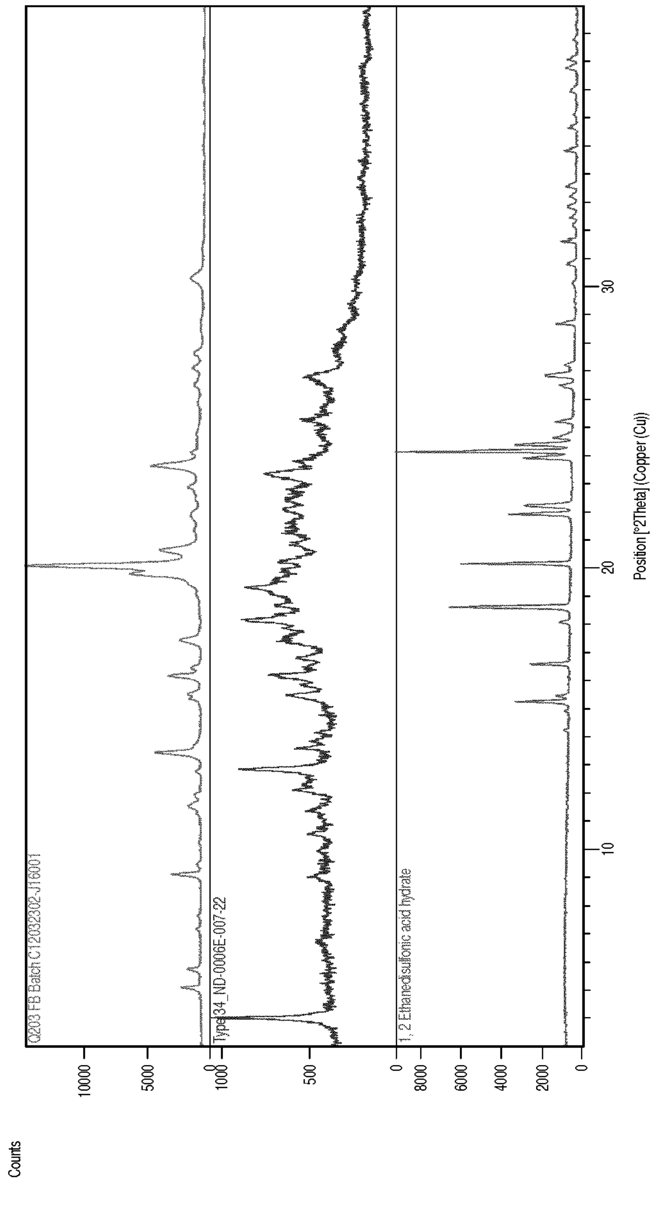
FIG. 57 shows XRPD patterns of Q203 free base (top trace), ND-0006E-007-22 (Type 34, middle trace) and ethanedisulfonic acid (EDSA) (bottom trace).

Type 34 material was generated from a high temperature slurrying experiment (40° C.) using EDSA and Q203 free base (2:1 acid/API) in IPA for 7 days. XRPD analysis of Type 34 solid (ND-0006E-007-22, FIG. 57) showed the material was disordered crystalline and proton NMR spectroscopy (data not shown) showed peak shifting and no residual solvent, suggesting salt formation with likely a 2:1 acid/API stoichiometry.

5.35 Type 35 (HC)

Figure 58:
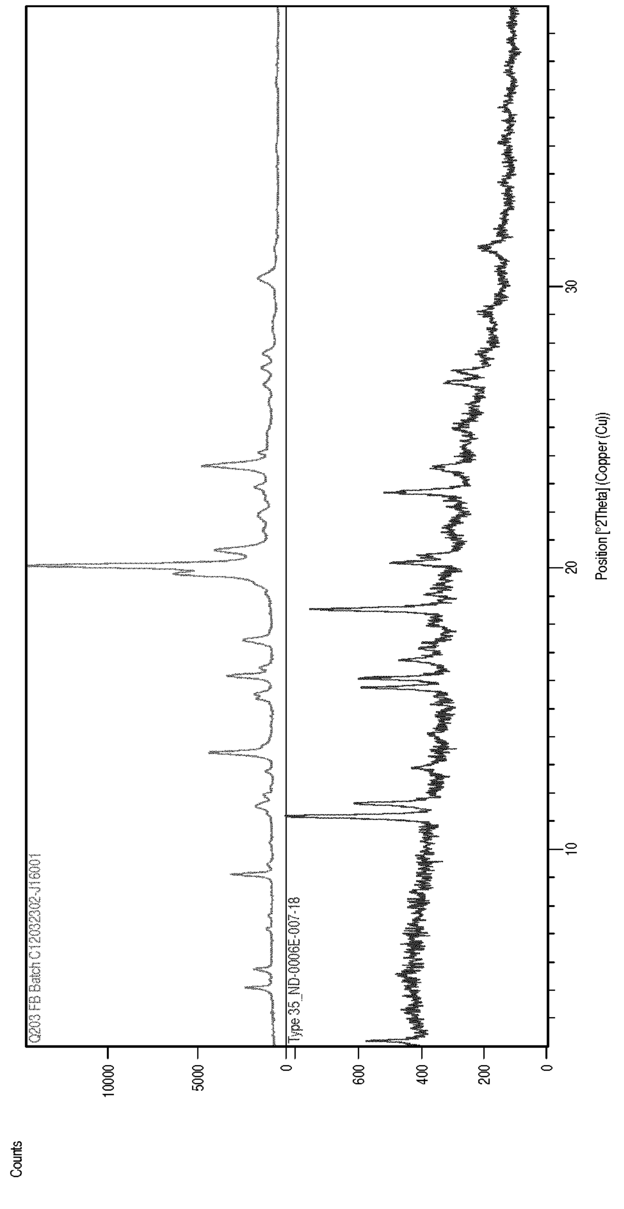
FIG. 58 shows XRPD patterns of Q203 free base (top trace) and ND-0006E-007-18 (Type 35, bottom trace).

Type 35 material was generated from a slow evaporation followed by high temperature slurrying experiment (40° C.) using HCl and Q203 free base (2:1 acid/API) in IPA for 7 days. XRPD analysis of Type 35 solid (ND-0006E-007-18, FIG. 58) showed the material was disordered crystalline and proton NMR spectroscopy (data not shown) showed peak shifting suggesting salt formation. No residual solvent or degradation was observed from the NMR spectrum. The stoichiometry has not been determined.

5.36 Type 36 (HCl)

Figure 59:
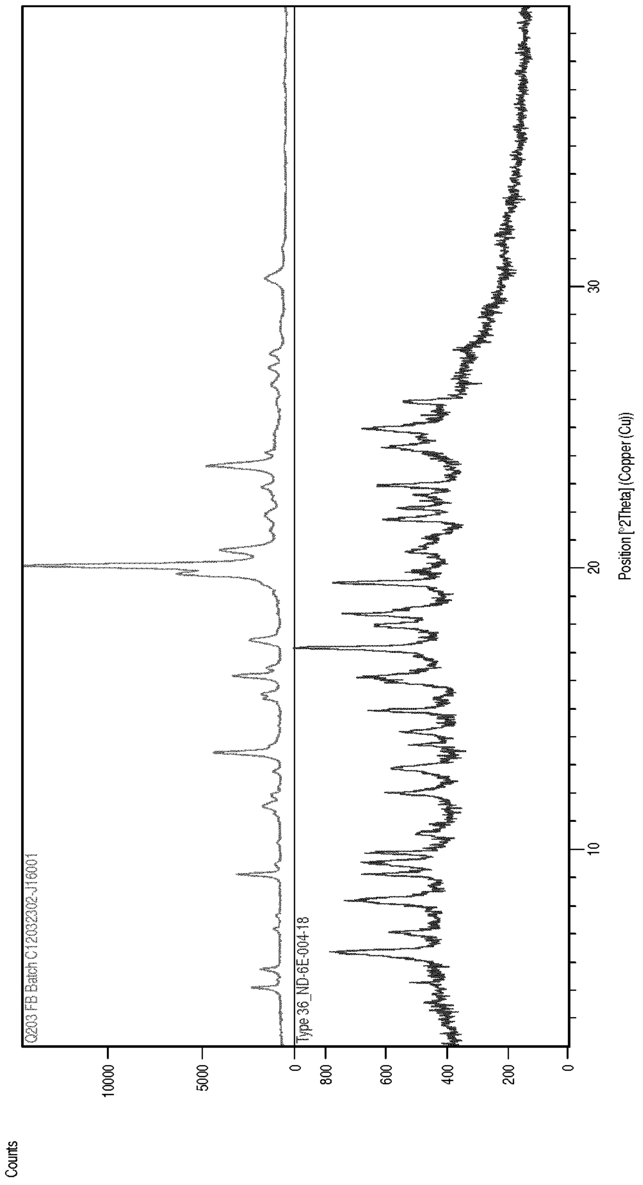
FIG. 59 shows XRPD patterns of Q203 free base (top trace) and ND-0006E-004-18 (Type 36, bottom trace).

Type 36 material was isolated from an ambient temperature slurrying experiment using HCl and Q203 free base (1:1 acid/API) in MTBE for 7 days. XRPD analysis of Type 36 solid (ND-0006E-004-18, FIG. 59) showed the material was crystalline, with similarities to the diffraction pattern of Type 3+additional peaks. Proton NMR analysis (data not shown) showed peak shifting with trace amounts of residual MTBE (0.007 molar eq.) and suggesting HCl salt of Q203. The stoichiometry has not been determined.

5.37 Type 37 (Phosphoric)

Figure 60:
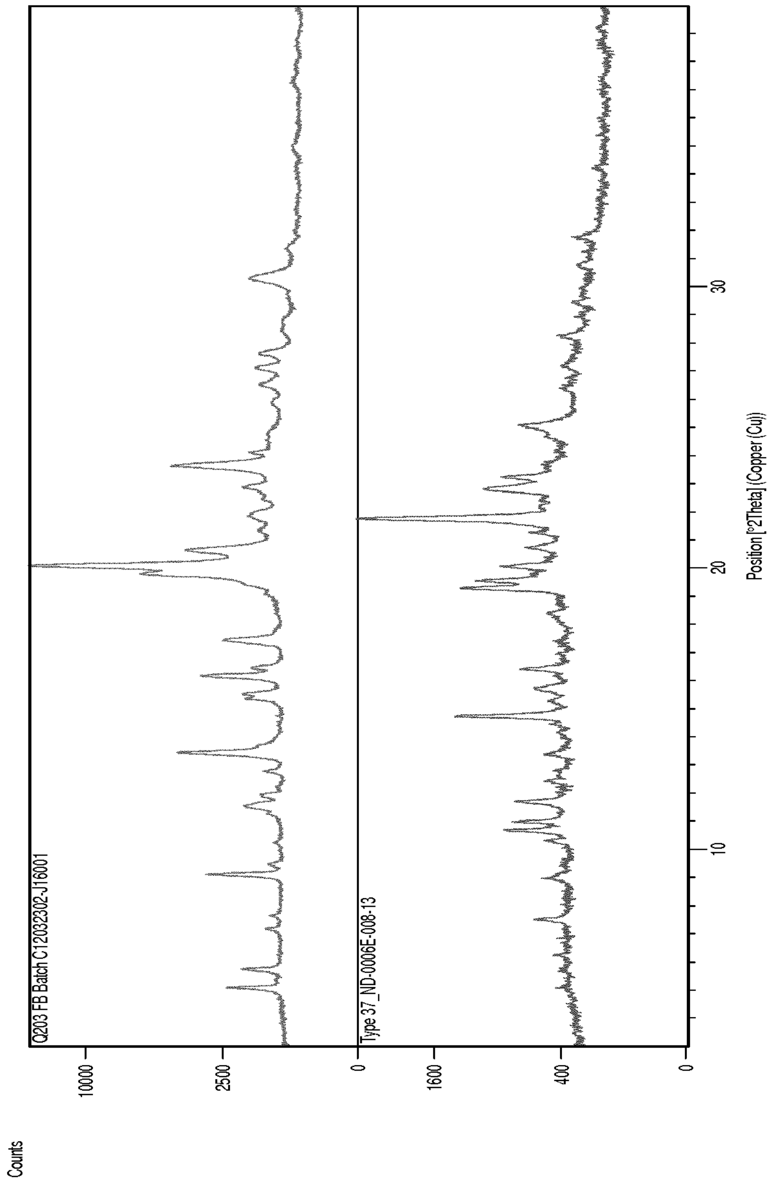
FIG. 60 shows XRPD patterns of Q203 free base (top trace) and ND-0006E-008-13 (Type 37, bottom trace).

Type 37 material was generated from high temperature slurrying experiment (40° C.) and LAG technique using acetone and Q203 free base (1:1 acid/API). XRPD analysis of Type 37 solid (ND-0006E-008-13, FIG. 60) showed the material was crystalline. The slight baseline drift suggests the presence of amorphous content.

Proton NMR analysis suggests peak shifting with around ~0.09 molar eq. of residual acetone Q203 phosphate salt (data not shown). The stoichiometry has not been determined.

5.38 Type 38 (Gluconic)

Figure 61:
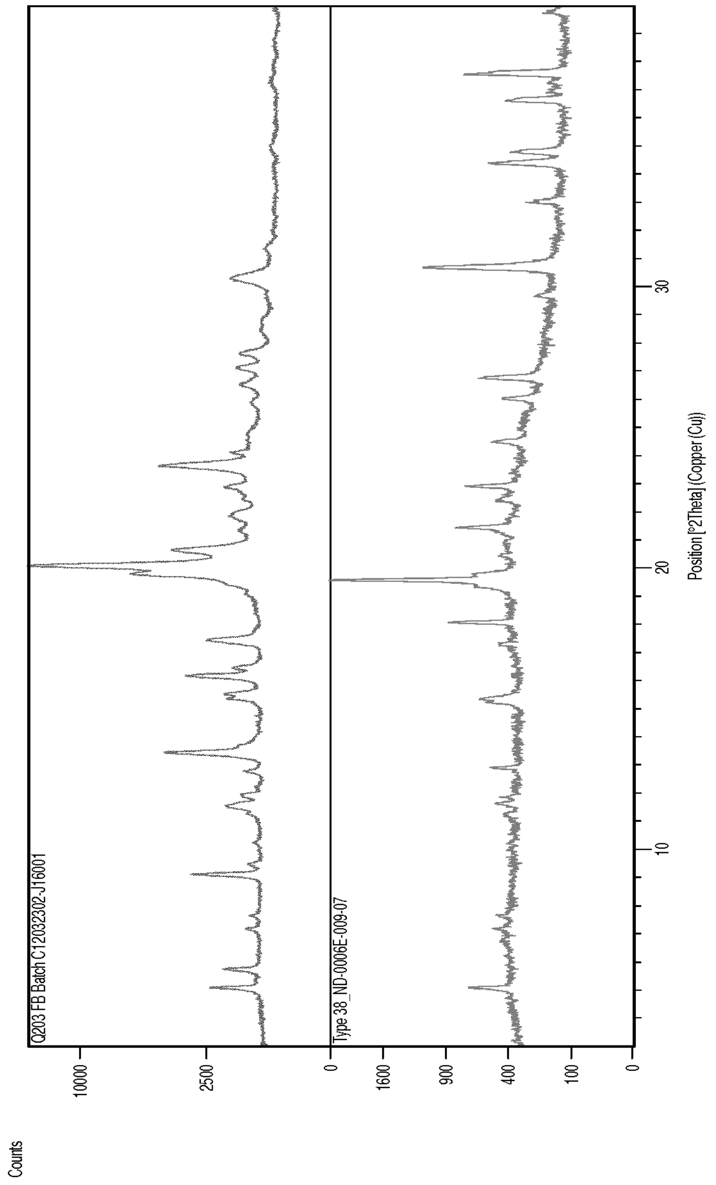
FIG. 61 shows XRPD patterns of Q203 free base (top trace) and ND-0006E-009-07 (Type 38, bottom trace).

Type 38 material was isolated from a co-melt experiment using gluconic and Q203 free base (1:1 acid/API). XRPD analysis of Type 38 solid (ND-0006E-009-07, FIG. 61) showed the material was crystalline. The baseline drift suggests the presence of amorphous content. Proton NMR analysis (data not shown) showed no peak shifting as expected, no trace of residual solvent and no presence of co-former. TG/DTA results (data not shown) showed a melt at onset temperature of 164° C. and another endotherm at onset 218° C. associated with weight loss. These results suggest Type 38 to be likely a polymorph of the free base.

5.39 Type 39 (Multiple Co-Formers)

Figure 62:
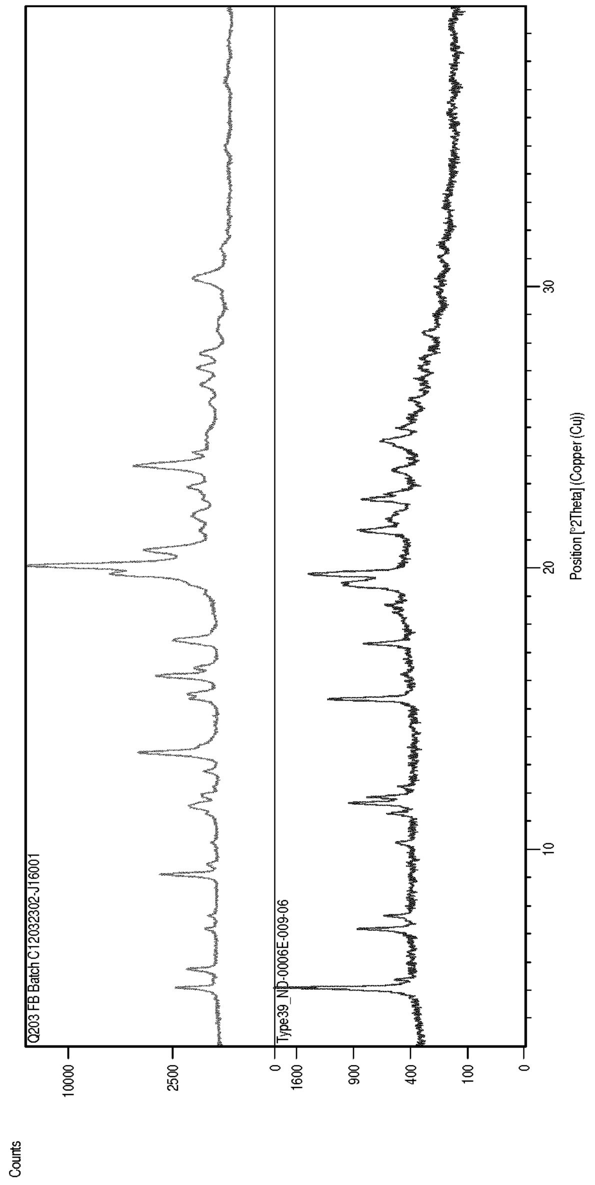
FIG. 62 shows XRPD patterns of Q203 free base (top trace) and ND-0006E-009-06 (Type 39, bottom trace).

Type 39 material was isolated from co-melt experiments using multiple co-formers (malonic, pyruvic, saccharin) and Q203 free base (1:1 acid/API). XRPD analysis of Type 39 solid (ND-0006E-009-06, FIG. 62) showed the material was crystalline. A baseline drift suggests the presence of amorphous content. Proton NMR analysis (data not shown) showed no peak shifting with around 0.9 molar eq. of co-formers and suggesting potential co-crystal or polymorph of the free base.

TABLE 19

| Experimental conditions leading to Type 39 solid (pure and mixtures) | | | | |
|---|---|---|---|---|
| Salt former | Sample No. (ND-0006E-) | Acid:API (molar ratio) | Result | XRPD |
| malonic | 009-03 | 1:1 molar eq. | solid | Type 39 |
| pyruvic (2-oxopropanoic) | 009-06 | 1:1 molar eq. | solid | Type 39 |
| saccharin | 009-09 | 1:1 molar eq. | solid | Type 39 + saccharin |

5.40 Type 40 (Multiple Co-Formers)

Figure 63:
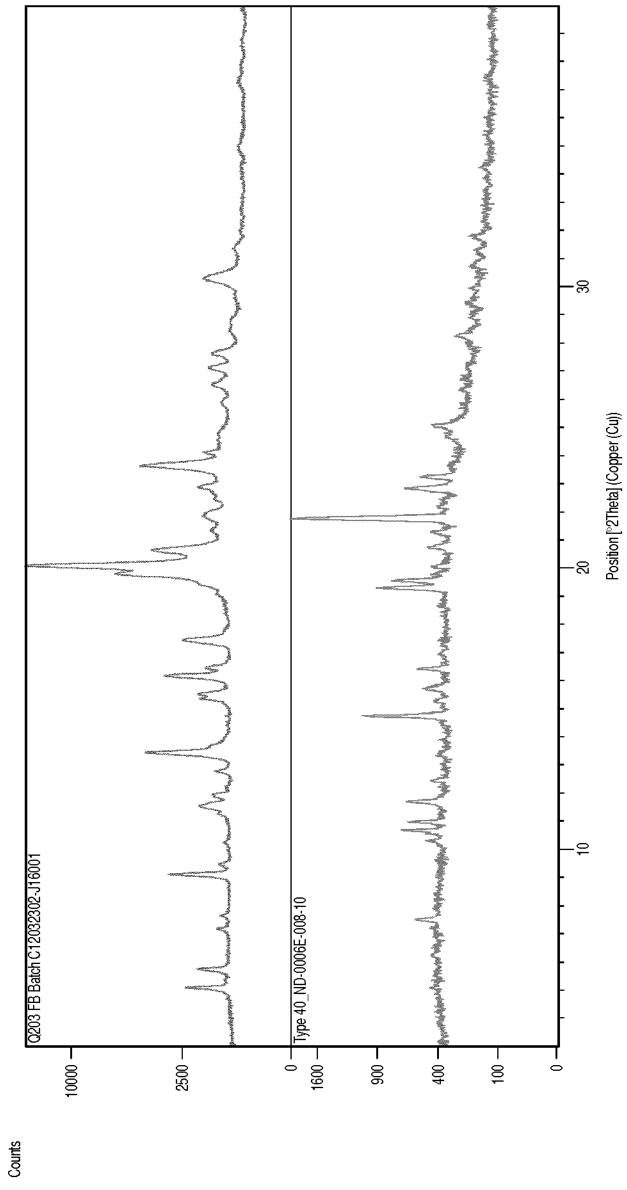
FIG. 63 shows XRPD patterns of Q203 free base (top trace) and ND-0006E-008-10 (Type 40, bottom trace).

Type 40 material was isolated from HT slurry and LAG experiments using multiple co-formers (malonic, pyruvic, pyroglutamic, etc. . . . ) and Q203 free base (1:1 acid/API). XRPD analysis of one of the Type 40 solid (ND-0006E-008-10, FIG. 63) showed the material was crystalline. A slight baseline drift suggests the presence of amorphous content. Proton NMR analysis showed no peak shifting with around 0.3 molar eq. of residual acetone and no trace of co-former suggesting likely polymorph of the free base (data not shown).

TABLE 20

| Experimental conditions leading to Type 40 solid (pure and mixtures) | | | | |
|---|---|---|---|---|
| Salt former | Sample No. (ND-0006E-) | Acid:API (molar ratio) | Result | XRPD |
| malonic | 008-05 | 1:1 molar eq. | solid | Type 40 |
| pyruvic (2-oxopropanoic) | 008-10 | 1:1 molar eq. | solid | Type 40 |
| glycolic (hydroxyacetic) | 010-02 | 1:1 molar eq. | solid | Type 40 |
| malonic | 010-03 | 1:1 molar eq. | solid | Type 40 |
| pyroglutamic (L) | 010-06 | 1:1 molar eq. | solid | Type 40 |
| pyruvic (2-oxopropanoic) | 010-08 | 1:1 molar eq. | solid | Type 40 |
| gluconic (D) | 010-11 | 1:1 molar eq. | solid | Type 40 |
| citric | 008-03 | 1:1 molar eq. | solid | Type 40 + additional peaks |
| glycolic (hydroxyacetic) | 008-04 | 1:1 molar eq. | solid | Type 40 + additional peaks |
| pyroglutamic (L) | 008-07 | 1:1 molar eq. | solid | Type 40 + Form A + free acid |

5.41 Type 41 (Multiple Co-Formers)

Type 41 material was isolated from HT slurry and LAG experiments using multiple co-formers (lactobionic, ascorbic, 2-furoic, galactaric) and Q203 free base (1:1 acid/API).

Figure 64:
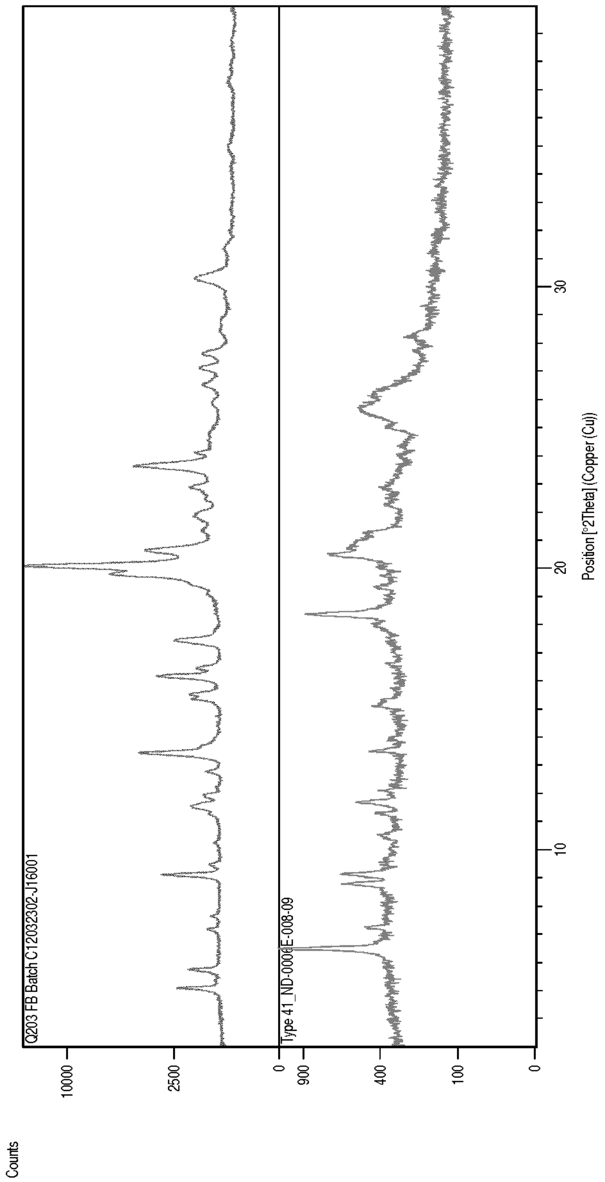
FIG. 64 shows XRPD patterns of Q203 free base (top trace) and ND-0006E-008-09 (Type 41, bottom trace).

XRPD analysis of one of the Type 41 solid (ND-0006E-008-09, FIG. 64) showed the material was crystalline. A slight baseline drift suggests the presence of amorphous content. Proton NMR analysis showed no peak shifting with around 0.3 molar eq. of residual acetone and no trace of co-former suggesting likely Type 41 as a polymorph of the free base (data not shown).

TABLE 21

Experimental conditions leading to Type 41 solid (pure and mixtures)

| Salt former | Sample No. (ND-0006E-) | Acid:API (molar ratio) | Result | XRPD |
|---|---|---|---|---|
| lactobionic | 010-01 | 1:1 molar eq. | solid | Type 41 |
| ascorbic | 010-07 | 1:1 molar eq. | solid | Type 41 |
| lactobionic | 008-01 | 1:1 molar eq. | solid | Type 41 |
| 2-furoic | 010-14 | 1:1 molar eq. | solid | Type 41 + T28 |
| galactaric (mucic) | 010-01 | 1:1 molar eq. | solid | Type 41 + T28 |

5.42 Type 42 (Gentisic)

Figure 65:
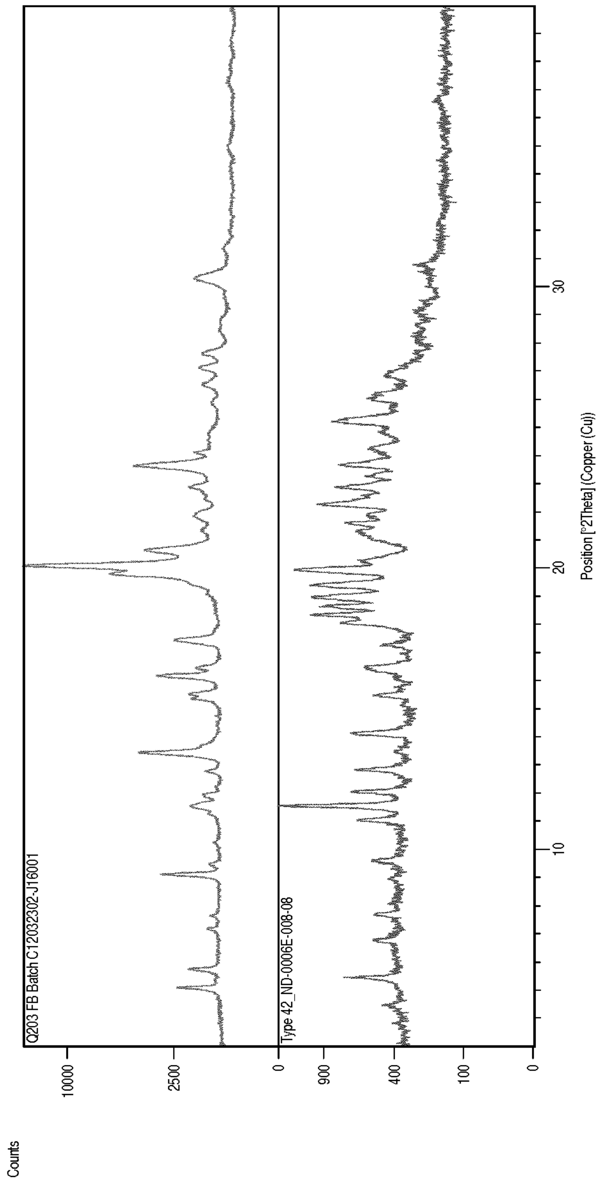
FIG. 65 shows XRPD patterns of Q203 free base (top trace) and ND-0006E-008-08 (Type 42, bottom trace).

Type 42 material was isolated from a LAG experiment using gentisic and Q203 free base (1:1 acid/API) in acetone. XRPD analysis of Type 42 solid (ND-0006E-008-08, FIG. 65) showed the material was crystalline. A slight baseline drift suggests the presence of amorphous content. Proton NMR analysis showed no peak shifting, ~0.14 molar eq. of acetone (~1.12% w/w) and ~0.67 molar eq. of co-former (data not shown). TG/DTA showed a weight loss from 25 to 113° C. (likely moisture) and an endotherm was observed at onset around 121° C. These results suggest either a polymorph or a potential co-crystal of Q203 free base. Further analysis would be needed to confirm one of these assumptions.

5.43 Type 43 (Ascorbic)

Figure 66:
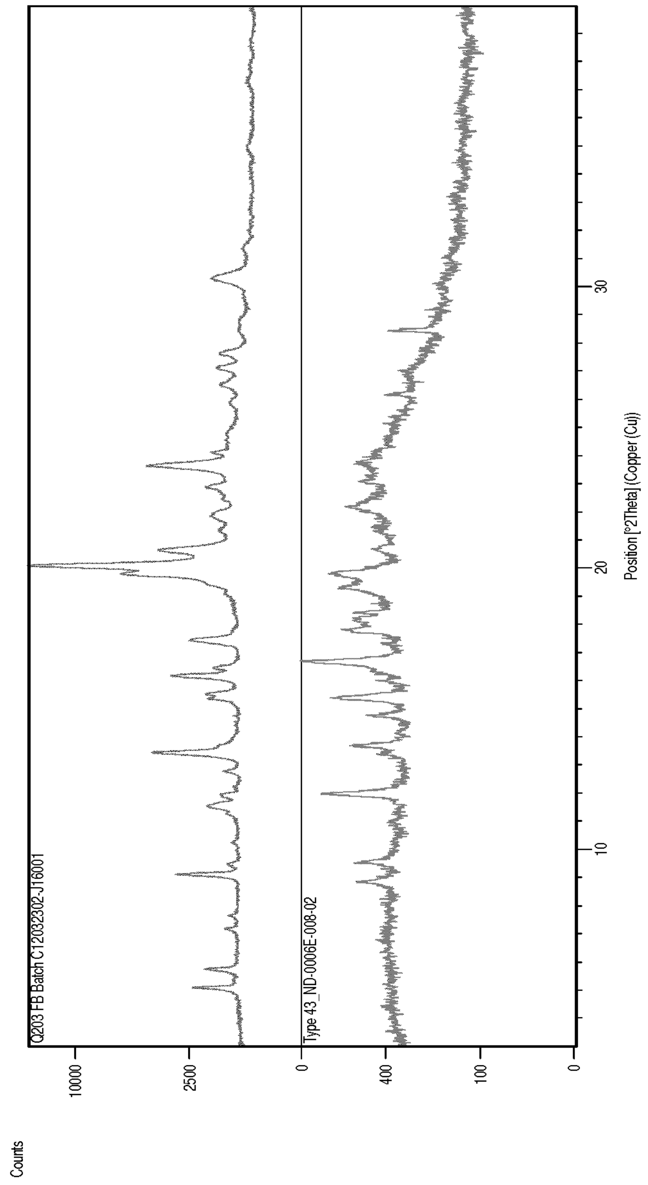
FIG. 66 shows XRPD patterns of Q203 free base (top trace) and ND-0006E-008-02 (Type 43, bottom trace).

Type 43 material was isolated from a LAG experiment using ascorbic and Q203 free base (1:1 acid/API) in a mixture of IPA/water. XRPD analysis of Type 43 solid (ND-0006E-008-02, FIG. 66) showed the material was crystalline. A slight baseline drift suggests the presence of amorphous content. Proton NMR analysis (data not shown) showed no peak shifting as expected, no residual IPA and ~0.8 molar eq. of co-former. TG/DTA showed a weight loss from 25 to ~131° C. of ~0.9% likely attributable to water moisture. Two endotherm events were observed at onset of 136 and 158° C. associated with a constant weight loss of ~11% from 130 to 300° C. These results suggest that Type 43 may be a mixture of polymorphs (free base and co-former) or a potential co-crystal of Q203. Further analysis would be required to better understand the nature of this Type.

5.44 Type 44 (Saccharin)

Figure 67:
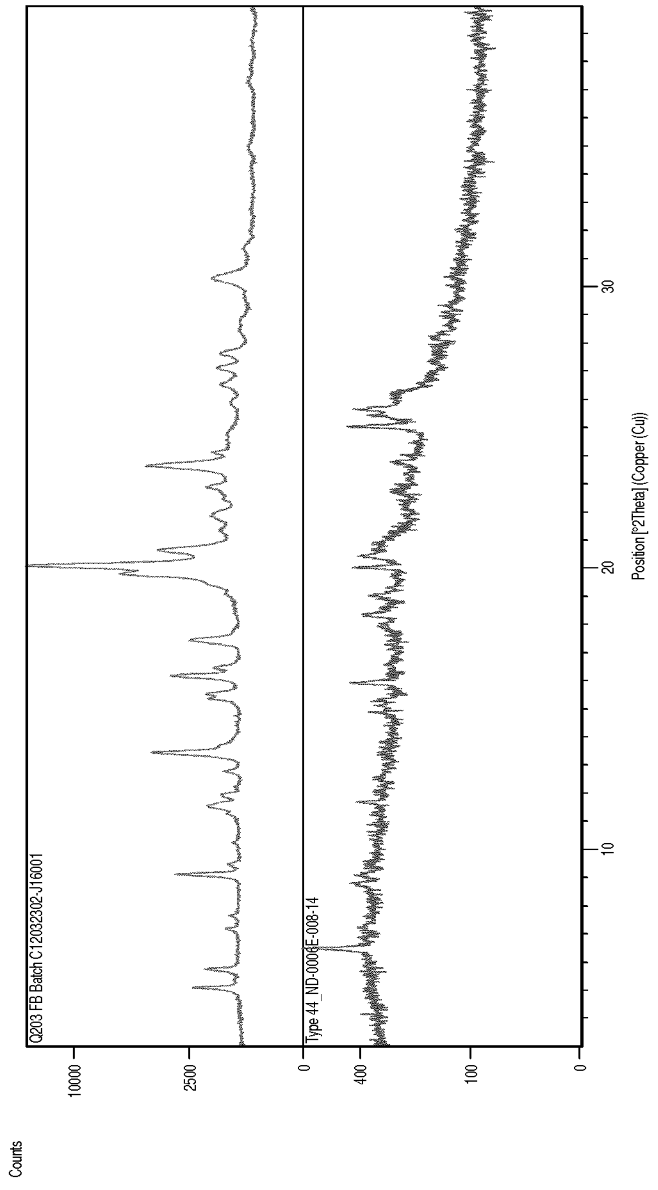
FIG. 67 shows XRPD patterns of Q203 free base (top trace) and ND-0006E-008-01 (Type 44, bottom trace).

Type 44 material was isolated from a LAG experiment using saccharin and Q203 free base (1:1 acid/API) in a mixture of IPA/water. XRPD analysis of Type 44 solid (ND-0006E-008-14, FIG. 67) showed the material was disordered crystalline. A slight baseline drift suggests the presence of amorphous content. Proton NMR analysis (data not shown) showed peak shifting with ~0.5 molar eq. of IPA suggesting IPA hemisolvate of Q203 saccharin salt. Further experiments may lead to unsolvated saccharin salt of Q203

5.45 Type 45 (Oxalic)

Figure 68:
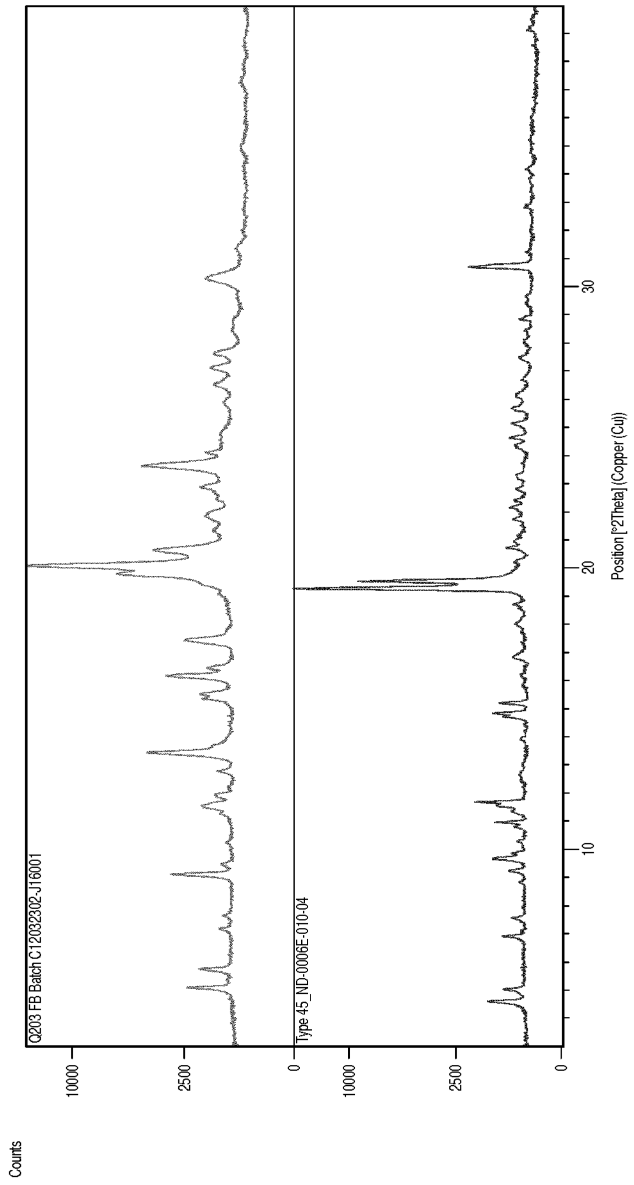
FIG. 68 shows XRPD patterns of Q203 free base (top trace) and ND-0006E-010-04 (Type 45, bottom trace).

Type 45 material was isolated from a HT slurry experiment (40 C) using oxalic and Q203 free base (1:1 acid/API) in acetone for 5 days. XRPD analysis of Type 45 solid (ND-0006E-010-04, FIG. 68) showed the material was crystalline. A slight baseline drift suggests the presence of amorphous content. Proton NMR analysis showed peak shifting with ~0.06 molar eq. of acetone suggesting salt formation of Q203 oxalate salt (data not shown).

5.46 Type 46 (Oxalic)

Figure 69:
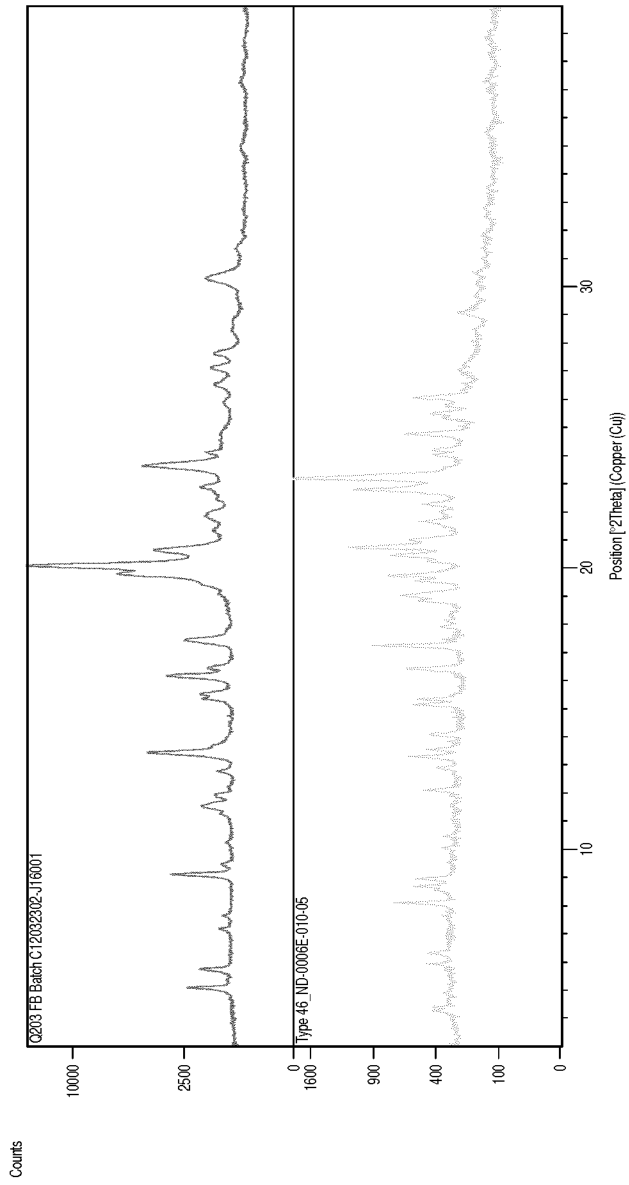
FIG. 69 shows XRPD patterns of Q203 free base (top trace) and ND-0006E-010-05 (Type 46, bottom trace).

Type 46 material was isolated from a HT slurry experiment (40 C) using oxalic and Q203 free base (1:1 acid/API) in methanol for 5 days. XRPD analysis of Type 46 solid (ND-0006E-010-05, FIG. 69) showed the material was crystalline. A slight baseline drift suggests the presence of amorphous content. Proton NMR analysis (data not shown) showed no peak shifting suggesting polymorph of the free base.

5.47 Type 47 (Saccharin)

Figure 70:
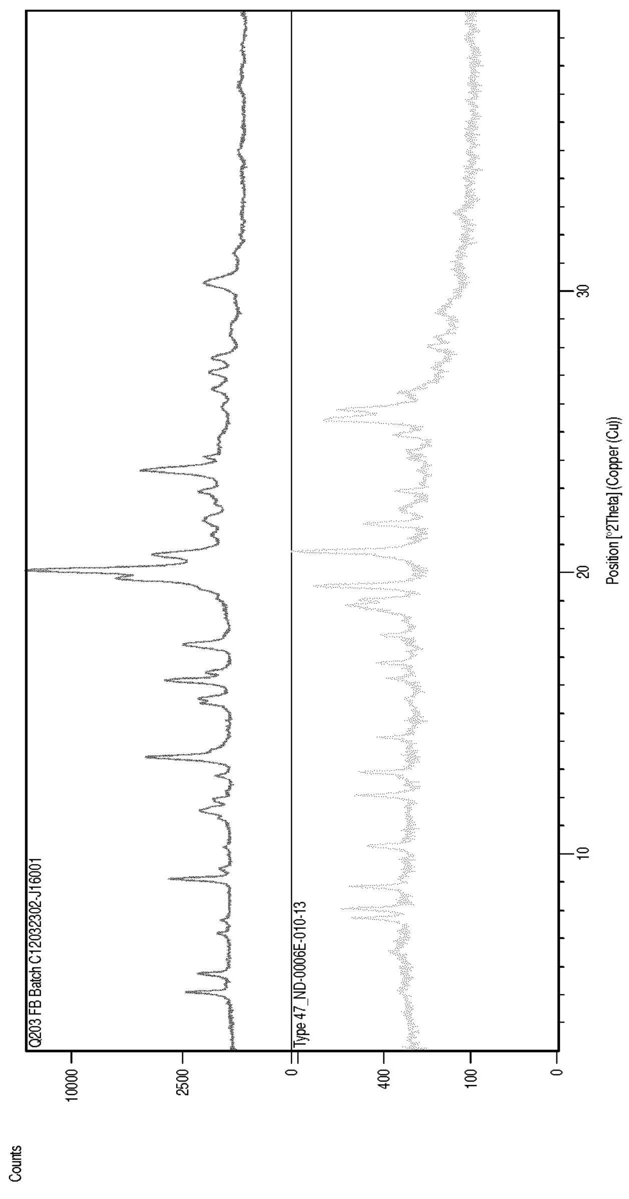
FIG. 70 shows XRPD patterns of Q203 free base (top trace) and ND-0006E-010-13 (Type 47, bottom trace).

Type 47 material was isolated from a HT slurry experiment (40° C.) using saccharin and Q203 free base (1:1 acid/API) in a mixture of IPA/water for 5 days. XRPD analysis of Type 47 solid (ND-0006E-00-13, FIG. 70) showed the material was crystalline. A slight baseline drift suggests the presence of amorphous content. Proton NMR analysis (data not shown) showed peak shifting with trace of IPA, ~0.7 mol. eq. of co-former, suggesting salt formation of Q203 saccharin salt.

5.48 Type 48 (Salicylic)

Figure 71:
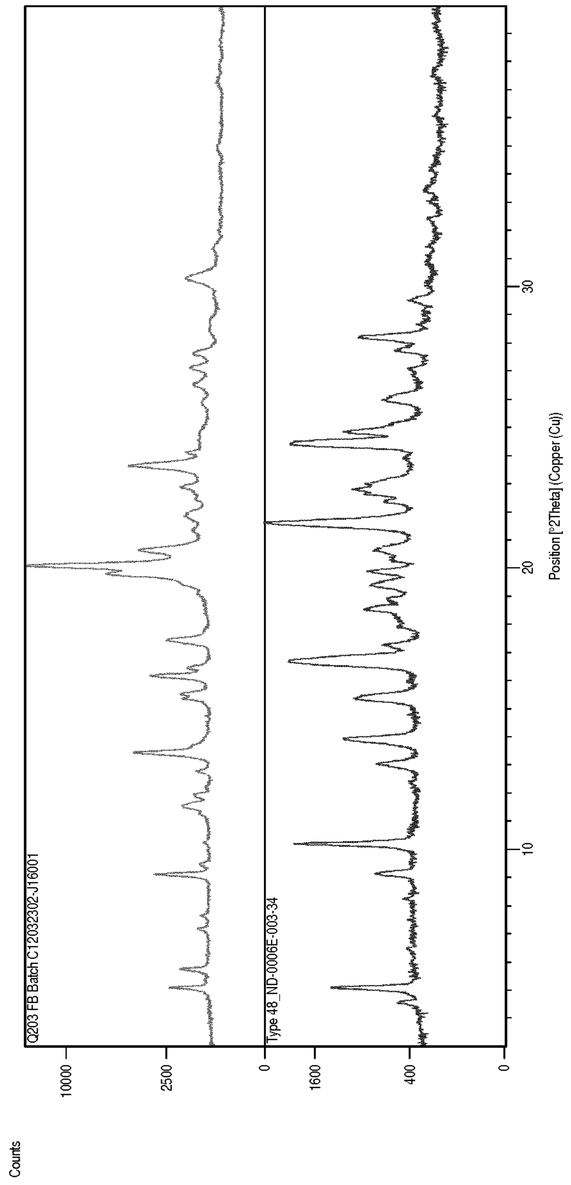
FIG. 71 shows XRPD patterns of Q203 free base (top trace) and ND-0006E-003-34 (Type 48, bottom trace).

Type 48 material was isolated from a slow evaporation experiment using salicylic and Q203 free base (1:1 acid/API) in a mixture of THF/acetone. XRPD analysis of Type 47 solid (ND-0006E-003-34, FIG. 71) showed the material was crystalline. Proton NMR analysis showed no peak shifting, ~0.9 molar eq. co-former, ~0.1 molar eq. of THF and no residual acetone suggesting potential co-crystal or polymorph of the free base (data not shown).

5.49 Type 49 (nitric)

Figure 72:
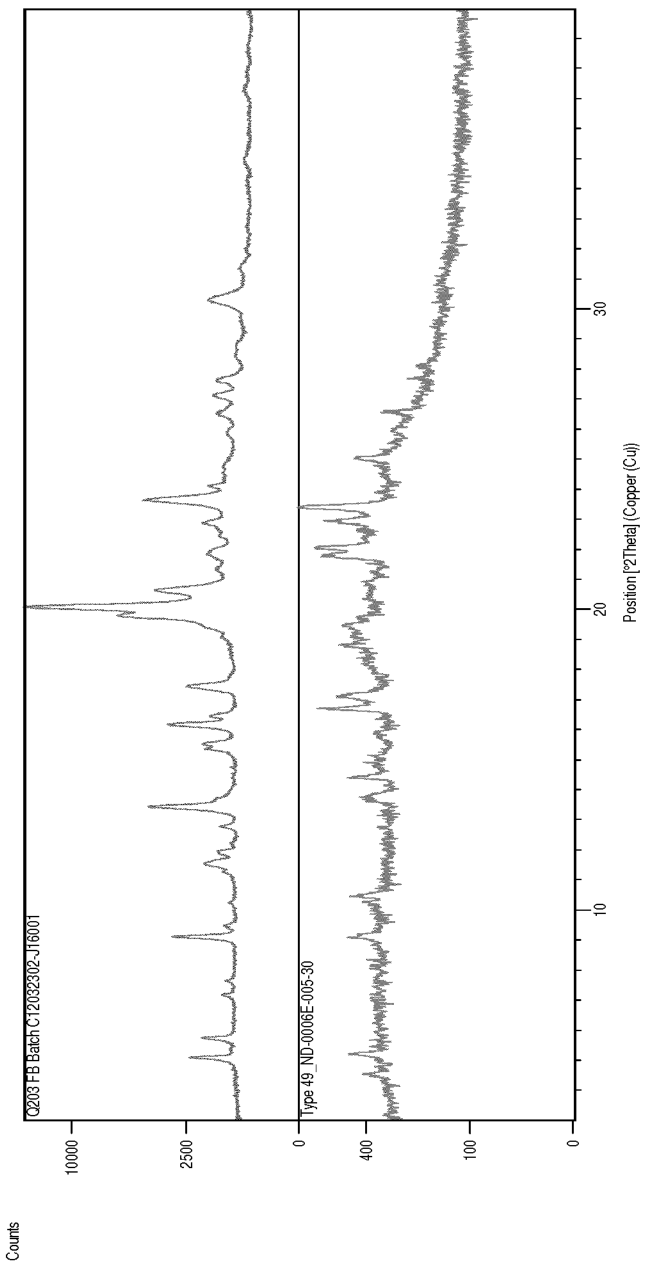
FIG. 72 shows XRPD patterns of Q203 free base (top trace) and ND-0006E-005-30 (Type 49, bottom trace).

Type 49 material was isolated from a sonication experiment using nitric and Q203 free base (1:1 acid/API) in THF. XRPD analysis of Type 49 solid (ND-0006E-005-30, FIG. 72) showed the material was crystalline, very similar to Type 3 with additional peaks. Proton NMR analysis (data not shown) showed peak shifting with ~0.25 molar eq. of THF suggesting likely Type 49 to be a nitrate salt of Q203.

5.50 Type 50 (Pamoic)

Figure 73:
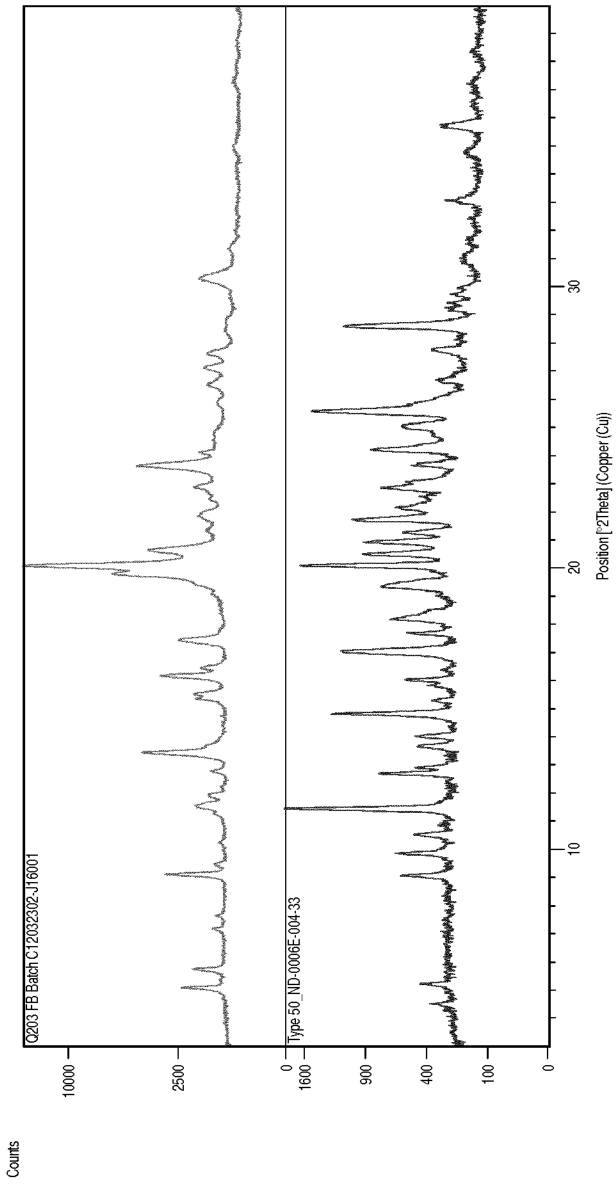
FIG. 73 shows XRPD patterns of Q203 free base (top trace) and ND-0006E-004-33 (Type 50, bottom trace).

Type 50 material was isolated from a RT slurry experiment using pamoic and Q203 free base (1:1 acid/API) in MTBE for 5 days. XRPD analysis of Type 50 solid (ND-0006E-004-33, FIG. 73) showed the material was crystalline, very similar to Type 3 with additional peaks. Proton NMR analysis (data not shown) showed no peak shifting with ~0.07 molar eq. of MTBE and ~0.65 molar eq. of co-former suggesting possibly polymorph of Q203 free base or co-crystal.

5.51 Type 51 (Pamoic)

Figure 74:
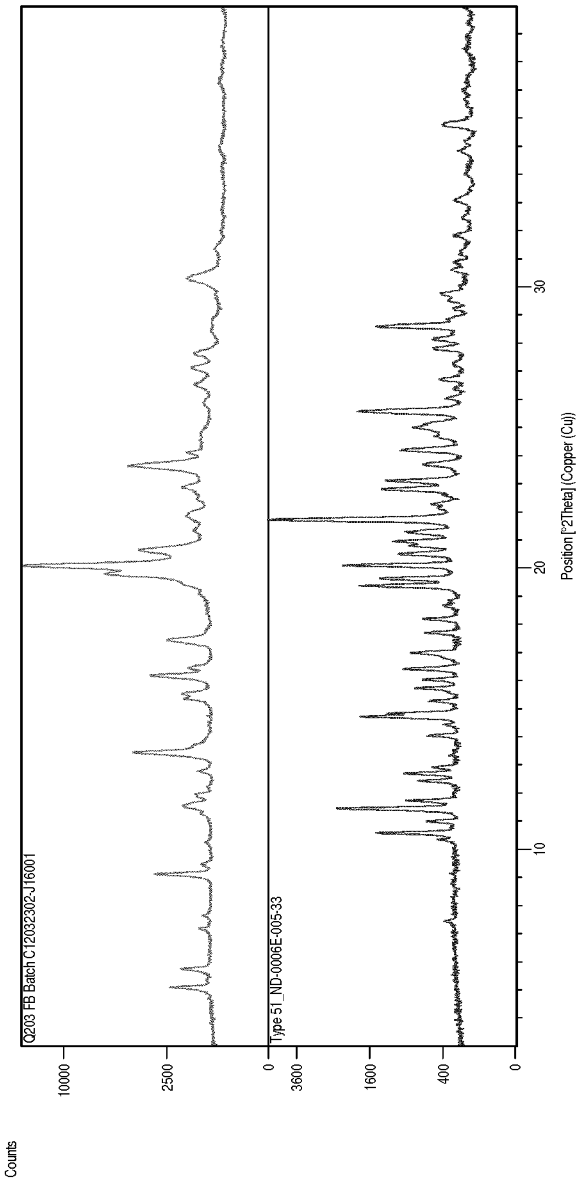
FIG. 74 shows XRPD patterns of Q203 free base (top trace) and ND-0006E-005-33 (Type 51, bottom trace).

Type 51 material was isolated from a sonication experiment using pamoic and Q203 free base (1:1 acid/API) in THF. XRPD analysis of Type 51 solid (ND-0006E-005-33, FIG. 74) showed the material was crystalline. Proton NMR analysis (data not shown) showed no peak shifting with ~0.02 molar eq. of THF and ~0.9 molar eq. of co-former suggesting possibly polymorph of Q203 free base or co-crystal.

5.52 Type 52 (Salicylic)

Figure 75:
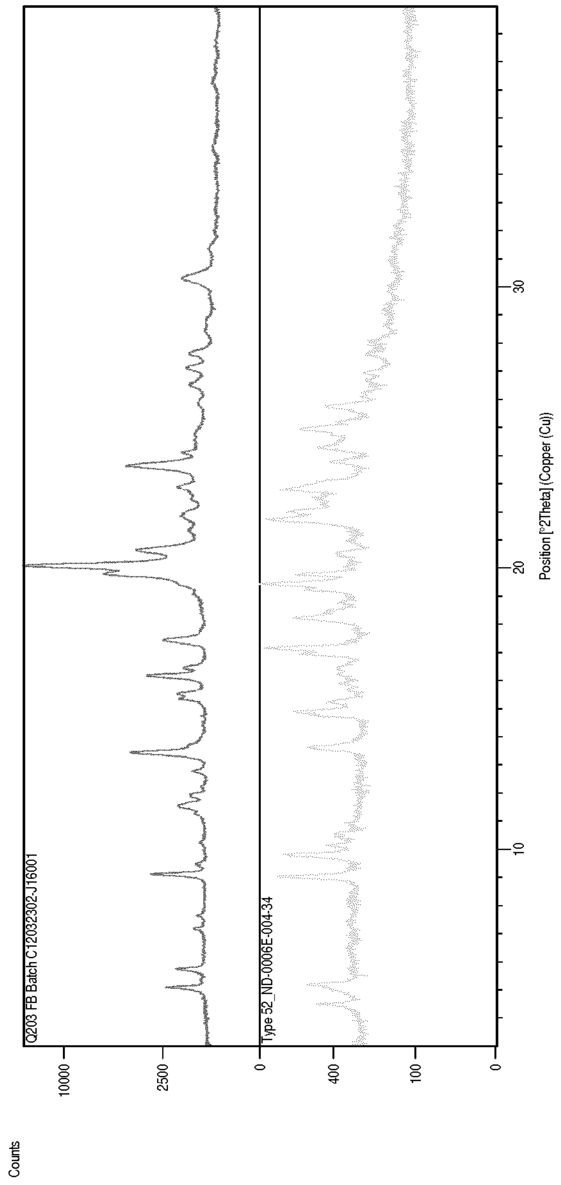
FIG. 75 shows XRPD patterns of Q203 free base (top trace) and ND-0006E-004-34 (Type 52, bottom trace).

Type 52 material was isolated from a RT slurry experiment using salicylic and Q203 free base (1:1 acid/API) in MTBE for 5 days. XRPD analysis of Type 52 solid (ND-0006E-005-33, FIG. 75) showed the material was crystalline and exhibiting similarities with Type 3. Proton NMR analysis (data not shown) is showed no peak shifting, ~0.36 molar eq. of co-former, ~0.40 molar eq. of MTBE suggesting likely a polymorph of Q203 free base.

5.53 Type 53 (Salicylic)

Figure 76:
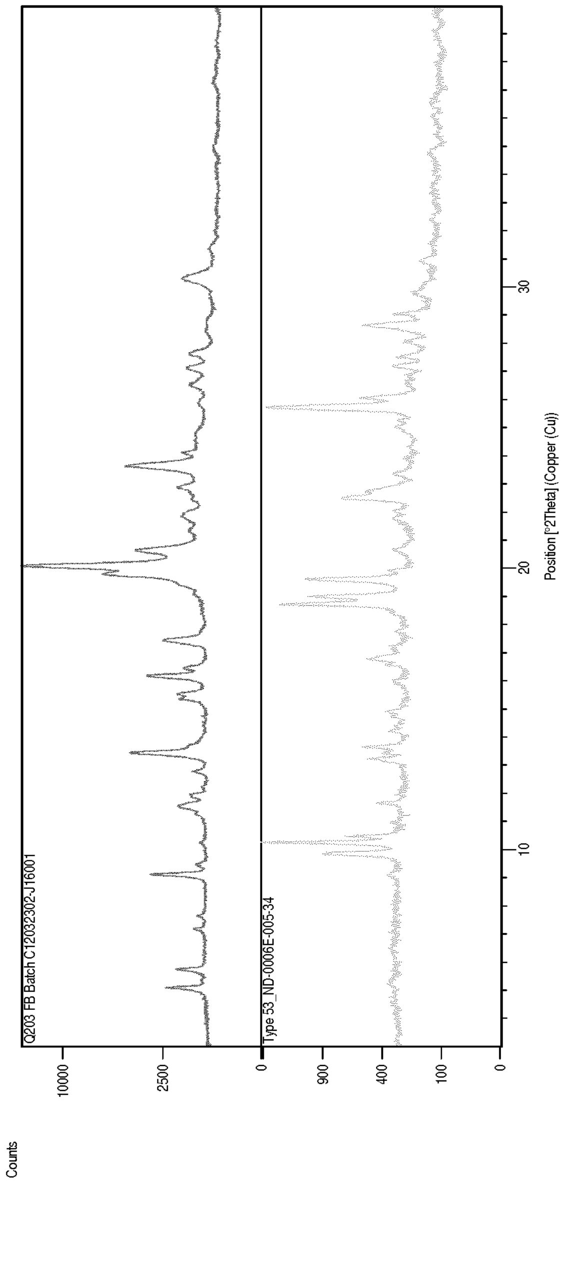
FIG. 76 shows XRPD patterns of Q203 free base (top trace) and ND-0006E-005-34 (Type 53, bottom trace).

Type 53 material was isolated from a sonication experiment using salicylic and Q203 free base (1:1 acid/API) in THF. XRPD analysis of Type 53 solid (ND-0006E-005-34, FIG. 76) showed the material was crystalline. Proton NMR analysis (data not shown) showed no peak shifting, ~1 molar eq. of co-former, ~0.04 molar eq. of THF (~0.4% w/w). TG/DTA analysis (data not shown) showed a weight loss of ~0.9% from 25° C. to ~125° C. likely attributable to moisture then a endotherm is observed at ~132° C. associated with weight loss up to 300° C. likely of ~20% which may be attributable to the loss of salicylic acid. These results suggest potential co-crystal of the Q203 FB but would need to be confirmed by further analysis.

5.54 Type 54 (Methanesulfonic)

Figure 77:
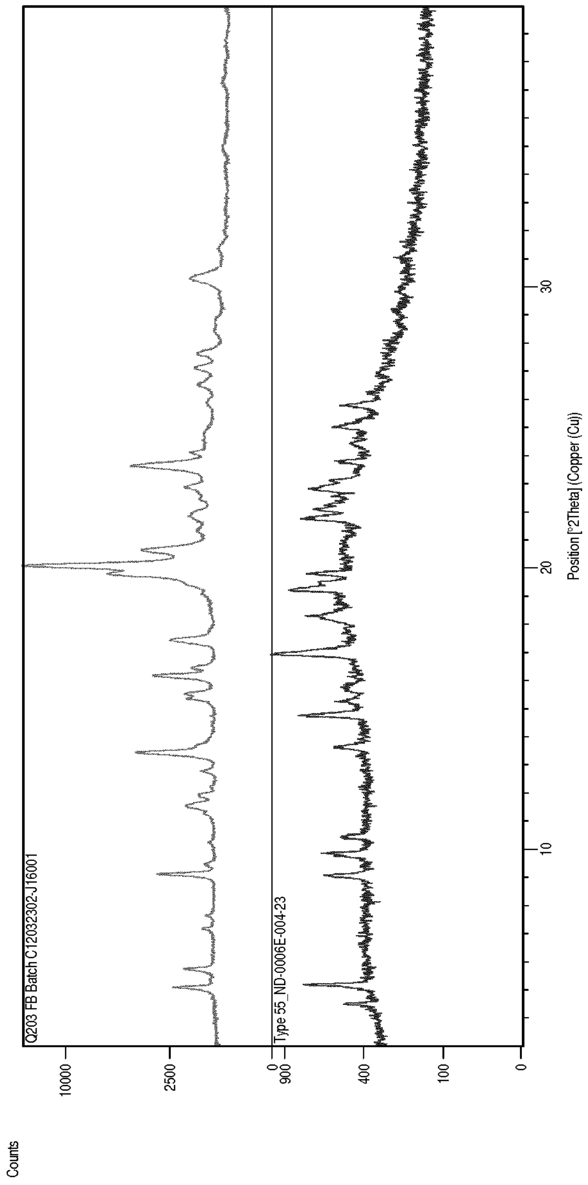
FIG. 77 shows XRPD patterns of Q203 free base (top trace), ND-0006E-004-23 (Type 54, purple trace)

Type 54 material was isolated from an ambient slurry experiment using methanesulfonic acid and Q203 free base 1:1 acid:API) in MTBE for 5 days. XPRD analysis of Type 54 (ND-0006E-004-23) showed the material was disordered crystalline and very similar to Type 3 (FIG. 77). Proton NMR analysis (data not shown) showed peak shifting, ~0.18 molar eq. of MTBE suggesting salt formation with 1:1 stoichiometry.

6 Assessment of Q203 Candidates (Salt/Co-Crystal)

All the data generated from this study have been gathered in the Table below for selection of candidates of particular interest.

TABLE 22

Assessment of Q203 salt/co-crystal solids (sort by co-former)

| Counter-ion (class)[1] | class | Type | XRPD[2] | RH stress (20 C./75 RH)[3] | Ease of process | NMR data (acid:API) | TG/DTA | Aq. Sol (mg/mL)[4] |
|---|---|---|---|---|---|---|---|---|
| 2-furoic | Gras | 13 | ✓✓ | — | slurry (20° C.) sonication slow evap/slurry (40° C.) | No PS, no residual solvent | — | — |
| ketoglutaric (oxoglutaric) | Gras | 16 | ✓✓✓ or ✓✓ | — | RT slurry MTBE | PS at 2.9 ppm ~0.02 mol eq. MTBE 1:1 stoi. | — | — |
| ketoglutaric (oxoglutaric) | Gras | 29 | ✓✓ or ✓ (very lim qty) | — | sonication THF | No PS, ~0.16 mol. eq. THF ~0.9 molr. eq. co-former | — | — |
| saccharin | Gras | 44 | ✓ | — | LAG IPA/water | PS, Possibly IPA hemi-solvate ~0.5 mol. eq. of IPA | — | — |
| saccharin | Gras | 47 | ✓✓✓ (lim qty) | — | HT slurry IPA/water | PS, Trace of IPA, ~0.7 mol. eq. of co-former | — | — |
| urea | Gras | 5 | ✓✓✓ | — | RT slurry MTBE and HT slurry IPA Slow evap THF/MeOH | No PS, No residual solvent | — | — |
| ascorbic | 1 | 43 | ✓✓ or ✓ | — | LAG IPA/water | No PS, no residual solvent ~0.8 mol. eq. co-former | — | — |
| citric | 1 | 14 | ✓✓ | — | RT slurry MTBE | No PS, no residual solvent | — | — |
| fumaric | 1 | 4 | ✓✓✓ | — | slow evap MeOH/THF | no PS, ~0.5 mol. eq. MeOH possibly hemisolvated of MeOH | — | — |
| fumaric | 1 | 15 | ✓✓✓ | — | Obtained 2 times by Slurry (RT and 40 C.) | No PS, no residual solvent | — | — |
| fumaric | 1 | 30 | ✓✓ | — | Obtained once, sonication | No PS, no residual solvent | — | — |
| Galactaric | 1 | 28 | ✓✓✓ or ✓✓ | — | LAG IPA/water | No PS, ~0.07 mol. eq. of IPA- | — | — |
| gluconic | 1 | 38 | ✓✓ | — | co-melt | No PS, no residual solvent | — | — |

TABLE 22-continued

| Counter-ion (class)[1] | class | Type | XRPD[2] | RH stress (20 C./ 75 RH)[3] | Ease of process | NMR data (acid:API) | TG/ DTA | Aq. Sol (mg/ mL)[4] |
|---|---|---|---|---|---|---|---|---|
| Assessment of Q203 salt/co-crystal solids (sort by co-former) | | | | | | | | |
| HCl | 1 | 35 | ✓✓ (lim qty) | — | HT slurry IPA | PS, no residual solvent | — | — |
| HCl | 1 | 36 | ✓✓ (lim qty) | stable | RT slurry MTBE | PS, trace if MTBE | — | <0.31 |
| maleic | 1 | 18 | ✓✓✓ or ✓✓ | — | RT slurry MTBE | PS, ~0.2 mol. eq. MTBE, additional peaks 1:1 stoi. | — | — |
| malic (L) | 1 | 24 | ✓✓ (lim qty) | — | RT slurry MTBE, sonication THF | No PS, no residual solvent, 1 mol. eq. co-former | — | — |
| phosphoric | 1 | 37 | ✓✓✓ | — | LAG acetone | PS, ~0.09 mol. eq. acetone | — | — |
| succinic | 1 | 22 | ✓✓✓ or ✓✓ (lim qty) | stable | RT slurry MTBE | No PS, no residual solvent ~1 mol. eq. co-former | — | <0.47 |
| sulphuric | 1 | 31 | ✓✓✓ or ✓✓ (lim qty) | Deliques-cent | HT slurry IPA | PS, no residual solvent, additional peaks (deg) | — | <0.40 |
| Tartaric (L) | 1 | 21 | ✓✓✓ or ✓✓ (lim qty) | — | RT and HT slurry using MTBE/IPA | No PS, ~0.6 mol. eq. co-former One additional peak | — | — |
| Benzene-sulfonic | 2 | 6 | ✓✓ or ✓ | stable | slow evap THF/acetone | PS, ~0.25 mol. eq. of THF | — | <0.54 |
| Benzene-sulfonic | 2 | 12 | ✓✓ or ✓ | stable | sonication IPA | PS, ~0.03 mol. eq. of THF 1:1 stoi. | — | <0.47 |
| Benzene-sulfonic | 2 | 33 | ✓✓✓ | — | HR slurry IPA | PS, no residual solvent Likely 2:1 stoi. | — | — |
| EDSA | 2 | 9 | ✓✓ or ✓ | stable | slow evap THF/acetone RT slurry MTBE sonication THF | PS, ~0.07 mol. eq. MTBE, 1:1 stoi | — | <0.46 |
| EDSA | 2 | 34 | ✓✓ or ✓ | — | HT slurry IPA | PS, no residual solvent 2:1 stoi | — | — |
| gentisic | 2 | 19 | ✓✓✓ or ✓✓ | — | Obtained once, slurry (RT) | No PS, ~0.1 mol. eq. MTBE, ~0.2 mol. eq. co-former | — | — |
| gentisic | 2 | 27 | ✓✓ or ✓ (very lim qty) | — | slow evap | No PS, ~0.5 mol. eq. THF, ~2 mol. eq. co-former | — | — |
| gentisic | 2 | 42 | ✓✓✓ or ✓✓ | — | LAG | No PS, ~0.14 mol. eq. acetone ~0.7 mol. eq. co-former | — | — |

TABLE 22-continued

Assessment of Q203 salt/co-crystal solids (sort by co-former)

| Counter-ion (class)[1] | class | Type | XRPD[2] | RH stress (20 C./ 75 RH)[3] | Ease of process | NMR data (acid:API) | TG/ DTA | Aq. Sol (mg/ mL)[4] |
|---|---|---|---|---|---|---|---|---|
| MSA | 2 | 54 | ✓✓ (lim qty) | — | RT slurry MTBE | PS, ~0.18 mol. eq. of MTBE 1:1 stoi | — | — |
| NDSA | 2 | 10 | ✓✓ or ✓ | — | Slow evap THF/acetone, sonication THF | PS, ~0.5 mol. eq. THF 2:1 stoi | — | — |
| NDSA | 2 | 11 | ✓✓ | — | Slow evap THF | PS, ~0.7 mol. eq. THF Q203 salt | — | — |
| NDSA | 2 | 17 | ✓✓✓ or ✓✓ | — | RT slurry MTBE | PS, ~0.08 mol. eq. MTBE 2:1 stoi | — | — |
| NDSA | 2 | 26 | ✓✓✓ or ✓✓ | stable | HT slurry IPA | PS, ~0.04 mol. eq. IPA, | — | <0.40 |
| oxalic | 2 | 45 | ✓✓✓ | — | HT slurry acetone | PS, ~0.06 mol. eq. acetone | — | — |
| pamoic | 2 | 50 | ✓✓✓ | — | RT slurry MTBE | No PS,~0.07 mol. eq. MTBE, ~0.65 mol. eq. co-former | — | — |
| pamoic | 2 | 51 | ✓✓✓ | — | Sonication THF | No PS,~0.02 mol. eq. THF, ~0.9 mol. eq. co-former | — | — |
| pTSA | 2 | Pat A | ✓✓✓ | stable | HT slurry IPA | Additional peak @3.45 ppm 2:1 stoi. | — | <0.38 |
| pTSA | 2 | 7 | ✓✓✓ | — | Slow evap acetone, sonication THF | PS, no residual solvent Additional peaks 1:1 stoi | — | — |
| pTSA | 2 | 8 | ✓✓✓ | — | Slow evap THF/acetone | PS, ~0.15 mol. eq. THF 2:1 stoi | — | — |
| pTSA | 2 | 20 | ✓✓✓ | stable | RT slurry MTBE | PS, ~0.01 mol. eq. MTBE 1:1 stoi | — | <0.30 |
| mandelic (DL) | 3 | 23 | ✓✓✓ | — | RT and HT slurry MTBE and IPA, sonication THF | No PS, trace residual solvent, ~0.8 mol. eq. co-former | — | — |
| Nitric | 3 | 49 | ✓✓ or ✓ (very lim qty) | — | Sonication THF | PS, ~0.25 molar eq. THF | — | — |
| salicylic | 3 | 48 | ✓✓✓ | — | HT slurry THF/acetone | No PS, ~0.1 mol. eq. THF, ~0.9 mol. eq. of co-former | — | — |
| salicylic | 3 | 52 | ✓✓ | — | RT slurry MTBE | No PS, ~0.4 mol. eq. MTBE ~0.4 mol. eq. co-former | — | — |

TABLE 22-continued

Assessment of Q203 salt/co-crystal solids (sort by co-former)

| Counter-ion (class)[1] | class | Type | XRPD[2] | RH stress (20 C./ 75 RH)[3] | Ease of process | NMR data (acid:API) | TG/ DTA | Aq. Sol (mg/ mL)[4] |
|---|---|---|---|---|---|---|---|---|
| salicylic | 3 | 53 | ✓✓✓ or ✓✓ | — | Sonication THF | No PS, ~0.04 mol. eq. THF ~1 mol. eq. co-former | Melt onset at 132° C. | — |

[1]Pharmaceutical class, class 1 = least toxic and unrestricted use as salt former, class 2 = low toxicity and good tolerability but not naturally occurring, class 3 = might be interested under particular circumstances

[2]✓✓✓ = good crystallinity, = low crystallinity

[3]Test for deliquescence, sample stressed for several days under 75% RH

[4]Approximate values listed based of measured by aliquot addition on unbuffered water PS: peak shifting; stoi.: stoichiometry acid/API; mol. eq.: molar equivalent; RT and HT: room and high temperature A selection has been made from the previous results above based upon multiple criteria such as polymorphism landscape, crystallinity, class, nature of each Type (salt or potential co-crystal), specific toxicity, thermal behaviour, etc.

The three candidates that the present inventors have identified as particularly useful are the first three entries in the following table (see Table 23).

TABLE 23

Selection of Q203 salt/co-crystal solids (3 candidates shown in bold as first three entries)

| Counter-ion (class)[1] | class | Type | XRPD[2] | RH stress (20 C./ 75 RH)[3] | Ease of process | NMR data (acid:API) | TG/ DTA | Aq. Sol (mg/ mL)[4] |
|---|---|---|---|---|---|---|---|---|
| **HCl** | **1** | **36** | **✓✓ (lim qty)** | **stable** | **RT slurry MTBE** | **PS, trace of MTBE** | — | **<0.31** |
| **phosphoric** | **1** | **37** | **✓✓✓** | — | **LAG acetone** | **PS, ~0.09 mol. eq. acetone** | — | — |
| **pTSA** | **2** | **20** | **✓✓✓** | **stable** | **RT slurry MTBE** | **PS, ~0.01 mol. eq. MTBE 1:1 stoi** | — | **<0.30** |
| 2-furoic | Gras | 13 | ✓✓ | — | slurry (20° C.) sonication slow evap/slurry (40° C.) | No PS, no residual solvent | — | — |
| ketoglutaric (oxoglutaric) | Gras | 16 | ✓✓✓ or ✓✓ | — | RT slurry MTBE | PS at 2.9 ppm ~0.02 mol eq. MTBE 1:1 stoi. | — | — |
| saccharin | Gras | 47 | ✓✓✓ (lim qty) | — | HT slurry IPA/water | PS, Trace of IPA, ~0.7 mol. eq. of co-former | — | — |
| urea | Gras | 5 | ✓✓✓ | — | RT slurry MTBE and HT slurry IPA Slow evap THF/MeOH | No PS, No residual solvent | — | — |
| citric | 1 | 14 | ✓✓ | — | RT slurry MTBE | No PS, no residual solvent | — | — |
| fumaric | 1 | 15 | ✓✓✓ | — | slurry (RT and 40 C.) | No PS, no residual solvent | — | — |
| fumaric | 1 | 30 | ✓✓ | — | Obtained once, sonication | No PS, no residual solvent | — | — |
| Galactaric | 1 | 28 | ✓✓✓ or ✓✓ | — | LAG IPA/water | No PS, ~0.07 mol. eq. of IPA- | — | — |
| gluconic | 1 | 38 | ✓✓ | — | co-melt | No PS, no residual solvent | — | — |

TABLE 23-continued

Selection of Q203 salt/co-crystal solids (3 candidates shown in bold as first three entries)

| Counter-ion (class)[1] | class | Type | XRPD[2] | RH stress (20 C./75 RH)[3] | Ease of process | NMR data (acid:API) | TG/DTA | Aq. Sol (mg/mL)[4] |
|---|---|---|---|---|---|---|---|---|
| HCl | 1 | 35 | ✓✓ (lim qty) | — | HT slurry IPA | PS, no residual solvent | — | — |
| maleic | 1 | 18 | ✓✓✓ or ✓✓ | — | RT slurry MTBE | PS, ~0.2 mol. eq. MTBE, additional peaks 1:1 stoi. | — | — |
| malic (L) | 1 | 24 | ✓✓ (lim qty) | — | RT slurry MTBE, sonication THF | No PS, no residual solvent, 1 mol. eq. co-former | — | — |
| phosphoric | 1 | 37 | ✓✓✓ | — | LAG acetone | PS, ~0.09 mol. eq. acetone | — | — |
| succinic | 1 | 22 | ✓✓✓ or ✓✓ (lim qty) | stable | RT slurry MTBE | No PS, no residual solvent ~1 mol. eq. co-former | — | <0.47 |
| Tartaric (L) | 1 | 21 | ✓✓✓ or ✓✓ (lim qty) | — | RT and HT slurry using MTBE/IPA | No PS, ~0.6 mol. eq. co-former One additional peak | — | — |
| Benzene-sulfonic | 2 | 12 | ✓✓ or ✓ | stable | sonication IPA | PS, ~0.03 mol. eq. of THF 1:1 stoi. | — | <0.47 |
| Benzene-sulfonic | 2 | 33 | ✓✓✓ | — | HR slurry IPA | PS, no residual solvent Likely 2:1 stoi. | — | — |
| EDSA | 2 | 9 | ✓✓ or ✓ | stable | slow evap THF/acetone RT slurry MTBE sonication THF | PS, ~0.07 mol. eq. MTBE, 1:1 stoi | — | <0.46 |
| EDSA | 2 | 34 | ✓✓ or ✓ | — | HT slurry IPA | PS, no residual solvent 2:1 stoi | — | — |
| gentisic | 2 | 27 | ✓✓ or ✓ (very lim qty) | — | slow evap | No PS, ~0.5 mol. eq. THF, ~2 mol. eq. co-former | — | — |
| gentisic | 2 | 42 | ✓✓✓ or ✓✓ | — | LAG | No PS, ~0.14 mol. eq. acetone ~0.7 mol. eq. co-former | — | — |
| MSA | 2 | 54 | ✓✓ (lim qty) | — | RT slurry MTBE | PS, ~0.18 mol. eq. of MTBE 1:1 stoi | — | — |
| NDSA | 2 | 17 | ✓✓✓ or ✓✓ | — | RT slurry MTBE | PS, ~0.08 mol. eq. MTBE 2:1 stoi | — | — |
| NDSA | 2 | 26 | ✓✓✓ or ✓✓ | stable | HT slurry IPA | PS, ~0.04 mol. eq. IPA 1:1 stoi | — | <0.40 |
| oxalic | 2 | 45 | ✓✓✓ | — | HT slurry acetone | PS, ~0.06 mol. eq. acetone | — | — |

TABLE 23-continued

Selection of Q203 salt/co-crystal solids (3 candidates shown in bold as first three entries)

| Counter-ion (class)[1] | class | Type | XRPD[2] | RH stress (20 C./75 RH)[3] | Ease of process | NMR data (acid:API) | TG/DTA | Aq. Sol (mg/mL)[4] |
|---|---|---|---|---|---|---|---|---|
| pamoic | 2 | 51 | ✓✓✓ | — | Sonication THF | No PS,~0.02 mol. eq. THF, ~0.9 mol. eq. co-former | — | — |
| pTSA | 2 | Pat A | ✓✓✓ | stable | HT slurry IPA | Additional peak @3.45 ppm 2:1 stoi. | — | <0.38 |
| pTSA | 2 | 20 | ✓✓✓ | stable | RT slurry MTBE | PS, ~0.01 mol. eq. MTBE 1:1 stoi | — | <0.30 |
| mandelic (DL) | 3 | 23 | ✓✓✓ | — | RT and HT slurry MTBE and IPA, sonication THF | No PS, trace residual solvent, ~0.8 mol. eq. co-former | — | — |
| Nitric | 3 | 49 | ✓✓ or ✓ (very lim qty) | — | Sonication THF | PS, ~0.25 molar eq. THF | — | — |
| salicylic | 3 | 48 | ✓✓✓ | — | HT slurry THF/acetone | No PS, ~0.1 mol. eq. THF, ~0.9 mol. eq. of co-former | — | — |
| salicylic | 3 | 52 | ✓✓ | — | RT slurry MTBE | No PS, ~0.4 mol. eq. MTBE ~0.4 mol. eq. co-former | — | — |
| salicylic | 3 | 53 | ✓✓✓ or ✓✓ | — | Sonication THF | No PS, ~0.04 mol. eq. THF ~1 mol. eq. co-former | Melt onset at 132° C. | — |

[1]Pharmaceutical class, class 1 = least toxic and unrestricted use as salt former, class 2 = low toxicity and good tolerability but not naturally occurring, class 3 = might be interested under particular circumstances

[2]✓✓✓ = good crystallinity, = low crystallinity

3Test for deliquescence, sample stressed for several days under 75% RH

[4]Approximate values listed based of measured by aliquot addition on unbuffered water PS: peak shifting; stoi.: stoichiometry acid/API; mol. eq.: molar equivalent; RT and HT: room and high temperature

7 Scale Up of Selected Salts

7.1 P-TSA (Nd-6E-012-01)

API (1 g) was added to a scintillation vial containing THF (18 ml). Seeds of Type 20 solid (ND-0007E-004-16) were added to the solution, which did not dissolve. pTSA dissolved in acetone (342 mg, 18 ml) was added to the API solution. Precipitation was observed with stirring. Proton NMR analysis after T=1d suggested the pTSA salt had formed (1.3 molar eq. with additional peak at 8.6 ppm). The solid was isolated and slurried in MTBE for 3 days. XRPD analysis of the resultant solid confirmed Type 20.

7.2 Phosphate (ND-6E-012-02)

Concentrated $H_2PO_4$ (122.8 ul) was added to a scintillation vial containing acetone (7.5 ml). Seeds of Type 37 solid (ND-0007E-008-13) were added to the solution, which did not dissolve. API (1 g) was added to the vial with stirring resulting in a block of solid. This was vortexed until a thick slurry was obtained. The slurry (not well mixable) became more mixable after ~10 mins at 40° C. A pull was taken at T=1 day for proton NMR analysis which showed ~0.43 molar eq. of acetone. The slurry was left for T=5 days, prior to isolation of the solid by filtration. XRPD analysis showed Type 37.

7.3 HCl (ND-6E-012-03)

Concentrated HCl (147.3 ul) was added to a scintillation vial containing THF (18 ml). Seeds of Type 36 solid (ND-0007E-004-18) were added to the solution, which dissolved. The HCl/THF solution was added to API (1 g) resulting in a solution. The solution was again seeded with T36 solid, which dissolved. The solution was subjected to evaporation under nitrogen for ~5 mins until the solution became a haze. Seeds of T36 were added resulting in a suspension. The solution was evaporated under nitrogen with stirring. XRPD showed a novel Type 55. Proton NMR analysis showed a peak shifting confirming salt formation.

8 pH Profile Analysis

The pH profile has been assessed on the three salt candidates of Q203 (monotosylate, phosphate and HCl). The HPLC method is detailed in Section 2.3.6.

8.1 HPLC Method Check

The HPLC method was initially checked for suitability of use, and a working range from 0.0625 mg/mL to 0.5 mg/mL was established for Q203. (Note diluent was changed to methanol, as material was not soluble in diluent listed in method supplied). Samples from solubility experiments were diluted where required so the API concentration fell within the working concentration range. A linearity of R2=0.999 was found showing a really good fit (data not shown).

8.2 pH Solubility Profiling

Solubility of salts at pH 1, 4.5, 6.8 and 7.5 was determined as described in section 2.3.6 and 2.3.7. pTSA remained the same pattern following slurrying in pH 1 buffer and exhibited an average solubility of ~0.33 mg/mL. However at pH 4.5 and above the pTSA salt converted to Type 28 which was found to be a polymorph of the freebase from XRPD and proton NMR analyses and had shown a very limited solubility (<0.00037 mg/ml), see table 25.

Figure 78:
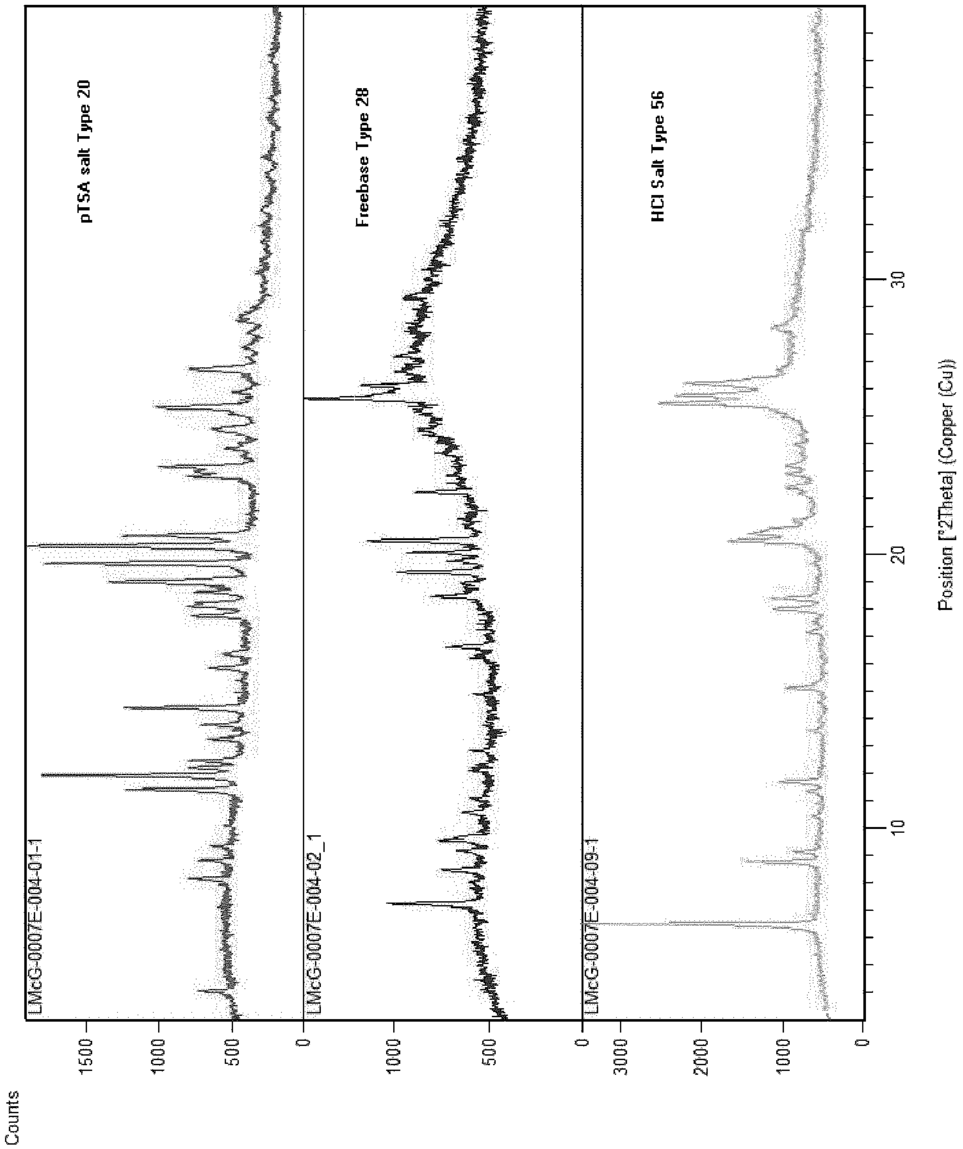
FIG. 78 shows XRPD traces of solids isolated post pH solubility experiments

This was also the case for the phosphate salt at pH 4.5 and above, but following slurrying in pH 1 buffer converted to a new HCl salt, Type 56. Type 56 was also observed from all solids isolated from HCl solubility experiments. The greatest solubility was ~5.58 mg/mL observed from HCl salt Type 56 at pH 1 (sample LMcG-0007E-004-09_1 was discounted as this figure was significantly lower than other three values, and may have been a dilution error). Selected results (XRPD traces of solids isolated after pH solubility experiments) are also shown in FIG. 78.

TABLE 24

Results of pH solubility profiling

| Sample no (LMcG-0007E-004-) | Input | Final pH | Pull time (hrs) | XRPD | NMR | HPLC concentration based on avg std (mg/ml) |
|---|---|---|---|---|---|---|
| — | Ditosylate | 1 | — | — | — | 1.45 (client result) |
| 01_1 | pTSA salt, Type 20 (ND-0006E-012-01) | 1.2 | 24 | p-TSA salt T20 crystalline | — | 0.33 |
| 01_2 | pTSA salt, Type 20 (ND-0006E-012-01) | 1.14 | 24 | p-TSA salt T20 crystalline | — | 0.32 |
| 02_1 | pTSA salt, Type 20 (ND-0006E-012-01) | 4.1 | 23 | Type 28 disordered | — | 3.66E−04 |
| 02_2 | pTSA salt, Type 20 (ND-0006E-012-01) | 4.47 | 23 | Type 28 disordered | — | 3.33E−04 |
| 03_1 | pTSA salt, Type 20 (ND-0006E-012-01) | 6.45 | 22.5 | Type 28 disordered | no PS | 3.12E−04 |
| 03_2 | pTSA salt, Type 20 (ND-0006E-012-01) | 6.71 | 22.5 | Type 28 disordered | — | 3.07E−04 |
| 04_1 | pTSA salt, Type 20 (ND-0006E-012-01) | 7.49 | 72 | Type 28 disordered | — | 1.20E−04 |
| 04_2 | pTSA salt, Type 20 (ND-0006E-012-01) | 7.3 | 72 | Type 28 disordered | — | 3.97E−05 |
| 05_1 | Phosphate salt, Type 37 (ND-0006E-012-02) | 1.23 | 24 | T56 HCl salt v. disordered | — | 5.33 |
| 05_2 | Phosphate salt, Type 37 (ND-0006E-012-02) | 1.18 | 24 | T56 HCl salt v. disordered | higher PS | 5.64 |
| 06_1 | Phosphate salt, Type 37 (ND-0006E-012-02) | 4.1 | 23 | Type 28 disordered | — | 3.84E−04 |
| 06_2 | Phosphate salt, Type 37 (ND-0006E-012-02) | 4.27 | 23 | Type 28 disordered | — | 3.36E−04 |
| 07_1 | Phosphate salt, Type 37 (ND-0006E-012-02) | 6.33 | 22.5 | Type 28 disordered | — | 2.80E−04 |
| 07_2 | Phosphate salt, Type 37 (ND-0006E-012-02) | 6.79 | 22.5 | Type 28 disordered | — | 2.97E−04 |
| 08_1 | Phosphate salt, Type 37 (ND-0006E-012-02) | 7.54 | 72 | Type 28 disordered | — | 6.39E−05 |
| 08_2 | Phosphate salt, Type 37 (ND-0006E-012-02) | 7.41 | 72 | Type 28 disordered | — | 4.10E−05 |
| 09_1 | HCl salt, Type 36 (ND-0006E-012-03) | 1.16 | 24 | T56 HCl salt crystalline | PS | 2.54[1] |
| 09_2 | HCl salt, Type 36 (ND-0006E-012-03) | 1.09 | 24 | T56 HCl salt crystalline | slight PS | std (mg/ml) 5.76 |
| 10_1 | HCl salt, Type 36 (ND-0006E-012-03) | 4.34 | 23 | T56 HCl salt crystalline | slight PS | 3.23E−04 |
| 10_2 | HCl salt, Type 36 (ND-0006E-012-03) | 4.34 | 23 | T56 HCl salt crystalline | — | 3.07E−04 |
| 11_1 | HCl salt, Type 36 (ND-0006E-012-03) | 6.99 | 22.5 | T56 HCl salt crystalline | — | 2.85E−04 |
| 11_2 | HCl salt, Type 36 (ND-0006E-012-03) | 6.9 | 22.5 | T56 HCl salt crystalline | — | 2.77E−04 |
| 12_1 | HCl salt, Type 36 (ND-0006E-012-03) | 7.28 | 72 | T56 HCl salt crystalline | — | 3.28E−05 |
| 12_2 | HCl salt, Type 36 (ND-0006E-012-03) | 7.28 | 72 | T56 HCl salt crystalline | — | 3.57E−05 |

[1] possible dilution error 8.3 Conclusions of the pH Profile Analysis pTSA salt remained stable at pH 1 buffer and had a solubility of ~0.33 mg/mL, however at pH 4.5 and above converted to freebase (type 28) which had lower solubility. Phosphate salt was not stable in any pH buffer, at pH 1 converted to HCl Type 56 and at pH 4.5 and above converted to freebase. Type 36 HCl salt converted to new type HCl salt Type 56 in all buffers tested.

Improvement of the solubility was found for the three candidates compared to the free base and the current candidate (ditosylate salt). It should be noted that below pH 4.5, phosphate and pTSA exhibited a conversion to the free base suggesting some degree of instability.

On the other hand, HCl salt exhibited a higher solubility and under the conditions tested no conversion to the free base was observed. This may be explained by low wettability, kinetic factors (time, stirring effect).

9 Conclusion

A salt screen was performed on Q203 using thirty seven salt formers in various solvent systems. More than 50 new Types were observed which showed a very high tendency of Q203 to generate new patterns (polymorph of the free base but mainly salts and potential co-crystals).

These new patterns have been analysed by different analytical techniques (eg. XRPD, proton NMR, aqueous solubility when sufficient material was available).

A selection of three salt candidates for further pH profile analysis has been made upon multiple criteria such as polymorphism landscape, crystallinity, class, nature of each Type (salt or potential co-crystal), specific toxicity, thermal behaviour, etc. All potential co-crystals have not been considered as further characterisation would be needed to confirm the nature of these solids (whether or not co-crystal). Pharmaceutical class of the counter ion has also been taken into account (HCl and phosphoric acid are considered as Class 1 which are defined as least toxic and unrestricted use as salt former. The monotosylate salt has been chosen although it is considered as Class 2 (low toxicity and good tolerability but not naturally occurring). By comparison between mono and ditosylate, the monotosylate would exhibit a lower toxicity as only one molecule of counter ion per molecule of API will be present opposed as the ditosylate salt.

It should be noted that other candidates may be of interest for further development but further investigation would be needed and compared to these 3 candidates.

Improvement of the solubility was found for the three candidates compared to the free base and the ditosylate salt. It should be noted that below pH 4.5, phosphate and pTSA exhibited a conversion to the free base suggesting some instability.

On the other hand, HCl salt exhibited the higher solubility and under the conditions tested no conversion to the free base was observed. This may be explained by low wettability, kinetic factors (time, stirring effect) especially above pH4.

APPENDIX 1

TABLE 25

Summary of the observed solids of Q203 (sorted out by co-former)

| Type | Co-former | Comments/ Tentative Assignments |
|---|---|---|
| 13 | 2-furoic | Crystalline, prepared by a range of techniques and solvents<br>$^1$H NMR suggests no salt formation<br>Potential co-crystal or polymorph of Q203 free base |
| 43 | ascorbic | Disordered crystalline, prepared by LAG using a mixture of IPA/water<br>Proton NMR: no PS, ~0.8 molar eq. co-former, no residual IPA |
| 6 | benzenesulfonic | Disordered crystalline, prepared by slow evaporation using THF/acetone<br>$^1$H NMR suggests salt formation with ~0.25 molar eq. of THF<br>Q203 benzenesulfonate salt (1:1 or 2:1 stoichiometry) |
| 12 | benzenesulfonic | Crystalline, prepared by sonication using THE<br>$^1$H NMR suggests salt formation with ~0.03 molar eq. of THF<br>Q203 benzenesulfonate (1:1 stoichiometry) |
| 33 | benzenesulfonic | Crystalline, prepared by HT slurrying for 7 d using IPA<br>$^1$H NMR suggests salt formation with no residual solvent<br>Q203 benzenesulfonate salt (likely 2:1 stoichiometry) |
| 14 | citric | Crystalline, prepared by RT slurrying for 7 d using MTBE<br>$^1$H NMR suggests no salt formation<br>Potential co-crystal or polymorph of Q203 free base |
| 9 | ethane-1,2-disulfonic | Disordered crystalline, prepared by a range of techniques and solvents<br>$^1$H NMR suggests salt formation with ~0.07 molar eq. of MTBE<br>Q203 edisylate (potential 1:1 stoichiometry) |
| 34 | ethane-1,2-disulfonic | Disordered crystalline, prepared by HT slurrying for 7 d using IPA<br>$^1$H NMR suggests salt formation with no residual solvent<br>Q203 edisylate salt (2:1 stoichiometry) |
| 4 | fumaric | Crystalline, prepared by slow evaporation using a mixture of THF/MeOH<br>$^1$H NMR suggests no salt formation and~0.5 eq residual MeOH<br>Potential MeOH hemi-solvate of co-crystal or polymorph of Q203 free base |
| 15 | fumaric | Crystalline, prepared by RT/HT slurrying for 7 d using MTBE/IPA<br>$^1$H NMR suggests no salt formation (~0.7 molar eq. fumaric acid)<br>Potential co-crystal or polymorph of Q203 free base |
| 30 | fumaric | Crystalline, prepared by sonication using THF<br>$^1$H NMR shows no peak shifting, no residual solvent and ~0.9 molar eq. of fumaric acid suggesting possible co-crystal or polymorph of Q203 free base. |
| 28 | galactaric, gluconic | Crystalline, prepared by LAG experiments using a mixture of IPA/water and acetone from galactaric and gluconic respectively<br>$^1$H NMR suggests no salt formation (~0.08 molar eq. IPA).<br>Further obtained as part of the pH profile analysis so likely polymorph of the Free base |
| 19 | gentisic | Crystalline (similar to T3), prepared by RT slurrying for 7 d using MTBE<br>$^1$H NMR suggests no salt formation<br>(~0.1 eq residual MTBE and 0.2 eq. free acid)<br>Potential co-crystal or polymorph of Q203 free base |

TABLE 25-continued

| Summary of the observed solids of Q203 (sorted out by co-former) | | |
|---|---|---|
| Type | Co-former | Comments/ Tentative Assignments |
| 27 | gentisic | Disordered crystalline, prepared by slow evaporation using a mixture THF/methanol $^1$H NMR shows no peak shifting, with ~0.5 molar eq. of THF, ~2 mol. eq. of co-former, suggesting possible THF hemisolvate of co-crystal or polymorph of the free base. |
| 42 | gentisic | Disordered crystalline, prepared by LAG using a mixture of IPA/water |
| 38 | gluconic | Crystalline, prepared by co-melt Proton NMR: no PS as expected, no solvent, no presence of co-former TG/DTA: melt at ~165° C. Likely polymorph of the free base |
| 35 | HCl | Disordered crystalline, prepared by HT slurrying for 7 d using IPA $^1$H NMR suggests salt formation with no residual solvent Q203 HCl salt. The stoichiometry has not been determined |
| 36 | HCl | Crystalline, prepared by HT slurrying for 7 d using IPA $^1$H NMR suggests salt formation with ~0.007 molar eq. of MTBE Q203 HCl salt. The stoichiometry has not been determined |
| 55 | HCl | Crystalline with the presence of disordered material, prepared by evaporation from THE Proton NMR: shifting confirming salt formation. |
| 56 | HCl | Crystalline with the presence of disordered material, generated as part of the pH profile analysis from Type 55 and phosphate salt at pH1 Proton NMR: shifting confirming salt formation |
| 16 | ketoglutaric (oxoglutaric) | Crystalline, prepared by RT slurrying for 7 d using MTBE $^1$H NMR shows possibly PS at 2.9 ppm, 0.02 eq residual MTBE. Nature of this Type needs to be confirmed |
| 29 | ketoglutaric (oxoglutaric) | Disordered crystalline, prepared by sonication using THE $^1$H NMR shows no peak shifting, with ~0.16 molar eq. of THF and ~0.9 molar eq. of ketoglutaric acid suggesting possible co-crystal or polymorph of Q203 free base. |
| 18 | maleic | Crystalline (similar to T19), prepared by RT slurrying for 7 d using MTBE $^1$H NMR suggests salt formation and ~0.2 eq residual MTBE Potential Q203 maleate (1:1 stoichiometry), possible non-stoichiometric MTBE solvate |
| 24 | malic (L) | Crystalline, prepared by RT slurrying using MTBE and by sonication using THF $^1$H NMR shows no peak shifting, no residual solvent and ~1 molar eq. of malic acid suggesting possible co-crystal or polymorph of the free base. |
| 23 | mandelic (DL) | Crystalline, prepared by RT and HT slurrying using MTBE and IPA, and by sonication 1H NMR shows no Peak shifting and ~0.8 molar eq. of mandelic acid suggesting possible co-crystal or polymorph of the free base. |
| 54 | methanesulfonic | Disordered crystalline, prepared by RT slurry for 7 d using MTBE Very similar to Type 3 Proton NMR: peak shifting with ~0.18 molar eq. of MTBE suggesting likely MSA salt of Q203 with a 1:1 stoichiometry. |
| 2 | multiple co-formers | Crystalline, prepared by slow evaporation using THE/MeOH $^1$H NMR suggests no salt formation and no visible degradation Potential polymorph of Q203 free base |
| 3 | multiple co-formers | Crystalline, prepared by a range of techniques and solvents $^1$H NMR suggests no salt formation. Potential polymorph of Q203 free base |
| 25 | multiple co-formers | Crystalline, prepared by multiple solvents and techniques obtained as pure or as a mixture with Type 3. This suggests polymorph of the free base. But $^1$H NMR analysis of material from maleic suggests salt formation with residual solvent (~0.5 molar eq THF). Likely a THF hemi-solvate of the salt of Q203. This may be explained by possible salt formation in-situ during NMR preparation sample. |
| 32 | multiple co-formers and stoichiometry | Crystalline, prepared by HT slurrying for 7 d using IPA $^1$H NMR shows no peak shifting, no residual solvent and ~0.2 molar eq. of ketoglutaric acid. As obtained from multiple co-formers, likely a polymorph of Q203 free base. |
| 39 | multiple co-formers | Crystalline, prepared from various co-formers (malonic, pyruvic and saccharin) by co-melting technique suggesting polymorph of the free base Proton NMR of saccharin and pyruvic solids showed salt formation suggesting salt formation had occurred during NMR sample preparation. |
| 40 | multiple co-formers | Crystalline, prepared from various co-formers (gluconic, malonic, pyruvic. . .) and various techniques co-melting technique suggesting polymorph of the free base |

TABLE 25-continued

Summary of the observed solids of Q203 (sorted out by co-former)

| Type | Co-former | Comments/ Tentative Assignments |
|---|---|---|
| 41 | multiple co-formers | Crystalline, prepared from various co-formers (ascorbic, lactobionic, galactaric) and techniques (HT slurry, LAG) Likely polymorph of the free base |
| 1 | n/a | material, crystalline, free based $^{1}H$ NMR analysis showed no visible degradation and trace of residual solvent (may be acetone around ~80 ppm). |
| 10 | naphtalene-1,5-disulfonic | Crystalline, prepared by a range of techniques and solvents $^{1}H$ NMR suggests salt formation and ~0.5 molar eq. residual THF Potential THF hemisolvate of Q203 napthalenedisulfonate (2:1 stoichiometry) |
| 11 | naphtalene-1,5-disulfonic | Crystalline (similar to T10), prepared by slow evaporation using THF $^{1}H$ NMR suggests salt formation and ~0.7 molar eq. residual THF Potential THF solvate of Q203 napthalenedisulfonate Stoichiometry not determined due to the presence of free acid |
| 17 | naphtalene-1,5-disulfonic | Crystalline (similar to T11), prepared by RT slurrying for 7 d using MTBE $^{1}H$ NMR suggests salt formation with ~0.08 molar eq. of MTBE Potential Q203 NDSA salt (2:1 stoichiometry) |
| 26 | naphtalene-1,5-disulfonic | Crystalline, prepared by slow evap, followed by HT slurrying for 7 d using IPA $^{1}H$ NMR suggests salt formation (~0.04 molar eq. IPA). The stoichiometry needs to be confirmed |
| 49 | nitric | Disordered crystalline, prepared by sonication using THF Very similar to Type 3 + additional peaks Proton NMR: peak shifting with ~0.25 molar eq. of THF suggesting likely Type 49 to be a nitrate salt of Q203. |
| 45 | oxalic | Crystalline, prepared by HT slurry using acetone Proton NMR: peak shifting with ~0.06 molar eq. of acetone. Stoichiometry not determined. Oxalate salt of Q203. |
| 46 | oxalic | Crystalline, prepared by HT slurry using methanol Proton NMR: no peak shifting. Stoichiometry not determined. Likely polymorph of the free base. |
| 50 | pamoic | Crystalline, prepared by RT slurry using MTBE Similarities with Type 3 Proton NMR: no peak shifting with ~0.07 molar eq. of MTBE and ~0.65 molar eq. of co-former Possibly polymorph of Q203 free base or co-crystal. |
| 51 | pamoic | Crystalline, prepared by sonication using THF Proton NMR: no PS, ~0.9 molar eq. co-former, ~0.02 molar eq. of THF Potential polymorph or co-crystal of Q203. |
| 37 | phosphoric | Crystalline, prepared by HT slurry and by LAG using acetone Proton NMR showed peak shifting with ~0.09 molar eq. of acetone Suggesting Q203 phosphate salt. The stoichiometry has not been determined |
| Pat A | p-toluenesulfonic | Crystalline, prepared by slow evap. then HT slurrying using IPA, XRPD pattern similar to the ditosylate salt (Pattern A) $^{1}H$ NMR confirmed salt formation with a 2:1 stoichiometry |
| 7 | p-toluenesulfonic | Crystalline, prepared by a range of techniques and solvents $^{1}H$ NMR suggests salt formation with no residual solvents. Additional peaks were observed. Q203 tosylate (potential 1:1 stoichiometry) |
| 8 | p-toluenesulfonic | Crystalline, prepared by slow evaporation using THF/acetone $^{1}H$ NMR suggests salt formation with ~0.15 molar eq. of THF Q203 tosylate (potential 2:1 stoichiometry) |
| 20 | p-toluenesulfonic | Crystalline, prepared by RT slurrying for 7 d using MTBE $^{1}H$ NMR suggests salt formation (~0.01 molar eq. MTBE) Q203 tosylate (1:1 stoichiometry) |
| 44 | saccharin | Disordered material, very similar to Type 41, prepared by LAG using a mixture of IPA/water. Proton NMR: peak shifting, ~1 molar eq. of saccharin and ~0.5 molar eq. of IPA suggesting IPA hemisolvate of saccharin salt |
| 47 | saccharin | Crystalline, prepared by HT slurry using a mixture of IPA/water Proton NMR: peak shifting with trace of IPA, ~0.7 mol. eq. of co-former suggesting salt formation of Q203 saccharin salt. |
| 48 | salicylic | Crystalline, prepared by HT slurry using a mixture of THF/acetone Proton NMR: no peak shifting, ~0.9 molar eq. co-former, ~0.1 molar eq. of THF and no residual acetone suggesting potential co-crystal or polymorph of the free base. |
| 52 | salicylic | Crystalline, prepared by RT slurry using MTBE Similarities with Type 3 Proton NMR: no PS, ~0.4 molar eq. co-former, ~0.4 molar eq. of MTBE Likely polymorph of Q203. |

TABLE 25-continued

| Summary of the observed solids of Q203 (sorted out by co-former) | | |
|---|---|---|
| Type | Co-former | Comments/ Tentative Assignments |
| 53 | salicylic | Crystalline, prepared by sonication using THF<br>Proton NMR: no PS, ~1.0 molar eq. co-former, ~0.04 molar eq. of THF<br>TG/DTA: melt at ~132° C.<br>Potential co-crystal of Q203. |
| 22 | succinic | Crystalline, prepared by RT slurrying for 7 d using MTBE<br>$^{1}$H NMR suggests salt formation (~0.01 molar eq. MTBE)<br>Potential Q203 tosylate (1:1 stoichiometry) |
| 31 | sulphuric | Crystalline, prepared by HT slurrying for 7 d using IPA<br>$^{1}$H NMR suggests salt formation with no residual solvent and the presence of additional peaks (possibly degradation).<br>The stoichiometry has not been determined |
| 21 | tartaric (L) | Crystalline, prepared by RT/HT slurrying for 7 d using MTBE/IPA<br>$^{1}$H NMR suggests no salt formation<br>(~0.6eq tartaric acid + unknown peak at 8.1 ppm)<br>Potential co-crystal or polymorph of Q203 free base |
| 5 | urea | Crystalline, prepared by a range of techniques and solvents<br>$^{1}$H NMR suggests no salt formation, no residual solvent<br>Potential co-crystal or polymorph of Q203 free base |

Example 3

6-chloro-2-ethyl-N-(4-(4-(4-(trifluoromethoxy)phenyl) piperidine-1-yl)benzyl)imidazo[1,2-a]pyridine-3-carboxamide (Q203)-ditosylate form A was subjected to stability experiments. More specifically, samples of Q203-ditosylate form A were exposed to an environment of 60% RH (relative humidity) and 25° C. for periods of time between 6 months and 60 months. Furthermore, further stability experiments were done with some samples of Q203-ditosylate form A under accelerated conditions (40° C.-75% relative humidity (RH)). These experiments under accelerated conditions were done for a period of up to 6 months. Subsequently, samples were analyzed by HPLC and checked for impurities. It turned out that under conditions of 25° C. and 60% RH, Q203-ditosylate form A remains stable and does not decompose or otherwise deteriorates and there were only minor impurities that could be identified in the corresponding HPLC-chromatograms (chromatogram traces not shown). The results are summarized in the following table:

TABLE 27

| Stability results for form A of Q203-ditosylate at 25° C./60% RH | |
|---|---|
| Time [months] | Purity [%] (as measured by HPLC) |
| 0 | >98% |
| 6 | >98% |
| 12 | >98% |
| 24 | >98% |
| 36 | >98% |
| 48 | >98% |
| 60 | >98% |

It can be seen that the purity remains >98% and does not show any sign of decomposition or deterioration.

Furthermore, in the experiments under accelerated conditions, there was no decomposition for a period up until 6 months when the sample still showed a purity of >98% (data not shown).

From these data it can be concluded that Q203-ditosylate form A is stable under long-term storage conditions of 25° C. and 60% RH for up to 60 months and under accelerated conditions of 40° C. and 75% RH up to 6 months.

The invention claimed is:

1. Compound 6-chloro-2-ethyl-N-(4-(4-(4 (trifluoromethoxy)phenyl)piperidine-1-yl)benzyl)imidazo[1,2-a] pyridine-3-carboxamide ditosylate having the structure

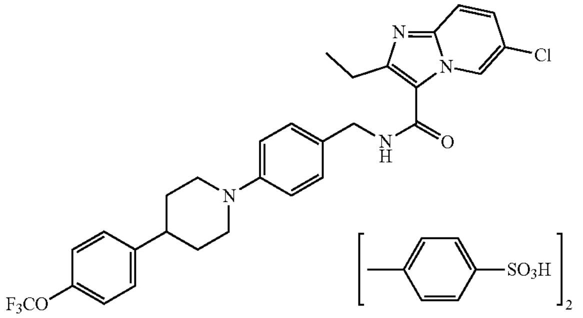

having an XRPD spectrum essentially as shown in FIG. 1.

2. The compound according to claim 1, having a differential scanning calorimetry (DSC) thermogram showing a single endotherm peak with an onset of 235° C.-237° C.

3. The compound according claim 1, being produced by a method comprising the steps:

providing, in any order, 6-chloro-2-ethyl-N-(4-(4-(4-(trifluoromethoxy)phenyl)piperidine-1-yl)benzyl)imidazo [1,2-a]pyridine-3-carboxamide free base and para-toluenesulphonic acid in a stoichiometric ratio of 1:2;

mixing and dissolving them in a suitable solvent or solvent mixture; and evaporating the solvent or solvent mixture.

4. The compound according to claim 3, wherein the solvent or solvent mixture is isopropylalcohol (IPA), tetrahydrofuran (THF), acetone or a mixture of THE and acetone.

5. A mono-acid addition salt of 6-chloro-2-ethyl-N-(4-(4-(4-(trifluoromethoxy)phenyl)piperidine-1-yl)benzyl)imidazo[1,2-a]pyridine-3-carboxamide which is 6-chloro-2-ethyl-N-(4-(4-(4-(trifluoromethoxy)phenyl)piperidine-1-yl) benzyl)imidazo[1,2-a]pyridine-3-carboxamide mono-hydrochloride, 6-chloro-2-ethyl-N-(4-(4-(4-(trifluoromethoxy) phenyl)piperidine-1-yl)benzyl)imidazo[1,2-a]pyridine-3-carboxamide mono-phosphate, or 6-chloro-2-ethyl-N-(4-(4-

(4-(trifluoromethoxy)phenyl)piperidine-1-yl)benzyl) imidazo[1,2-a]pyridine-3-carboxamide mono-tosylate;

which mono-acid addition salt is 6-chloro-2-ethyl-N-(4-(4-(4-(trifluoromethoxy)phenyl)piperidine-1-yl)benzyl)imidazo[1,2-a]pyridine-3-carboxamide mono-hydrochloride having the following peaks in an X-ray Powder Diffraction (XRPD) spectrum obtained by irradiation with Cu-$K_{\alpha}$-radiation (Cu-$K_{\alpha}$):

6.4° 2θ, 8.1° 2θ, 16.2° 2θ, 17.2° 2θ, 24.3° 2θ and 25.0° 2θ, +0.2° 2θ;

or which mono-acid addition salt is 6-chloro-2-ethyl-N-(4-(4-(4-(trifluoromethoxy)phenyl)piperidine-1-yl)benzyl)imidazo[1,2-a]pyridine-3-carboxamide mono-phosphate having the following peaks in an X-ray Powder Diffraction (XRPD) spectrum obtained by irradiation with Cu-$K_{\alpha}$-radiation (Cu-$K_{\alpha}$):

9.0° 2θ, 10.7±0.2° 2θ, 11.7° 2θ, 14.8° 2θ, 18.4° 2θ, 19.3° 2θ, and 21.8° 2θ, 22.8° 2θ, 0.2° 2θ;

or which mono-acid addition salt is 6-chloro-2-ethyl-N-(4-(4-(4-(trifluoromethoxy)phenyl)piperidine-1-yl)benzyl)imidazo[1,2-a]pyridine-3-carboxamide mono-tosylate having the following peaks in an X-ray Powder Diffraction (XRPD) spectrum obtained by irradiation with Cu-$K_{\alpha}$-radiation (Cu-$K_{\alpha}$):

4.0° 2θ, 11.4° 2θ, 12.2° 2θ, 14.4° 2θ, 17.7° 2θ, 18.9° 2θ, 19.7° 2θ, 20.3° 2θ, 23.2° 2θ, and 26.7° 2θ, ±0.2° 2θ.

Figure 2A:
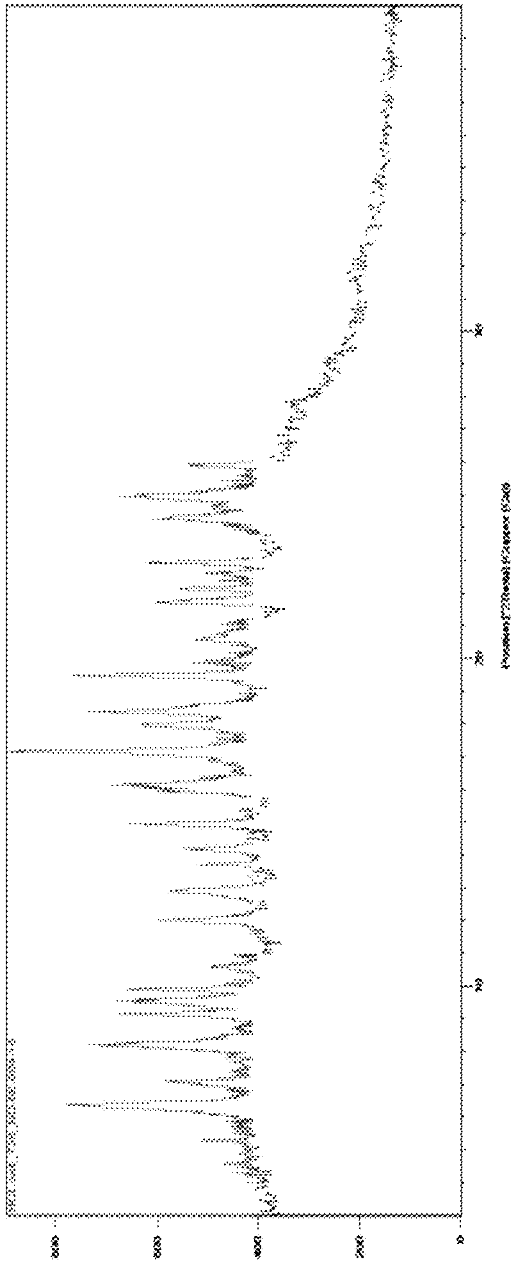
FIGS. 2A and 2B show an XRPD spectrum of the mono-HCl-form and mono-phosphate form of 6-chloro-2-ethyl-N-(4-(4-(4-(trifluoromethoxy)phenyl)piperidine-1-yl)benzyl)imidazo[1,2-a]pyridine-3-carboxamide, respectively.

6. The mono-hydrochloride salt according to claim 5, having an XRPD spectrum essentially as shown in FIG. 2*a*.

Figure 2B:
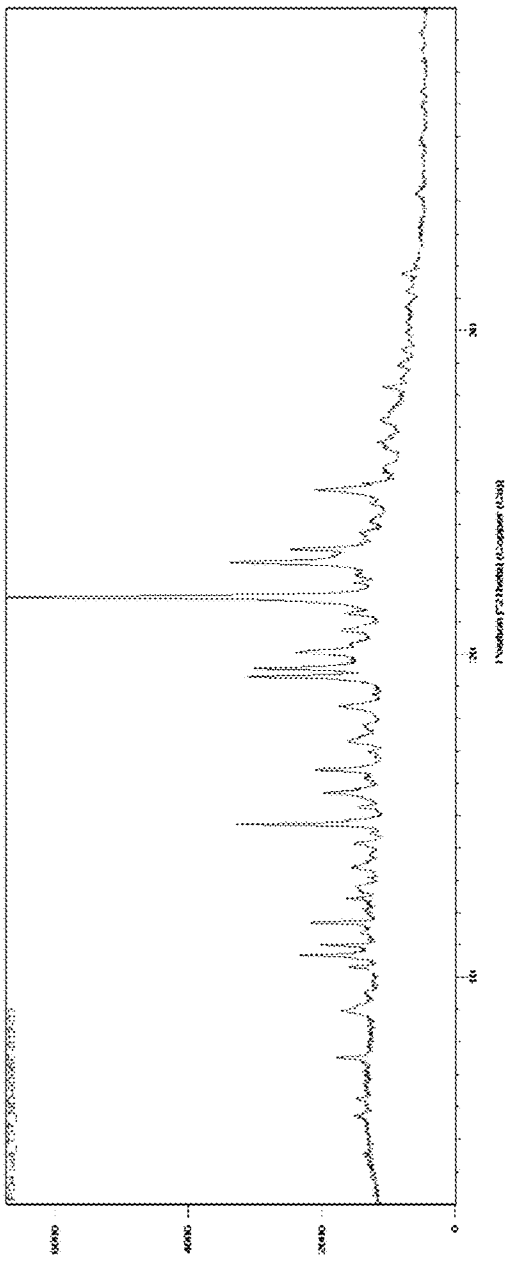

7. The mono-phosphate salt according to claim 5, having an XRPD spectrum essentially as shown in FIG. 2*b*.

Figure 3:
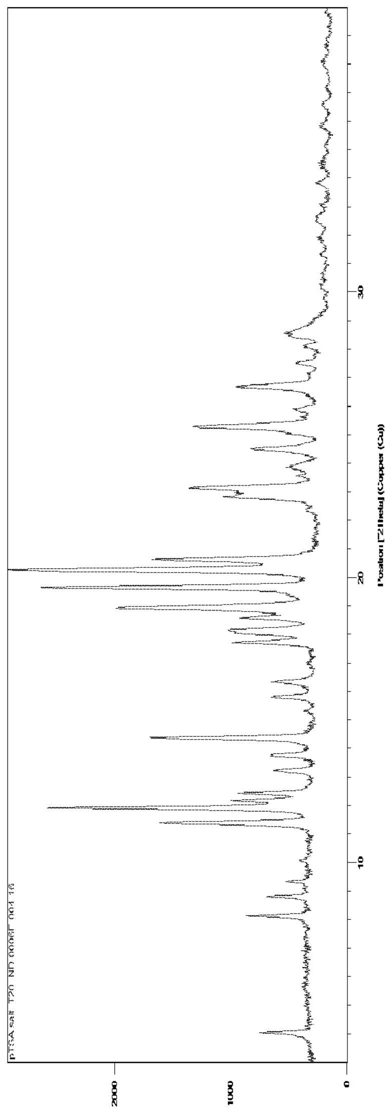
FIG. 3 shows an XRPD spectrum of the mono-tosylate form of -chloro-2-ethyl-N-(4-(4-(4-(trifluoromethoxy)phenyl)piperidine-1-yl)benzyl)imidazo[1,2-a]pyridine-3-carboxamide.

8. The mono-tosylate salt according to claim 5, having an XRPD spectrum essentially as shown in FIG. 3.

9. A pharmaceutical composition comprising at least one compound according claim 1 or a mono-acid addition salt according to claim 5, together with at least one pharmaceutically acceptable carrier, excipient and/or diluent.

10. The pharmaceutical composition according to claim 9, further comprising at least one other pharmaceutically active agent.

11. A method for making the compound of claim 1, said method comprising the steps:

providing, in any order, 6-chloro-2-ethyl-N-(4-(4-(4-(trifluoromethoxy)phenyl)piperidine-1-yl)benzyl)imidazo[1,2-a]pyridine-3-carboxamide free base and para-toluenesulphonic acid in a stoichiometric ratio of 1:2;

mixing and dissolving them in a suitable solvent or solvent mixture; and evaporating the solvent or solvent mixture.

12. The method according to claim 11, wherein the solvent or solvent mixture is isopropylalcohol (IPA), tetrahydrofuran (THF), acetone or a mixture of THE and acetone.

13. A method for preparing the mono-acid addition salt of claim 5, said method comprising the steps:

providing, in any order, 6-chloro-2-ethyl-N-(4-(4-(4-(trifluoromethoxy)phenyl)piperidine-1-yl)benzyl)imidazo[1,2-a]pyridine-3-carboxamide free base and an acid selected from hydrochloric acid, phosphoric acid and para-toluenesulphonic acid in a stoichiometric ratio of 1:1;

mixing and dissolving them in a suitable solvent or solvent mixture; and evaporating the solvent or solvent mixture.

14. The method according to claim 13, wherein the solvent or solvent mixture is isopropylalcohol (IPA), tetrahydrofuran (THF), acetone or a mixture of THE and acetone.

15. A method for the treatment of a bacterial infection, comprising application of a suitable amount of a compound according to claim 1 or claim 5 to a patient in need of such treatment.

16. The method of claim 15, wherein the bacterial infection is tuberculosis or Buruli ulcer.

* * * * *